United States Patent
Lieberman et al.

(10) Patent No.: US 11,384,356 B2
(45) Date of Patent: *Jul. 12, 2022

(54) COMPOSITION AND METHOD FOR OLIGONUCLEOTIDE DELIVERY

(71) Applicant: The Children's Medical Center Corporation, Boston, MA (US)

(72) Inventors: Judy Lieberman, Brookline, MA (US); Lee Adams Wheeler, Boston, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/421,781

(22) Filed: May 24, 2019

(65) Prior Publication Data

US 2019/0359987 A1 Nov. 28, 2019

Related U.S. Application Data

(62) Division of application No. 13/991,980, filed as application No. PCT/US2011/063538 on Dec. 6, 2011, now Pat. No. 10,378,016.

(60) Provisional application No. 61/420,188, filed on Dec. 6, 2010.

(51) Int. Cl.
C12N 15/113 (2010.01)
C12N 15/11 (2006.01)

(52) U.S. Cl.
CPC ........ *C12N 15/1138* (2013.01); *C12N 15/111* (2013.01); *C12N 15/1132* (2013.01); *C12N 2310/14* (2013.01); *C12N 2310/16* (2013.01); *C12N 2310/3183* (2013.01); *C12N 2310/3519* (2013.01)

(58) Field of Classification Search
None
See application file for complete search history.

(56) References Cited

U.S. PATENT DOCUMENTS

| | | | |
|---|---|---|---|
| 5,869,641 | A | 2/1999 | Jayasena |
| 7,655,787 | B2 | 2/2010 | Guo |
| 2003/0013668 | A1 | 1/2003 | Veerapanane |
| 2006/0105975 | A1 | 5/2006 | Pendergast |
| 2006/0293262 | A1 | 12/2006 | Lieberman |
| 2008/0214436 | A1 | 9/2008 | Yu |
| 2008/0214489 | A1 | 9/2008 | Keefe |
| 2009/0148944 | A1 | 6/2009 | Rossi |

OTHER PUBLICATIONS

Zhou et al., "Aptamer-targeted cell-specific RNA interference", Silence 1(1) 4 (2010).

Zhou et al., "Selection, characterization and application of new RNA HIV gp 120 aptamers for facile delivery of Dicer substrate siRNAs into HIV infected cells", Nucleic Acids Res 37(9) 3094-3109 (2009).

Zhou et al., "Novel dual inhibitory function aptamer-siRNA delivery system for HIV-1 therapy", Mol Ther 16(8) 1481-1489 (2008).

Wheeler et al., "Inhibition of HIV transmission in human cervicovaginal explants and humanized mice using CD4 aptamer-siRNA chimeras", J Clin invest 121(6) 2401-2412 (2011).

Supplementary data for Zhou et al., [online, retrieved on May 25, 2017], Retrieved from the internet: https://academic.oup.com/nar/article/37/9/3094/1160214/Selection-characterization-and-application-of-new 10 pages.

Abdool Karim et al., "Effectiveness and safety of tenofovir gel, an antiretroviral microbicide, for the prevention of HIV infection in women", Science 329(5996) 1168-1174 (2010).

Capodici et al., "Inhibition of HIV-1 infection by small interfering RNA-mediated RNA interference", J Immunol 169(9) 5196-5201 (2002).

Coburn et al., "Potent and specific inhibition of human immunodeficiency virus type 1 replication by RNA interference", J Virol 76(18) 9225-9231 (2002).

Collins et al., "Development of an in vitro organ culture model to study transmission of HIV-1 in the female genital tract", Nat Med 6(4) 475-479 (2000).

Dassie et al., "Systemic administration of optimized aptamer-siRNA chimeras promotes regression of PSMA-expressing tumors", Nat Biotechnol 27(9) 839-849 (2009).

Davis et al., "Staining of cell surface human CD4 with 2'-F-pyrimidine-containing RNA aptamers for flow cytometry", Nucleic Acids Res 26(17) 3915-3924 (1998).

Fatkenheuer et al., "Subgroup analyses of maraviroc in previously treated R5 HIV-1 Infection", N Engl J Med 359(14) 1442-1455 (2008).

Gulick et al., "Phase 2 study of the safety and efficacy of vicriviroc, a CCR5 inhibitor, in HIV-1-Infected, treatment-experienced patients: AIDS clinical trials group 5211", J Infect Dis 196(2) 304-312 (2007).

Gulick et al., "Maraviroc for previously treated patients with R5 HIV-1 infection", N Engl J Med 359(14) 1429-1441 (2008)I.

Haase et al., "Targeting early infection to prevent HIV-1 mucosal transmission", Nature 464(7286) 217-223 (2010).

Huang et al., "The role of a mutant CCR5 allele in HIV-1 transmission and disease progression", Nat Med 2(11) 1240-1243 (1996).

Jacque et al., "Modulation of HIV-1 replication by RNA interference", Nature 418(6896) 435-438 (2002).

Kumar et al., "T cell-specific siRNA delivery suppresses HIV-1 infection in humanized mice", Cell 134(4) 577-586 (2008).

Kuritzkes et al., "HIV-1 entry inhibitors: an overview", Cur Opin HIV AIDS 4(2) 82-87 (2009).

(Continued)

*Primary Examiner* — Tracy Vivlemore
(74) *Attorney, Agent, or Firm* — Nixon Peabody LLP; David S. Resnick; Ravinderjit Braich

(57) ABSTRACT

The invention provides aptamer-gene modulator conjugates, where the aptamer and the gene modulator are linked together. The invention further provides a method for cell-specific delivery of gene modulators to hard to transfect cells such as CD4+ cell.

7 Claims, 46 Drawing Sheets

Specification includes a Sequence Listing.

(56) References Cited

OTHER PUBLICATIONS

Lederman et al., "Prevention of vaginal SHIV transmission in rhesus macaques through inhibition of CCR5", Science 306(5695) 485-487 (2004).
Lee et al., "Expression of small interfering RNAs targeted against HIV-1 rev transcripts in human cells", Nat Biotechnol 20(5) 500-505 (2002).
LEE et al., "Lentiviral delivery of short hairpin RNAs protects CD4 T cells from multiple clades and primary isolates of HIV", Blood 106(3) 818-826 (2005).
Margolis et al., "Selective transmission of CCR5-utilizing HIV-1: the 'gatekeeper' problem resolved?", Nat Rev Microbiol 4(4) 312-317 (2006).
McNamara et al., "Cell type-specific delivery of siRNAs with aptamer-siRNA chimeras", Nat Biotechnol 24(8) 1005-1015 (2006).
Mills et al., "Chemokine receptor-directed agents as novel anti-HIV-1 therapies", Curr Top Med Chem 4(1) 1017-1033 (2004).
Neff et al., "An aptamer-siRNA chimera suppresses HIV-1 viral loads and protects from helper CD4(+) T cell decline in humanized mice", Sci Transl Med 3(66) 66ra6 (2011).
Novina et al., "siRNA-directed inhibition of HIV-1 infection", Nat Med 8(7) 681-686 (2002).
Palliser et al., "An siRNA-based microbicide protects mice from lethal herpes simplex virus 2 infection", Nature 439 (7072) 89-94 (2006).
Peer et al., "Selective gene silencing in activated leukocytes by targeting siRNAs to the integrin lymphocyte function-associated antigen-1", Proc Natl Acad Sci USA 104(1) 4095-4100 (2007).
Robbins et al., "siRNA and innate immunity", Oligonucleotides 19(2) 89-102 (2009).
Scolnik et al., "mAbs: a business perspective", Mabs 1(2) 179-184 (2009).
Song et al., "Sustained small interfering RNA-mediated human immunodeficiency virus type 1 inhibition in primary macrophages", J Virol 77(13) 7174-7181 (2003).
Soutschek et al., "Therapeutic silencing of an endogenous gene by systemic administration of modified siRNAs", Nature 432(7014) 173-178 (2004).
Van't Wout et al., "Macrophage-tropic variants initiate human immunodeficiency virus type 1 infection after sexual, parenteral, and vertical transmission", J Clin Invest 94(5) 2060-2067 (1994).
Wu et al., "Durable protection from Herpes Simplex Virus-2 transmission following intravaginal application of siRNAs targeting both a viral and host gene", Cell Host Microbe 5(1) 84-94 (2009).
Zimmerman et al., "Inherited resistance to HIV-1 conferred by an inactivating mutation in CC chemokine receptor 5 studies in populations with contrasting clinical phenotypes, defined racial background, and quantified risk", Mol Med 3(1) 23-36 (1997).
Xia et al., "Intravenous siRNA of brain cancer with receptor targeting and avidin-biotin technology." Pharm Res 24(12): 2309-2316 (2007).
Low et al., "Discovery and development of folic-acid-based receptor targeting for imaging and therapy of cancer and inflammatory diseases," Acc Chem Res 41(1): 120-129 (2008).

COMPOSITION AND METHOD FOR OLIGONUCLEOTIDE DELIVERY

RELATED APPLICATIONS

This application is a Divisional Application of U.S. Ser. No. 13/991,980 filed Aug. 22, 2013, which is a 35 U.S.C. § 371 National Phase Entry application of International Application No. PCT/US2011/063538 filed Dec. 6, 2011, which designates the U.S., and which claims benefit under 35 U.S.C. § 119(e) of the U.S. Provisional Application No. 61/420,188, filed Dec. 6, 2010, content of which is incorporated herein by reference in their entireties.

GOVERNMENT SUPPORT

This invention was made with government support under Grant No. AI070302 and No. AI090671 awarded by the National Institute of Allergy and Infectious Diseases. The government has certain rights in the invention.

The instant application contains a Sequence listing which has been submitted in ASCII format via EFS-web and is hereby incorporated by reference in its entirety. Said ASCII copy, created on May 10, 2019, is named 13991, 980-701039-068852-USD1_SL.txt and is 21,543 bytes in size.

FIELD OF THE INVENTION

The invention relates to compositions and methods for cell-specific delivery of reagents such as drugs and dyes. Drugs can include nucleic acids, e.g. RNAi agents. The methods and compositions also relate to inhibition of gene expression.

BACKGROUND OF THE INVENTION

The continued spread of the HIV epidemic in the absence of an effective prevention underscores the need to develop ways to interrupt HIV transmission. One attractive strategy is a topical vaginal microbicide. For example, the CAPRISA004 study demonstrated partial protection from sexual transmission of HIV-1 by vaginally applied tenofovir gel (Abdool Karim, Q. et al., *Science* 329, 1168-1174).

Multiple groups have shown that RNA interference (RNAi) can be harnessed to inhibit HIV infection in vitro (Novina, C. D. et al. *Nat Med* 8, 681-686 (2002); Capodici, J., et al., *J Immunol* 169, 5196-5201 (2002); Jacque, J. M., et al. *Nature* 418, 435-438 (2002); Lee, N. S. et al. *Nat Biotechnol* 20, 500-505 (2002); Coburn, G. A. & Cullen, B. R./*Virol* 76, 9225-9231 (2002)). However, application of RNAi for preventing or inhibiting HIV infection is not simple. One must first overcome the hurdle of in vivo siRNA delivery to the immune cells that HIV infects, namely, principally CD4+ T cells and macrophages, which are resistant to most transfection techniques. For example, the cholesterol-conjugated siRNAs that protect against lethal HSV-2 infection in mice (Wu, Y. et al. *Cell Host Microbe* 5, 84-94 (2009)), although efficiently taken up by epithelial cells throughout the genital tract, including deep in the lamina propria, do not knockdown gene expression in T lymphocytes or macrophages when applied intravaginally to mice.

Peer, D., et al. (*Proc. Natl Acad Sci USA* 104, 4095-4100 (2007)) describes a method for cell-specific siRNA transfection of immune cells that uses a fusion protein composed of a cell-targeting antibody fragment joined to a protamine peptide that binds nucleic acids (Peer, D., et al. *Proc Natl Acad Sci USA* 104, 4095-4100 (2007)). siRNAs mixed with the fusion protein are taken up by and knockdown gene expression in cells bearing the cognate surface receptor, both in vitro and in tissues following intravenous injection. Modifications of this approach inhibit HIV infection in humanized mice (Kumar, P. et al. *Cell* 134, 577-586 (2008)). However, antibody-based fusion proteins are very expensive to manufacture, potentially immunogenic and typically require refrigerated storage, making them ill-suited for use in a microbicide for resource-poor settings (Scolnik, P. A. *MAbs* 1, 179-184 (2009)).

Accordingly, there is a need in the art for compositions and methods for cell-specific siRNA transfection of immune cells.

SUMMARY OF THE INVENTION

The present invention is directed to a novel delivery system for cell-specific delivery of reagents such as small molecules (e.g. therapeutic agents), peptides, proteins, and nucleic acids (e.g. RNAi agents, antisense RNAs, microRNAs, pre-microRNAs, antagomirs, ribozymes, decoy oligonucleotides, and aptamers), and analogs and derivatives thereof. The methods and compositions also relate to cell-specific delivery of siRNAs and microRNAs, including its application in HIV microbicides that can be administered topically to prevent HIV infection. The inventors have discovered that by using a particular type of linker to attach an siRNA agent to an aptamer structure, an siRNA can be effectively delivered to a cell. Moreover, the inventors discovered that unlike attachment of siRNA to cholesterol as a delivery vehicle, the novel construct also effectively delivers the siRNA into CD4+ T cells and macrophages, dendritic cells, and any cell lines expressing CD4. Accordingly, the invention also provides methods of inhibiting, preventing and treating HIV infection using the novel delivery vehicle, which can also be applied in connection with a topically administered pharmaceutical composition.

In one aspect, the invention provides a conjugate comprising an aptamer and a modulator, wherein the aptamer and the modulator are linked to each other by a linker. In some embodiments, the linker is a single-stranded oligonucleotide, wherein the aptamer and the modulator are linked to opposite ends of the single-stranded oligonucleotide. In some other embodiments, the linker is a double-stranded oligonucleotide comprising a first oligonucleotide strand and a second oligonucleotide strand, and the first strand is linked to the aptamer and the second strand is linked to the modulator. In some embodiments, the modulator and the second strand are linked by a non-nucleotidic linker. In some embodiments, the first strand and the aptamer are not linked by a non-nucleotidic linker. In some embodiments of the aspects described herein, the modulator is a gene modulator.

In some embodiments, the aptamer-modulator conjugate is a single-stranded oligonucleotide comprising an aptamer portion and a modulator portion. Without limitations, after secondary folding the single-stranded oligonuceltioide can reconstitute the aptamer portion and the modulator portion, e.g., a gene modulator, e.g. an antisense RNA, a hairpin RNA (shRNA) that modulates RNA interference, a miRNA, a ribozyme, a mRNA, or a hairpin loop encoding an siRNA, miRNA, ribozyme, mRNA etc.

In another aspect, the invention provides a method of inhibiting the expression of a target gene in cell, the method comprising contacting the cell with a conjugate comprising an aptamer and a gene modulator, wherein the aptamer is CD4 aptamer and the gene modulator inhibits the expression of an endogenous gene, a transgene, or an exogenous gene.

In yet another aspect, the invention provides a method of inhibiting or preventing HIV infection in a cell, the method comprising contacting a cell with a conjugate comprising an aptamer and a gene modulator, wherein the aptamer is a CD4 aptamer and the gene modulator inhibits the expression of an HIV gene and/or a cell gene required for HIV infection, replication and/or function. In some embodiments the aptamer and the gene modulator are covalently linked to each other. In some embodiments, cell is a CD4+ cell.

In yet another aspect, the invention provides a method of treating and/or preventing HIV infection in a subject in need thereof, the method comprising administering to the subject a conjugate, typically at therapeutically effective amount, wherein the conjugate comprises an aptamer and a gene modulator, wherein the aptamer is a CD4+ aptamer, and the gene modulator inhibits the expression of an HIV gene and/or a endogenous cell gene. In some embodiments the aptamer and the gene modulator are covalently linked to each other.

In still yet another aspect, the invention provides a kit comprising an aptamer-modulator conjugate, wherein the aptamer is a CD4 aptamer.

In one other aspect, the invention provides a method of modulating phenotype of a CD4+ cell, the method comprising contacting a cell with a conjugate comprising an aptamer and a gene modulator, wherein the aptamer is CD4 aptamer and the gene modulator inhibits the expression of an endogenous gene, a transgene, or an exogenous gene. In some embodiments, the cell is a CD4+ cell.

In another aspect, the invention provides a method of a method of treating and/or preventing a cancer of the immune system in a subject in need thereof, the method comprising administering to the subject a conjugate, typically at therapeutically effective amount, wherein the conjugate comprises an aptamer and a gene modulator, wherein the aptamer is a CD4+ aptamer, and the gene modulator inhibits the expression of an oncogene.

BRIEF DESCRIPTION OF THE DRAWINGS

FIG. 1A shows a design of CD4-AsiC containing clone 9 CD4 aptamer and siRNA directed against CCR5. Sequences shown are SEQ ID NO: 67 (aptamer+ sense) and SEQ ID NO: 58 (antisense). Scheme for synthesis is given in FIG. 5A. CD4-AsiCs or PSMA-AsiCs against CCR5 were Cy3-labeled at the 3' terminus of the antisense siRNA strand and incubated with primary human blood monocyte-derived macrophages (MDM) (FIG. 1B) 3 or freshly isolated CD4+ T-lymphocytes from a healthy donor (FIG. 1C). Uptake was assessed 24 h later by fluorescence microscopy (data not shown) and flow cytometry (FIGS. 1B and 1C). Data are representative of three independent experiments. MFI of each peak is shown (mock, blue; treated, red). Transfection controls used Oligofectamine (OF, MDM) or nucleofection (T cells). In FIG. 1D, specific siRNA delivery to CD4+ cells in a mixed population of resting PBMCs was assessed by flow cytometry. Freshly isolated PBMCs were treated with 4 µM Cy3-labeled AsiCs and uptake of the labeled siRNA was assessed by flow cytometry after 24 h. Cells were co-stained with CD3, CD8, CD4, or CD14. The top two rows are gated on CD3+ lymphocytes, the bottom row on CD14+ monocytes. In this mixed population of primary blood cells, in the absence of OF transfection, Cy3-labeled CD4-AsiCs were preferentially taken up by CD3+CD4+ T cells (top) and CD4+ CD14+ monocytes (bottom), compared to CD3+CD8+ I cells (middle). Representative dot plots of three experiments using different donor samples are shown. PSMA-AsiCs transfect only monocytes efficiently only in the presence of OF.

In FIGS. 3A and 3B the Transfection controls used OF (FIGS. 3A and 3B) or nucleofection (FIGS. 3C and 3D). Mean (±S.E.M.) intracellular p24 expression (normalized relative to mock) was measured by flow cytometry 48 h later. CD4-AsiCs inhibited HIV replication (FIGS. 3A and 3C, n=3 and *p<0.05 and **p<0.005 two-tailed t test). Insets show representative histograms of MDMs (FIG. 3A) and CD4+ lymphocytes (FIG. 3C) treated with gag/vif CD4-AsiC (gray, uninfected; blue, mock treated; red, CD4-AsiC-treated). HIV infection of MDMs infected for 48 h with HIV-1BaL and then treated with 4 µM total final concentration of CD4-AsiCs or PSMA-AsiCs targeting gag, vif and CCR5 was evaluated 48 h later by fluorescence in situ hybridization (FISH) using FITC (green)-labeled probes complementary to an 800 nt region of HIV genomic RNA. The active strand of the CCR5 construct was Cy3-labeled at the 3'-end (red). Cells were also stained with DAPI (blue). HIV RNA was virtually undetectable in MDMs treated with CD4-AsiC compared to controls. To evaluate gene silencing independently of the effect of the CD4 aptamer on blocking viral entry, HIV replication was assessed by infection with VSV(G)-pseudotyped virus containing a luciferase reporter gene (FIGS. 3B and 3D). Primary MDM (FIG. 3B) and CD4+ T-cells (FIG. 3D) cells were pretreated for 48 hours before infection with 4-litM mixtures of CD4- or PSMA-AsiCs targeting gag and vif or containing scrambled siR-NAs. Luciferase activity, measured 48 hours later, was significantly inhibited in cells treated with CD4-AsiCs directed against either viral or luciferase genes (mean±SEM normalized to mock; n=3; *P<0.05, **P<0.005). Luciferase activity was inhibited in cells treated with CD4-AsiCs directed against either viral or luciferase genes.

In FIG. 4A, Cy3-labeled AsiCs were applied to the epithelium of agarose-embedded polarized explants 72 h and 48 h before flow cytometry analysis of single cell suspensions for Cy3-uptake (FIG. 4B) and CCR5 knockdown (FIG. 4C). Cells were stained for CD3, CD4, CD8, and CD14 and analyzed by gating on the indicated subpopulations. Uptake, assessed by Cy3 fluorescence, was highest in CD3+CD4+ T cells and CD14+CD4+ tissue macrophages and CCR5 knockdown was seen only in these CD4+ populations. The average (±SEM) means fluorescence intensity (MFI) of cells treated with CD4-AsiC is shown relative to PSMA-AsiC treatment in FIG. 4D (*p<0.05, **p<0.01, 2-tailed t test). Data are averaged from quadruplicate samples from a single donor and are representative of results obtained using three independent donor samples. FIG. 4E is a schematic of HIV challenge experiment. Polarized vaginal explants from 3 donors were pretreated with increasing doses (1 NM to 16 NM) of CD4-AsiCs targeting gag/vif (FIG. 4F), CCR5 (FIG. 4G), or a cocktail targeting all three genes (FIG. 4H) for 48 h before HIV-1BaL challenge. Viral replication in the mucosa, measured over 12 days by p24-ELISA of the lower transwell culture medium, showed specific dose-dependent inhibition by CD4-AsiCs against viral gag/vif (red triangles, FIG. 4F), or host CCR5 (red triangles, FIG. 4G) compared to mock controls (blue squares). CD4-AsiCs (red triangles, FIG. 4H), suppressed HIV-1 more effectively when applied at 4 pM total final concentration than the viral or CCR5 CD4-AsiCs at the same total concentration. p24 Ag levels (mean+SEM) were normalized to the mock-treated samples (blue squares) so that data from multiple experiments could he combined (*p<0.05, "p<0.01). In FIG. 4H, PSMA-AsiC treatment (yellow circles) did not inhibit viral production. In FIGS. 4I and 4J, HIV inhibition by the CD4-aptamer on its own was compared to the gag and vif CD4-AsiC by treating the apical surface of vaginal explants with serial 2-fold dilutions (1-8 pM) of each. HIV-1 p24 Ag secretion was measured by ELISA as above and normalized to mock treatment controls (+SEM). Data are representative of independent experiments from 2 donors, performed in quadruplicate (*P<0.05, **P<0.0001, 1-way ANOVA with Dunnett multiple-comparison test).

FIG. 6A shows the denaturing gel electrophoresis of the purified clone 9 IVT product. The purified chimera migrates as a single band just above the 100 nt RNA marker, consistent with the expected size of the CD4 aptamer linked to the siRNA passenger strand (~107 nt). The purified aptamer migrates below the 100 nt marker, consistent with its expected size (86 nt). In FIG. 6B analysis of the annealed CD4-AsiC by native gel electrophoresis shows two distinct components-a more abundant slowly migrating product and a less abundant more rapidly migrating product. As expected, the annealed CD4-AsiC RNA migrates more slowly than the purified aptamer lacking the siRNA.

In FIG. 7C, representative dot plots compare mock-treated cells (left panel) with cells treated with increasing concentrations of Cy3-labeled chimeras.

In FIGS. 11A and 11B the average mean fluorescence intensity (MFT) of intracellular p24 staining of three independent experiments using HeLa-CD4 cells is graphed. To combine data from independent experiments, the mean background fluorescence of uninfected control cells was subtracted and the signal was then normalized to the mean value of HIV-infected mock-treated control cells. (Shown are mean±SEM; *p<0.05; **p<0.005, two-tailed t test). In FIG. 11C Jurkat cells were treated 48 h after HIV-lib infection with an equimolar mixture of either clone 9 (left) or clone 12 (right) CD4-AsiCs encoding gag and vif siRNAs. Intracellular p24 staining was measured 48 h later by flow cytometry. The blue histogram represents p24 staining of HIV-infected mock-treated cells and the gray histogram represents uninfected controls. In both cell lines suppression of HIV replication by the CD4-AsiCs increased with dose.

In FIG. 12A, data represent average relative mean fluorescence intensity of surface receptor expression from duplicate samples from two patient samples, normalized with respect to mock-treated cells from the same donor. Errors bars=SEM.

In FIG. 13A, formalin-fixed paraffin embedded tissue sections from cervical explants treated with CD4-AsiC or PSMA-AsiC for 24 hours were stained with hematoxylin and eosin. No histological changes in tissue integrity were detected in the AsiC-treated tissue. 10× magnification. Scale bars, 100 um. FIG. 13B shows that there was no evidence of cytotoxicity, as measured by LDH release in culture medium after the cervicovaginal explants had been treated with CD4-AsiC or PSMA-AsiC for 24 h. Treatment with 1% Triton X-100 served as the positive control. Data represent mean (±SEM) from quadruplicate biological replicates in one representative experiment of three independent experiments. In FIG. 13C, qRT-PCR was used to measure mRNA expression in cervical tissue explants 6 and 24 h after treatment with CD4-AsiCs or PSMA-AsiCs. Data are normalized to GAPDH niRNA. Cytokine and interferon responsive genes that might be triggered by innate immune RNA receptors were evaluated. Data represent mean (±SEM) from at least three independent experiments (*p<0.05; "p<0.01, one way ANOVA with Dunnett comparison test).

FIG. 14A shows the 3C stick aptamer-siRNA conjugate. To eliminate the need for an siRNA-target-specific cDNA intermediate, the CCR5-targeting CD4 AsiC was re-designed to incorporate a 3-carbon (3C) stick adaptor strand, which allowed direct conjugation of the active siRNA strand to the CD4 aptamer. While the 3C stick model was taken up less efficiently by CD4+ T cells than the original design after 72 h (FIG. 14B), target CCR5 silencing was unchanged (FIG. 14C). The aptamer portion of the conjugate was synthesized by T7 polymerase IVT of a cDNA intermediate as described in the Examples section. The sense strand comprising the linker strand and the antisense strand were commercially synthesized. All three strands were combined in a 1:1:1 molar ratio, heat denatured, and annealed as described in the Examples section. These strands were normal PAGE purified, extracted, desalted before using for conjugate formation. Sequences shown are SEQ ID NO: 62 (aptamer), SEQ ID NOS 59 and 75 (sense+linker), and SEQ ID NO: 71 (Cy3 labeled antisense).

In FIGS. 17A-17C, NOD/SCID-BLT mice (2 per group) were treated intravaginally (IVAG) with indicated doses (5-80 pmol of each AsiC) of a mixture of Cy3-labeled CD4-AsiCs against CCR5 and unlabeled CD4-AsiCs targeting CD45, or with PBS. Two days later a single-cell suspension extracted from vaginal tissue was analyzed by flow cytometry for Cy3-labeled siRNA uptake and target gene knockdown. Cells were stained for CD3, CD4, CD8, and CD14 and analyzed by gating on the indicated subpopulations. In FIG. 17B representative histograms are shown for cells from one mock-treated mouse (blue) and one mouse treated with 80 pmol of CD4-AsiCs (red). In FIG. 17C, the average (±S.E.M.) mean fluorescence intensity (MFI) of CD4+ T cells in the vaginal tissue of CD4-AsiC-treated mice shows a dose-dependent decrease in both CD45 and CCR5 expression relative to mock-treated controls, but the MFI of CD8+ T cells does not (mean±SEM; *P<0.01, P<0.001, 1-way ANOVA with Dunnett multiple-comparison test). FIG. 17D is schematic of HIV challenge experiment. NOD/SCID/y-/-(NSG)-BLT mice were treated IVAG with CCR5 CD4-AsiCs 48 hr (80 pmol) and 24 hr (40 pmol) before, and 40 pmol each of gag and vif CD4-AsiCs 24 h before and 4 h after, IVAG challenge with HIVIR-csF. CD4-AsiC treatment was compared with treatment with the same concentration of CD4 aptamer or mock treatment with PBS (n=4 per group). Mice were observed for 12 weeks after HIV challenge. The effect of treatment on survival (FIG. 17E), plasma HIV antigen by ELISA (FIG. 17F), plasma HIV RNA analyzed by qRT-PCR (FIG. 17G, dashed line=detection limit), and circulating CD4+/CD8+ T cell ratio (FIG. 17H) is shown. Data are mean±SEM. $1^{2t}$<0.001, ***P<0.0001 vs. mock, 2-way ANOVA with Bonferroni correction.

FIG. 19A: To investigate the mechanism of CD4-chimera processing the inventors first tested whether CD4-AsiCs are Dicer substrates in vitro by incubating CD4-chimeras against CCR5 with recombinant Dicer at 37° C. After 2 h, chimeras were virtually completely digested to a ~20-23 ntsiRNA duplex that migrated like a commercially synthesized CCR5-siRNA. FIG. 19B: Intracellular processing was demonstrated by treating primary CD4+ T cells with CD4-AsiCs bearing CCR5-siRNAs labeled with 32 P at their 5'-end. T cells were incubated for 24 or 72 h with radiolabeled chimeras. Total RNA was harvested by TRTZOL extraction and the same total number of counts was loaded onto a native polyacrylamide gel. Nucleofection of 5'-end-labeled chimeras and commercially-synthesized siRNA duplexes served both as controls and size standards. While some cleavage was seen at 24 h post treatment, after 72 h of treatment, the 32 P labeled chimera isolated from cellysates was ~21-23 nt in length, suggesting that these fragments are processed in primary CD4+ cells into siRNA-sized duplexes. FIG. 19C: To evaluate the functional dependence of CD4-AsiC-mediated silencing on intracellular Dicer expression the inventor evaluated target gene silencing of lipofectamine-transfected CD4-chimeras in either wild-type (WT) or Dicer-/- HCT-116 cells (Cummins J M, et al. Proc Nati Acad Sci USA. 2006; 103(10):3687-3692). Silencing of lamin A by CD4-AsiCs was only observed in WT cells, whereas gene knockdown by transfected lamin A siRNAs was not differentially affected by Dicer expression. Thus, CD4-AsiCs are Dicer substrates and are processed in primary cells to release functional siRNA duplexes in a Dicer-dependent manner.

FIG. 20A: To confirm that CD4-AsiC functioned in the RNAi pathway and validate that AsiC-mediated silencing was due to siRNA-directed cleavage of target gene mRNA, we adopted a modified 5'-RACE (rapid amplification of cDNA ends) technique. Using primary MDMs treated with CD4-AsiCs against CCR5, total RNA was isolated 24 and 72 h after treatment. A predicted CCR5 cleavage fragment of 85 bp in length was amplified using a CCR5-specific and 5'-RACE adaptor-specific primer set. CCR5-siRNAs transfected with Oligofectamine served as a positive control. FIG. 20A discloses SEQ ID NOS 76, 44 and 77-78, respectively, in order of appearance. FIG. 20B: Amplified bands were specific to both transfected cells and only detected 72 h after incubation with the CD4-chimera. Sequencing of the amplified fragments confirmed that cleavage occurred 10 nt from the 5'-end of the CCR5 antisense strand, as predicted. FIG. 20C: Functional silencing of target CCR5 protein was confirmed by immunoblot using protein isolated form the same TRIZOL extraction. These data, together with FIG. 19, indicate that CD4-AsiCs are processed by Dicer to release functional siRNA duplexes that direct target mRNA cleavage via the RNAi pathway.

FIGS. 21A and 21B: MDMs from healthy donors were pre-treated for 48 h with either CD4-AsiCs bearing Cy3-labeled siRNAs against CCR5 or CD4 aptamers alone. Cells were then infected with HIV-IRO. Viral replication, assessed by p24-Ag release into the culture supernatant, was measured by ELISA for 8 d following infection. Averaged (±S.E.M.) p24-Ag, normalized relative to mock-treated infected controls for two independent experiments using separate donors, shows dose-dependent inhibition of p24 Ag release in chimera-treated cells, whereas cells treated with the CD4 aptamer alone showed no significant differential effect relative to mock-treated controls. (p<0.001, *p<0.0001 one-way ANOVA with Dunnett multiple comparison test). FIG. 21C: Eight days following infection cells were harvested and analyzed by flow cytometry for Cy3-siRNA uptake, CCR5 expression, and intracellular p24 by flow cytometry. Representative histograms of one patient sample show a dose-dependent increase in Cy3-siRNA uptake and decrease in both CCR5 expression and HIV infection measured by intracellular p24 staining.

FIG. 22A: Primary CD4 T cells and monocyte-derived macrophages (MDMs) obtained from healthy patient donor blood were treated with the indicated concentration of CD4-AsiCs bearing siRNAs against TREX1 and target gene mRNA was analyzed by qRT-PCR 48 h later. In both CD4 T cells (left) and MDMs (right), there was a dose dependent decrease in TREX1 mRNA expression relative to GAPDH. FIG. 22B: To test for uptake and gene silencing in situ, 3 mm×3 mm sections of human cervicovaginal tissue was polarized in a transwell system. The epithelial surface of each tissue section was twice treated at 48 h and 24 h prior to collagenase digest, RNA extraction, and analysis by qRT-PCR. While target TREX1 mRNA was reduced by over 75% in MDM (left panel) and by over 90% in CD4 T cells (middle panel), whereas no decrease was observed CD19+ B cells. FIG. 22 Crl'o test whether TREX1 AsiCs were able to prevent HIV transmission in situ, polarized human cervicovaginal tissue was twice treated with CD4-AsiCs bearing siRNAs against either TREX1 (red) or CCR5 as a positive control (yellow). PBS treated tissue served as a negative control (blue). Tissues were then challenged with HIVBaL for 24 h and p24-Ag production in the lower transwell chamber was analyzed by p24-ELISA over 9 d post challenge. Chimeras bearing siRNAs against TREX1 reduced viral replication by about 70% relative to mock treated tissue, whereas chimeras against the CCR5 coreceptor reduced transmission by about 95% at the same concentration, suggesting that preventing viral entry more effectively inhibits viral replication. FIG. 22D: TREX1 mediated protection from viral transmission was tested in vivo using humanized BLT mice as depicted in the experimental schematic. A dosing regimen for a previously published strategy that blocked viral transmission served as a positive control. FIG. 22E: Relative to PBS treated controls (blue), mice treated with chimeras against either TREX (red) or CCR5 (green) maintained relatively stable CD4$^+$ cell counts over 8 weeks. FIG. 22F: While p24 Ag content in the serum was undetectable in the positive control, HIV antigenemia was observed in the TREX1 samples after 6 weeks post challenge, though at an order of magnitude lower than the PBS treated controls. This suggests that while knocking down expression of TREX1 might not be as effective at blocking transmission relative to CCR5 for example, it can effectively reduce viral replication over the first 8 weeks post exposure.

FIG. 23A is a schematic representation of full length CD4 apatamer showing the location of truncated 5'-loop and 3'-loop in the full length CD4 apatamer. Sequences shown are SEQ ID NO: 67 (aptamer+sense) and SEQ ID NO: 61 (antisense). FIG. 23B: Primary CDr cells were treated with the two truncated CD4-aptamer constructs: Cy5-labeled 5'-loop or FAM-labeled 3'-loop. Analysis of cells both with (right panel) and without (left panel) acid wash by flow cytometry suggests that only the 5'-Cy5 labeled loop is internalized by the CD4$^+$ cells. Acid wash would degrade any nucleic acids interacting non-specifically with the membrane or otherwise hound to the surface so by using acid wash one can look solely at that which has been internalized into the cell. Sequences show are SEQ ID NO: 65 (truncated CD4 aptamer, 5'-loop) and SEQ ID NO: 66 (truncated CD4 aptamer, 3'-loop FIGS. 24A-24E show durability of protection against HIV infection in mice using CD4-AsiCs. CD4-AsiCs were applied IVAG at various time periods prior to viral challenge according to the schematic and dosing regimens shown in FIGS. 24A and 24B. CD4-AsiCs differentially inhibit vaginal HIV transmission to humanized R I, T mice (FIGS. 24C-24E). Four groups of NSG-BLT mice were treated IVAG with CCR5 CD4-AsiCs, gag and vif chimeras, or a combination of the three according to the dosing regimen shown in FIG. 24B, and then challenged IVAG with HIVJR-CSF. CD4-AsiC treatment was compared to mock treatment with PBS (n=4 per group). Mice were observed for 12 weeks after HIV challenge. Shown is the effect of treatment on circulating CD4+/CD8+ T cell ratio (FIG. 24C), plasma HIV Ag (FIG. 24D, assessed by ELISA), and plasma HIV RNA (FIG. 24E, analyzed by qRT-PCR. Data are mean±SEM. *P<0.01, ***P<0.0001 vs. mock, 1-way ANOVA.

DETAILED DESCRIPTION

Figure 1A:
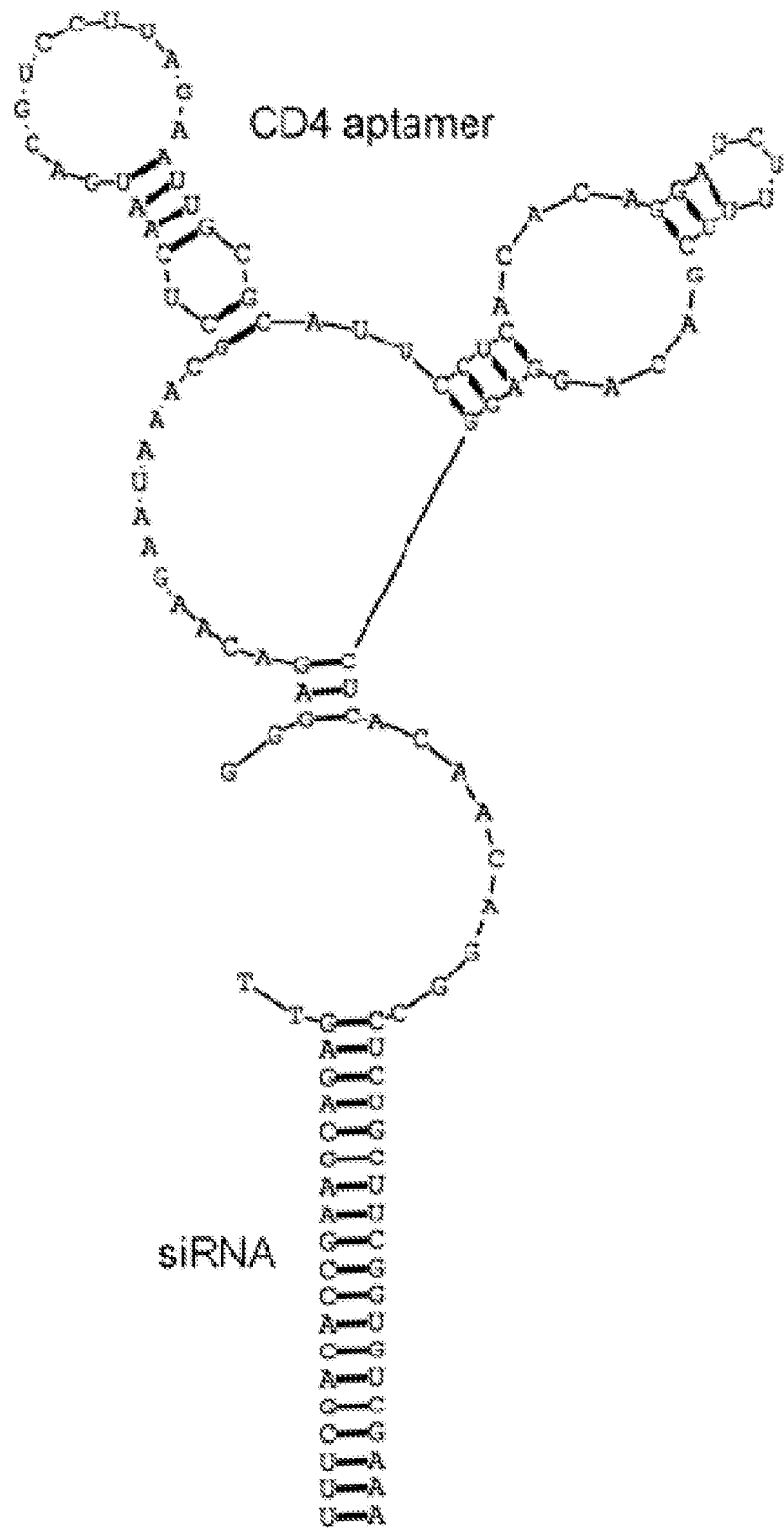
FIGS. 1A-1D show the internalization of Cy3-labeled CD4 aptamer-siRNA chimeras (CD4-AsiC) specifically by primary CD4+ cells.

The invention provides novel methods for delivering reagent into a cell, including a CD4+ T cell and a macrophage. The invention further provides methods for inhibiting, preventing and treating HIV infection using the novel methods of reagent delivery disclosed herein. Because delivery of reagents, e.g. small molecules, nucleic acids, peptides and proteins, to CD4+ cells is difficult, the conjugates described herein can be used for delivery of such reagents to CD4+ cells.

In one aspect, the invention provides a conjugate comprising an aptamer and a modulator, wherein the aptamer and the modulator are linked to each other by a linker. As used herein, the term "modulator" refers to a molecule that is to be delivered into a cell. Without limitations, modulator includes, but is not limited to, small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, or animal cells; naturally occurring or synthetic compositions; and any combinations thereof. While, not necessary, a modulator can have biological activity.

In some embodiments of the aspects described herein, the modulator is a gene modulator. As used herein, the term "gene modulator" refers to an oligonucleitde that can modulate (e.g. inhibit) the expression of a target gene gene. Without wishing to be bound by a theory, the gene modulator can modulate the expression of a target gene by any one of number of pathways including, but not limited to, RISC mediated cleavage (RNAi), RNAse H mediated cleavage, and steric blocking (antisense). Furthermore, a gene modulator can be single-stranded, double stranded, or partially double-stranded. Moreover, a gene modulator can also have a hairpin structure. Exemplary gene modulator include, but are not limited to, siRNAs, antisense oligonucleotides, microRNAs, pre-microRNAs, ribozymes, and analogs and derivatives thereof.

In some embodiments, the gene modulator inhibits the expression of an endogenous gene, a transgene, or an exogenous gene. In some embodiments, the gene modulator inhibits the expression of viral gene, a cellular gene required for virus replication and/or infection, and/or a cellular gene required for viral function.

As used herein, the term "gene modulator" also includes nucleic acids, e.g. RNAs, that can induce exogenous expression of a polypeptide, e.g. a protein, of interest in a cell. Accordingly, in some embodiments, the gene modulator is a mRNA that encodes for a polypeptide of interest. Without wishing to be bound by a theory, the ability to direct exogenous expression of a protein of interest is useful, for example, in the treatment of disorders caused by an endogenous genetic defect in a cell that impairs or prevents the ability of that cell to produce the protein of interest. Accordingly, in some embodiments, compositions and methods comprising the aptamer-gene modulator described herein can be used for the purposes of gene therapy.

Recently, Warren, L. et al. (Cell Stem Cell, 2010, 7: 618-63, content of which is herein incorporated by reference in its entirety) disclosed methods of producing induced pluripotent stem cells (iPSCs) and directed differentiation of iPSCs with synthetic modified mRNAs. Accordingly, in some embodiments, the gene modulator is a mRNA that encodes for a factor selected from the group consisting of OCT4, SOX1, SOX 2, SOX 3, SOX15, SOX 18, NANOG, KLF1, KLF 2, KLF 4, KLF 5, NR5A2, c-MYC, l-MYC, n-MYC, REM2, TERT, LIN28, MYOD, and any combinations thereof. Other mRNAs amenable for conjugation with aptamers include, for example, those described in U.S. Prov. App. No. 61/387,220, filed Sep. 28, 2010, content of which is herein incorporated by reference in its entirety. Without limitations, the mRNA can be delivered to any cell including those described in U.S. Prov. App. No. 61/387,220.

The conjugated mRNA can comprise one or more oligonucleotide modifications described herein. For example, the conjugated mRNA can comprise an oligonucleotide modification selected from the group consisting of internucleotide linkage modification, sugar modification, nucleohase modification, and any combinations thereof.

In some embodiments the conjugated mRNA comprises at least two modified nucleosides. In one such embodiment, the two modified nucleosides are selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2'deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2, N2, 7-trimethylguanosine (m2,2,7G), and inosine (I). In one such embodiment, the at least two modified nucleosides are 5-methylcytidine (5mC) and pseudouridine.

In some embodiments, the conjugated mRNA further comprises a poly(A) tail, a Kozak sequence, a 3' untranslated region, a 5' untranslated region, or any combination thereof. In one embodiment, the poly(A) tail, the Kozak sequence, the 3' untranslated region, the 5' untranslated region, or the any combination thereof comprises one or more of oligonucleotide modifications described herein.

In some embodiments, one end of the aptamer comprises a poly(dT) or a poly(U) sequence and the poly(A) tail of the mRNA can hybridize with the poly(dT) or the poly(U) sequence. Without limitations, the poly(dT) or the poly(U) can be linked directly, e.g. by a phosphodiester or a modified intersugar linkage, or indirectly by a linker described herein.

Linkers

As used herein, the term "linker" means a moiety that connects two parts of a compound. Linkers typically comprise a direct bond or an atom such as oxygen or sulfur, a unit such as NH, C(O), C(O)O, C(O)NH, S, SS, SO, $SO_2$, $SO_2NH$, P(O)(O—), or a chain of atoms. In some embodiments, the aptamer and the gene modulator are linked by a phosphodiester or a modified intersugar linkage described herein.

In some embodiments, the linker between the aptamer and the gene modulator is a nucleotidic linker. As used herein, a "nucleotidic linker" refers to an oligonucleotide that connects an aptamer to an oligonucleotide agent. Without limitations, the nucicotidic linker can be single-stranded or a double-stranded oligonucleotide, e.g., a linker comprising a first oligonucleotide strand and second oligonucleotide strand, wherein the first and the second strands are sufficiently complementary to each other. Furthermore, the nucleotidic linker can comprise one or more of the oligonucleotide modifications described herein. In some embodiments, the nucleotidic linker is linked to the aptamer and the gene modulator by a phosphodiester linkage or by an intersugar linkage modification described herein.

The skilled artisan recognizes that when the linkage between two oligonucleotides is a phosphodiester linkage or a modified intersugar linkage, modification the two oligonucleotides together can be considered as one oligonucleotide comprising the nucleotide sequences of the two oligonucleotides.

For a single-stranded nucleotidic linker, the aptamer can be at the 5'-end or the 3'-end of the linker. For a double-stranded nucleotidic linker, the aptamer and the gene modulator can be linked to different strands of the linker. Furthermore, the aptamer and the gene modulator can be at the 5'-end or the 3'-end of the strand they are linked to. In some embodiments, both the aptamer and the gene modulator are at the 5'-end of the strand to which they are linked. In some other embodiments, both the aptamer and the gene modulator are at the 5'-end of the strand to which they are linked. In yet some other embodiments, one of the aptamer and the gene modulator is at the 5'-end and the other is at the 3'-end of the strand to which they are which they are linked.

The nucleotidic linker can itself be linked by a non-nucleotidic linker to the oligonucleotide agent and/or the aptamer. Without limitations, a non-nucleotidic linker can be linked to the aptamer, the gene modulator and/or a nucleotidic linker by a phosphodiester linkage or an oligonucleotide intersugar modification described herein.

In some embodiments, the nucleotidic linker is linked to the gene modulator by a non-nucleotidic linker, and the nucleotidic linker is not linked to the aptamer by a non-nucleotidic linker. In some further embodiments of this, the nucleotidic linker is linked to the gene modulator by a non-nucleotidic linker, and the nucleotidic linker is linked to the aptamer by a phosphodiester linkage or an oligonucleotide intersugar modification described herein.

A nucleotidic linker can be of any length, e.g., between 4-30 nucleotides in length. A double-stranded linker can comprise between 5-30 nucleotide basepairs, in some embodiments, 5-20 or 4-20, 5-15, or 4-15 bp linker is used. Accordingly, in some embodiments the double-stranded linker comprises 5, 6, 7, 8, 9, 10, 11, 12, 13, 14, 15, 16, 17, 18, 19, or 20 nucleotide base pairs.

In some embodiments, one of strand of the double-stranded linker is extended at the 3'- and/or the 5'-end by 1-4 nucleotides which do not base pair with a nucleotide on the other strand.

While, the nucleotidic linker can comprise any sequence, in some embodiments, the GC content of the linker comprises 30-80%, e.g., about 30%, about 35%, about 40%, about 45%, about 50%, about 55%, about 60%, about 65%, about 70%, about 75% or about 80%, GC content. Without wishing to be bound by a theory, a higher GC content in a double-stranded oligonucleotide leads to a higher thermal stability of the double stranded oligonucleotide and is thus desirable in some embodiments.

In some embodiments, the nucleotidic linker is single stranded and comprises the sequence (X)n, wherein X is modified or unmodified deoxy or ribose nucleotide and n is 1-20. In some embodiments, X is selected from the group consisting of A, G, C, U, dA, dG, dC, and dT.

In some embodiments, the nucleotidic linker is double stranded and comprises the nucleotide sequence SEQ ID NO: 72 (5'-CAACAGGC-3') and complementary sequence SEQ ID NO: 73 (5'-(X)$_{n1}$GCCUGUUG-3', wherein X is a modified or unmodified nucleotide and n is 0-4). In some further embodiments of this, X is U and n is 1, i.e. SEQ ID NO: 74 (5'-UGCCUGUUG-3').

In some embodiments, the double-stranded linker has a melting temperature ($T_m$) of 25° C. to 95° C. Preferably, the melting temperature is such as to allow the double-stranded linker to remain significantly double-stranded under physiological conditions. As used herein, "physiological conditions" refers to temperature, pH, ionic strength, viscosity, and like biochemical parameters which are compatible with a viable organism, and/or which typically exist intracellularly in a viable cultured cell or a mammalian cell. In general, in vitro physiological conditions comprise 50-200 mM NaCl or KCl, pH 6.5-8.5, 20-45° C. and 0.001-10 mM divalent cation (e.g., $Mg^{2+}$, $Ca^{2+}$); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or anti-foam agents and/or scintillants. Accordingly, in some embodiments, at least 50%, at least 55%, at least 60%, at least 65%, at least 70%, at least 75%, at least 80%, at least 85%, at least 90%, or at least 95% of the double-stranded linker remains double-stranded under physiological conditions.

In some embodiments, the aptamer and the gene modulator can be linked by a phosphodiester linkage or an oligonucleotide intersugar linkage modification described herein. Similarly, a linker can be linked to the aptamer and/or the gene modulator by a phosphodiester linkage or an oligonucleotide intersugar linkage modification described herein.

9, In some embodiments, the linkage between the aptamer and the gene modulator is by formation of an oligonucleotide double-stranded structure. For example, the gene modulator can comprise a nucleotide sequence which is complementary with and can base pair with the aptamer sequence. The complementary sequence can be of any length that allows formation of a stable double-stranded structure under physiological conditions. Thus, a complementary sequence can have a length from 5 to full length of the aptamer. For example, a complementary sequence can be 5, 6, 7, 8, 10, 11, 12, 13, 14, 15, 16, 17, 18, 19, 20, or more nucleotides in length. It is not necessary for the complementary sequence to be fully complementary with the aptamer sequence. For example, the 5' or 3' end of the complementary sequence can comprise 1-5 (e.g., 1, 2, 3, 4 or 5) nucleotides which are not complementary with the aptamer sequence.

Additionally, it also to be understood that the complementary sequence only needs to bind with a part of the aptamer sequence and does not need to bind over the full length of the aptamer sequence. Thus, the double-stranded structure formed by binding of the complementary sequence with the aptamer can comprise any number of base pairs including the nucleotide length of the apatamer. In some embodiments, the double-stranded structure formed by binding of the complementary sequence with the aptamer can comprise 5, 6, 7, 8, 9, 10, 11, 12, 13, 14, 15, 16, 17, 18, 19, 20 or more nucleotide base pairs.

In some embodiments, the gene modulator comprises a nucleotide sequence which is complementary and can base pair with a sequence in the 5' or 3' terminal region of the aptamer sequence. In some embodiments, the complementary sequence can base pair with the last 5, 6, 7, 8, 9, 11, 12, 13, 14, 15, 16, 17, 18, 19, 20 nucleotides at the 5' or 3' end of the apatamer.

The complementary sequence which can bind with the aptamer can be part of the gene modulator and present on the 5' or 3' end of the gene modulator. In some embodiments, the complementary sequence which can bind with the aptamer can be linked to the 5' or 3' end of the gene modulator by a linker described herein. In some embodiments, the complementary nucleotide sequence is linked to the gene modulator by a non-nucleotidic linker.

In some embodiments, the complementary sequence comprises a nucleotide sequence which is complementary with the last 15, 14, 13, 12, 11, 10, 9, 8, 7, 6, 5, 4, or 3 nucleotides at the 5' or 3' end of the aptamer. In some embodiments, the complementary sequence comprises the nucleotide sequence SEQ ID NO: 75 (5'-U-(3C)-UGC CUG UUG-3', wherein 3C is a 3-carbon linker, such as —OCH$_2$CH$_2$CH$_2$O—).

When the gene modulator is double stranded, the complementary sequence which can bind with the aptamer can be linked at the 5' or 3' end of either strand (e.g., sense or anti sense strand of an siRNA) of the gene modulator. In some embodiments, the complementary sequence which can bind with the aptamer is linked to the 5' or 3' end of a sense strand of a siRNA. In one embodiment, the complementary nucleotide sequence which can bind with the aptamer is bound to the 5' end of a sense strand of a siRNA by a non-nucleotidic linker described herein.

In some embodiments, the linker between the aptamer and the gene modulator is a non-nucleotidic linker. As used herein, the term "non-nucleotidic" refers to a linker that does not include nucleotides or nucleotide analogs. Typically, non-nucicotidic linkers comprise an atom such as oxygen or sulfur, a unit such as NR$^1$, C(O), C(O)NH, SO, SO$_2$, SO$_2$NH, or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkynyl, alkylheteroarylalkynyl, alkenylheteroarylalkyl, alkenylheteroarylalkenyl, alkcnylhctcroarylalkynyl, alkynylhctcroarylalkyl, alkynylheteroarylalkcnyl, alkynylhctcroarylalkynyl, alkylheterocyclylalkyl, alkylheterocyclylalkenyl, alkylhererocyclylalkynyl, alkenylheterocyclylalkyl, alkenylheterocyclylalkenyl, al kenyl heterocycl yl alkynyl, alkynylheterocycl yl alkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, SS, S(O), SO$_2$, N(R$^1$)$_2$, NR', C(O), C(O)O, C(O)NH, —OPO$_2$O—, cleavable linking group, substituted or unsubstituted aryl, substituted or unsubstituted heteroaryl, substituted or unsubstituted heterocyclic; where R$^1$ is hydrogen, acyl, aliphatic or substituted aliphatic.

In some embodiments, the non-nucleotidic linker is a C3-Cioalkyl, which can be optionally substituted. In some embodiments, at least one methylene in the C3-Cioalkyl is replaced by a O, S, SS, S(O), SO2, NH, C(O), C(O)O, or C(O)NH.

In some embodiments, the non-nucleotidic linker is —OCH$_2$CH$_2$CH$_2$O—.

In some embodiments, the non-nucleotidic linker is —CILCILCII,

Without limitations, a non-nucicotidic linker can be linked to the aptamer, the nucicotidic linker or the gene modulator by a phosphodiester linkage and/or a modified intersugar linkage described herein.

In some embodiments, there are multiple, e.g., 2, 3, 4, 5, 6, 7, 8, 9, 10 or more non-nucleotidic linkers between the two moieties being connected. For example, there can be 2, 3, 2, 3, 4, 5, 6, 7, 8, 9, 10 or more non-nucleotidic linkers between the aptamer and the oligonucleotide agent, between the aptamer and the nucicotidic linker, and/or the oligonucicotide agent and the nucicotidic linker. When multiple non-nucleotidic linkers are present, all of them can be the same, each of them can be different, some can be same and others different, and any combinations thereof. The non-nucleotidic linkers can be linked to each other by a phosphodiester linkage and/or a modified intersugar linkage described herein.

In some embodiments, the non-nucleotidic linker comprises at least one cleavable linking group, i.e. the linker is a cleavable linker. As used herein, a "cleavable linker" refers to linkers that are capable of cleavage under various conditions. Conditions suitable for cleavage can include, but are not limited to, pH, UV irradiation, enzymatic activity, temperature, hydrolysis, elimination and substitution reactions, redox reactions, and thermodynamic properties of the linkage. In some embodiments, a cleavable linker can be used to release the linked components after transport to the desired target. The intended nature of the conjugation or coupling interaction, or the desired biological effect, will determine the choice of linker group.

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis. Linkers that contain peptide bonds can be used when targeting cell types rich in peptidases, such as liver cells and synoviocytes.

In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions)

Exemplary cleavable linking groups include, but are not limited to, redox cleavable linking groups (e.g., —S—S— and —C(R)$_2$—S—S—, wherein R is H or C$_1$-C$_6$ alkyl and at least one R is C1-C6 alkyl such as CH$_3$ or CH$_2$CH$_3$); phosphate-based cleavable linking groups (e.g., —O—P(O)(OH)—O—); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells. A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleavable in an acidic environment with a pH of about 6.5 or lower (e.g., about 6.0, 5.5, 5.0, or lower), or by agents such as enzymes that can act as a general acid.

In some embodiments, the aptamer and the gene modulator is inked by a double-stranded oligonucleotide linker comprising a first oligonucleotide strand and a second oligonucleotide strand, the first strand is linked to the aptamer and the second strand is linked to the gene modulator, the the second strand and the gene modulator are linked by a non-nucleotidic linker.

siRNAs

The skilled artisan is well aware that double-stranded oligonucleotides comprising a duplex structure of between 20 and 23, but specifically 21, base pairs have been hailed as particularly effective in inducing RNA interference (Elbashir et al., EMBO 2001, 20:6877-6888). However, others have found that shorter or longer double-stranded oligonucleotides can be effective as well. Oligonucleotides that are effective in inducing RNA interference are also referred to as siRNA, RNAi agent, or iRNA agent, herein. These RNA interference inducing oligonucleotides associate with a cytoplasmic multi-protein complex known as RNAi-induced silencing complex (RISC).

These double-stranded oligonucleotides comprise two oligonucleotide strands that are sufficiently complementary to hybridize to form a duplex structure. Generally, the duplex structure is between 15 and 30, more generally between 18 and 25, yet more generally between 19 and 24, and most generally between 19 and 21 base pairs in length. In some embodiments, longer double-stranded oligonucleotides of between 25 and 30 base pairs in length are preferred. In some embodiments, shorter double-stranded oligonucleotides of between 10 and 15 base pairs in length are preferred. In another embodiment, the double-stranded oligonucleotide is at least 21 nucleotides long.

In some embodiments, the siRNA comprises a sense strand and an antisense strand, wherein the antisense RNA strand has a region of complementarity which is complementary to at least a part of a target sequence, and the duplex region is 14-30 nucleotides in length. Similarly, the region of complementarity to the target sequence is between 14 and 30, more generally between 18 and 25, yet more generally between 19 and 24, and most generally between 19 and 22 nucleotides in length.

The phrase "antisense strand" as used herein, refers to an oligonucleotide that is substantially or 100% complementary to a target sequence of interest. The phrase "antisense strand" includes the antisense region of both oligonucleotides that are formed from two separate strands, as well as unimolecular oligonucleotides that are capable of forming hairpin or dumbbell type structures. The terms "antisense strand" and "guide strand" are used interchangeably herein.

The phrase "sense strand" refers to an oligonucleotide that has the same nucleoside sequence, in whole or in part, as a target sequence such as a messenger RNA or a sequence of DNA. The terms "sense strand" and "passenger strand" are used interchangeably herein.

By "specifically hybridizable" and "complementary" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, *CSH Symp. Quant. Biol.* LII pp. 123-133; Frier et al., 1986, *Proc. Nat. Acad. Sci.* USA 83:9373-9377; Turner et al., 1987, *J. Am. Chetn. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarily" refers to polynucleotide strands exhibiting 90% or greater complementarity, excluding regions of the polynucicotide strands, such as overhangs, that arc selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

In some embodiments, the siRNA modulates the expression of a target gene via RISC mediated cleavage of the target sequence.

In many embodiments, the siRNA is sufficiently large that it can be cleaved by an endogenous molecule, e.g., by Dicer, to produce smaller siRNA molecule that can enter the RISC machinery.

In some other embodiments, the siRNA is not a substrate for an endogenous molecule, e.g. Dicer. For clarification, while the conjugate itself can be processed by an endogenous molecule, e.g. dicer, the siRNA part of the conjugate itself may not undergo processing by an endogenous molecule. Thus, the endogenous molecule can cleave the conjugate at position that is outside of the siRNA part, e.g., at the linker linking the siRNA to the aptamer and/or the nucleotidic linker, within the nucleotidic linker, within the aptamer, etc.

In some embodiments, the double-stranded region of the siRNA is equal to or at least 10, 11, 12, 13, 14, 15, 16, 17, 18, 19, 20, 21, 22, 23, 23, 24, 25, 26, 27, 28, 29, or 30 nucleotide basepairs in length.

In some embodiments, the antisense strand of the siRNA is equal to or at least 14, 15, 16, 17, 18, 19, 20, 21, 22, 23, 23, 24, 25, 26, 27, 28, 29, or 30 nucleotides in length.

In some embodiments, the sense strand of the siRNA is equal to or at least 10, 11, 12, 13, 14, 15, 16, 17, 18, 19, 20, 21, 22, 23, 23, 24, 25, 26, 27, 28, 29, or 30 nucleotides in length.

In some embodiments, one strand of the siRNA has at least one stretch of 1-5 single-stranded nucleotides in the double-stranded region. By "stretch of single-stranded nucleotides in the double-stranded region" is meant that there is present at least one nucleotide basepair at both ends of the single-stranded stretch. In some embodiments, both strands have at least one stretch of 1-5 (e.g., 1, 2, 3, 4, or 5) single-stranded nucleotides in the double stranded region. When both strands have a stretch of 1-5 (e.g., 1, 2, 3, 4, or 5) single-stranded nucleotides in the double stranded region, such single-stranded nucleotides can be opposite to each other (e.g., a stretch of mismatches) or they can be located such that the second strand has no single-stranded nucleotides opposite to the single-stranded oligonucleotides of the first strand and vice versa (e.g., a single-stranded loop). In some embodiments, the single-stranded nucleotides are present within 8 nucleotides from either end, for example 8, 7, 6, 5, 4, 3, or 2 nucleotide from either the 5' or 3' end of the region of complementarity between the two strands.

An siRNA having at least one single-stranded nucleotide overhang has unexpectedly superior inhibitory properties than its blunt-ended counterparts. As used herein, the term "overhang" refers to a double-stranded structure where at least one end of one strand is longer than the corresponding end of the other strand forming the double-stranded structure. Generally, the single-stranded overhang is located at the 3'-terminal end of the antisense strand or, alternatively, at the 3'-terminal end of the sense strand. The double-stranded oligonucleotide can also have a blunt end, generally located at the 5'-end of the antisense strand. Generally, the antisense strand of the siRNA has a single-stranded overhang at the 3'-end, and the 5'-end is blunt. A siRNA strand having a single stranded region between the siRNA double-stranded region and the non-nucleotidic linker is considered a single-stranded overhang herein.

Accordingly, in some embodiments, at least one end of the siRNA has a single-stranded nucleotide overhang of 1 to 4, generally 1 or 2 nucleotides. In some embodiment, both ends of the siRNA have a single-stranded nucleotide overhang of 1 to 4, generally 1 or 2 nucleotides.

In some embodiments it is particularly preferred, e.g., to enhance stability, to include particular nucleobases in the single-stranded overhangs, or to include modified nucleotides or nucleotide surrogates, in single-strand overhangs. For example, it can be desirable to include purine nucleotides in overhangs. In some embodiments all or some of the bases in the single strand overhang will be modified, e.g., with a modification described herein. Modifications in the single-stranded overhangs can include, e.g., the use of modifications at the 2' OH group of the ribose sugar, e.g., the use of dcoxyribonucicotides, e.g., dcoxythymidine, instead of ribonucicotides, and modifications in the phosphate group, e.g., phosphothioate modifications. Overhangs need not be homologous with the target sequence. In some embodiments, the single strand overhangs are asymmetrically modified with a modification described herein, e.g. a first single stand overhang comprises a modification that is not present in a second single strand overhang. In some embodiments, the overhang comprises at least one 5'-5', 3'-3', 3'-2', 2'-5', 2'-3' or 2'-2' intersugar linkage. In some embodiments, the single stranded overhang is linked via a 3'-3', 3'-2', 2'-5', 2'-3' or 2'-2' intersugar linkage to the rest of the oligonucleotide.

In some embodiments, the antisense strand of the siRNA has 1-10 nucleotide single-stranded overhang at each of the 3' end and the 5' end over the sense strand. In another embodiment, the sense strand of the siRNA has 1-10 nucleotide single-stranded overhang at each of the 3' end and the 5' end over the antisense strand.

The antisense strand of the siRNA can contain one or more mismatches to the target sequence. In a preferred embodiment, the antisense strand contains no more than 3 mismatches. If the antisense strand contains mismatches to a target sequence, it is preferable that the area of mismatch not be located in the center of the region of complementarity between the antisense strand and the target sequence. If the antisense strand contains mismatches to the target sequence, it is preferable that the mismatch is restricted to 5 nucleotides from either end, for example 5, 4, 3, 2, or 1 nucleotide from either the 5' or 3' end of the region of complementarity between the antisense strand and the target sequence. Methods known in the art can be used to determine whether a siRNA containing a mismatch to a target sequence is effective in inhibiting the expression of the target gene.

In some embodiment, the sense-strand comprises a mismatch to the antisense strand. In some embodiments, the sense strand comprises no more than 1, 2, 3, 4 or 5 mismatches to the antisense strand. In preferred embodiments, the sense strand comprises no more than 3 mismatches to the antisense strand.

The siRNAs of the invention can also target more than one RNA region by having each strand of the siRNA targeting a sequence or part thereof independently. For example, a siRNA can include a first and second sequence that are sufficiently complementary to each other to hybridize. The first sequence can be complementary to a first target sequence and the second sequence can be complementary to a second target sequence.

The first target sequence can be a first target gene and the second target sequence can be a second target gene, or the first and second target sequences can be different regions of a single target gene. The first and second target sequences can differ by at least 1 nucleotide.

The first and second target sequences can be transcripts encoded by first and second sequence variants, e.g., first and second alleles, of a gene. The sequence variants can be mutations, or polymorphisms, for example. The first target sequence can include a nucleotide substitution, insertion, or deletion relative to the second target sequence, or the second target sequence can be a mutant or variant of the first target sequence. The first and second target sequences can comprise viral or human genes. The first and second target sequences can also be on variant transcripts of an oncogene or include different mutations of a tumor suppressor gene transcript. In addition, the first and second target sequences can correspond to hot-spots for genetic variation.

An siRNA may cause unintended inhibition of gene expression of a non-target gene leading to off-target effects. As used herein, the term "off-target" and the phrase "off-target effects" refer to any instance in which a siRNA against a given target causes an unintended affect by interacting either directly or indirectly with another mRNA sequence, a DNA sequence or a cellular protein or other moiety. For example, an "off-target effect" may occur when there is a simultaneous degradation of other transcripts due to partial homology or complementarity between that other transcript and the sense and/or antisense strand of a siRNA. Alternatively, or in addition, an unwanted off-target effect can happen when the sense strand enters the RISC complex and reduces the gene expression of a complementary sequence which is not the desired target of the siRNA.

A number of strategies can be applied to reduce the off-target effects due to sense strand mediated RNA interference. The sense strand can be chemically modified so that it can no longer act in the RISC mediated cleavage of a target sequence. Without wishing to be bound by theory, such modifications minimize off-target RNAi effects due to sense strand.

In some embodiments, ends of siRNA can be modified so that the end corresponding to 5' end of sense strand has a higher thermal stability as compared to the end corresponding 3' end of sense strand, as described in U.S. Pat. No. 7,745,608, content of which is herein incorporated by reference. Without wishing to be bound by theory, this allows preferential incorporation of the antisense strand into the RISC complex and reduces off-target effects of sense strand.

Without limitations, the sense and/or the antisense can be linked to the aptamer and/or the linker. Furthermore, the sense strand and/or the antisense strand can be linked via its 5'- or 3'-end. Preferably, when the antisense strand is linked to the aptamer and/or the linker, it is linked by its 3'-end. Similarly, it is preferred that when the sense strand is linked to the aptamer and/or the linker, it is linked by its 5'-end.

In some embodiments, the siRNA comprises a nucleotide sequence shown in Table 3.

In some embodiments, the siRNA comprises a nucleic acid modification selected from the group consisting of internucleotide linkage modification (intersugar linkage modification), sugar modification, nucleobase modification, and any combinations thereof. Specific nucleic modifications are described below.

In some embodiments, the antisense strand and/or the sense strand comprises at least one purine (e.g., 1, 2, 3, 4, 5, 6, 7, 8, 9, 10 or more) with a 2'-OCH$_3$ sugar modification.

MicroRNAs

MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded—17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

MicroRNAs have also been implicated in modulation of pathogens in hosts. For example, see Jopling, C. L., et al., *Science* (2005) vol. 309, pp 1577-1581. Without wishing to be bound by theory, administration of a microRNA, and/or a pre-microRNA oligonucleotide, leads to modulation of pathogen viability, growth, development, and/or replication. In some embodiments, the gene modulator is a microRNA and or a pre-microRNA wherein the microRNA is a host microRNA. In some other embodiments, the gene modulator is a microRNA and or a pre-microRNA wherein the microRNA is a pathogen microRNA.

The number of miRNA sequences identified to date is large and growing, illustrative examples of which can be found, for example, in: "*miRBase: microRNA sequences, targets and gene nomenclature*" Griffiths-Jones S, Grocock R J, van Dongen S, Bateman A, Enright A J. NAR, 2006, 34, Database Issue, D140-D144; "The microRNA Registry" Griffiths-Jones S. NAR, 2004, 32, Database Issue, D109-D111; and also on the worldwide web at http://microrna.dot-.sanger.dot.ac.dot.uk/sequences/.

Ribozymes

Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, content of each of which is herein incorporated by reference, and synthesized to be tested in vitro and in vivo, as described therein.

Aptamers

Aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997); Famulok, Curr. Opin. Struct. Biol. 9:324-9(1999); Hermann and Patel, Science 287:820-5 (2000); and U.S. Pat. Nos. 5,270,163; 7,776,836; 7,776,837; 7,785,779; and 7,795,009, content of all of which is herein incorporated by reference. Aptamers can be RNA or DNA based. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. However, in vivo selection of an aptamer is also possible. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target.

The aptamer can be linked to the siRNA and/or the linker by its 5'- or 3'-end. Accordingly, in one embodiment, the aptamer is linked by its 3'-end. Generally, an aptamer will be between about 30 to about 300 nucleotides in length. More commonly, an aptamer will be about 30 to about 130 nucleotides in length.

Without wishing to be bound by a theory, aptamers can direct cell-specific delivery of the conjugate into cell bearing the surface receptor the aptamer recognizes. Thus, in some embodiments, the aptamer binds to a cell surface receptor. In some embodiments, the aptamer is a CD4 aptamer. The term "CD4 aptamer" as used herein means that the aptamer recognizes and binds to a CD4 molecule. The CD4 molecule can be present freely or at a cell surface. In some embodiments, the aptamer comprises a nucleotide sequence shown in Table 1.

In some embodiments, the aptamer comprises a nucleic acid modification selected from the group consisting of internucleotide linkage modification, sugar modification, nucleobase modification, and any combinations thereof.

Gene Expression Modulation

As used herein the term "modulate gene expression" means that expression of the gene, or level of RNA molecule or equivalent RNA molecules encoding one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

As used herein, gene expression modulation happens when the expression of the gene, or level of RNA molecule or equivalent RNA molecules encoding one or more proteins or protein subunits is at least 5%, 10%, 20%, 30%, 40%, 50%, 60%, 70%, 80%, 90%, 100%, 2-fold, 3-fold, 4-fold, 5-fold or more different from that observed in the absence of the modulator. The % and/or fold difference can be calculated relative to the control or the non-control, for example, % difference=[expression with modulator-expression without modulator] / expression without modulator Or % difference=[expression with modulator-expression without modulator] / expression with modulator As used herein, the term "inhibit", "down-regulate", or "reduce", means that the expression of the gene, or level of RNA molecules or equivalent RNA molecules encoding one or more proteins or protein subunits, or activity of one or more proteins or protein subunits, is reduced below that observed in the absence of modulator. The gene expression is down-regulated when expression of the gene, level of RNA molecules or equivalent RNA molecules encoding one or more proteins or protein subunits, or activity of one or more proteins or protein subunits, or level of a protein or a protein subunit is reduced by at least 5% relative to a corresponding non-modulated control, and preferably at least 10%, 20%, 30%, 40%, 50%, 60%, 70%, 80%, 90%, 95%, 98%, 99% or most preferably, 100% (i.e., no gene expression).

The terms "increased", "increase" or "enhance" or "up-regulate" means that the expression of the gene, or level of RNA molecules or equivalent RNA molecules encoding one or more proteins or protein subunits, or activity of one or more proteins or protein subunits, is increased above that observed in the absence of modulator. The gene expression is up-regulated when expression of the gene, level of RNA molecules or equivalent RNA molecules encoding one or more proteins or protein subunits, or activity of one or more proteins or protein subunits, or level of a protein or a protein subunit is increased by at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

Gene expression can be measured by measuring the level of a nucleic acid (e.g., mRNA) or a protein or a subunit of a protein. Methods for measuring gene expression are well known in the art and available to the skilled artisan. Exemplary methods include, but are not limited to quantitative PCR, immunoblotting, ELISA, and such.

Target Genes

By "gene" or "target gene" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus.

By "target sequence" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant.

Target genes include genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a gene involved in cell proliferation, an oncogene, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, and a gene which mediates a neurological disease.

Exemplary target genes include, but are not limited to, CCR-5 gene; CD45 gene; TREX1 gene; lamin A gene; EG5 gene; FoxP3 gene; PD1; CTLA4; TREX1; T-bet; GATA3; Bcl6; ROR-gamma-t; PDGF beta gene; Erb-B gene, Src gene; CRK gene; GRB2 gene; RAS gene; MEKK gene; JNK gene; RAF gene; Erkl/2 gene; PCNA(p21) gene; MYB gene; c-MYC gene; JUN gene; FOS gene; BCL-2 gene; Cyclin D gene; VEGF gene; EGFR gene; Cyclin A gene; Cyclin E gene; WNT-1 gene; beta-catenin gene; c-MET gene; PKC gene; NFKB gene; STAT3 gene; survivin gene; Her2/Neu gene; topoisomerase I gene; topoisomerase II alpha gene; p73 gene; p21(WAF1/CIP1) gene; p27(KIP1) gene; PPM1D gene; caveolin I gene; MIB 1 gene; MTAI gene; M68 gene; tumor suppressor genes; p53 gene; DN-p63 gene; pRb tumor suppressor gene; APC1 tumor suppressor gene; BRCA1 tumor suppressor gene; PTEN tumor suppressor gene; MLL fusion genes, e.g., MLL-AF9, BCR/ABL fusion gene; TEL/AML1 fusion gene; EWS/FLI1 fusion gene; TLS/FI JS1 fusion gene; PAX3/FKHR fusion gene; AML1/ETO fusion gene; alpha v-integrin gene; Flt-1 receptor gene; tubulin gene; Human Papilloma Virus gene, a gene required for Human Papilloma Virus replication, Human Immunodeficiency Virus gene (HIV), a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, *plasmodium* gene, a gene that is required for *plasmodium* gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, 1-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCAT gene, SCA8 gene, and any combinations thereof.

In some embodiments, the target gene encodes a cellular protein required for HIV replication and/or infection and/or a cellular gene which mediates a HIV function. Such proteins include, e.g., CXCR4, CCR5, and CCR3. Genes encoding these proteins can be targeted using siRNAs based on sequences available in the public databases.

CXCR4, or fusin, which is expressed on T cells (Feng Y, et al. Science 1996 May 10; 272(5263):872-7.). Co-expression of CXCR4 and CD4 on a cell allow T-tropic HIV isolates to fuse with and infect the cell. HIV gp120 interacts with both CD4 and CXCR4 to adhere to the cell and to effect conformational changes in the gp120/gp41 complex that allow membrane fusion by gp41. CXCR4 is expressed on many T cells, but usually not on macrophages and does not allow fusion by macrophage-tropic (M-tropic) HIV isolates (Feng et al., 1996). It is interesting to note that stimulation with some bacterial cell wall products upregulates CXCR4 expression on macrophages and allows infection by T-tropic strains of HIV (Moriuchi M, et al. J Clin Invest 1998 Oct. 15; 102(8):1540-50.).

Shortly after the identification of CXCR4, another co-receptor was identified. CCR5, which is expressed on macrophages and on some populations of T cells, can also function in concert with CD4 to allow HIV membrane fusion (Deng H, et al., Nature 1996 Jun. 20; 381(6584):661-6; Dragic T, Nature 1996 Jun. 20; 381(6584):667-73; and Alkhatib G, et al., Science 1996 Jun. 28; 272(5270):1955-8.). HIV gp120 binding to CCR5 is CD4-dependent, as antibody inhibition of CD4 can reduce binding to CCR5 by 87% (Trkola A, et al., Nature 1996 Nov. 14; 384(6605):184-7.). M-tropic HIV isolates appear to use CCR5 as their co-receptor for infection both of macrophages and of some T cells.

CCR3, a chemokine expressed on eosinophils and microglia, is used by some strains of HIV for infection of the microglia and resulting CNS pathology (He J, et al., Nature 1997 Feb. 13; 385(6617):645-9.

Other such chemokine receptors can also bind HIV gp120 and be used for HIV entry, and are thus useful targets for siRNA therapy.

In some embodiments, the target gene encodes an HIV protein selected from the group consisting of gag, pol, env, tat, rev, vif, nef, vpr, vpu, vpx, and any combinations thereof.

In some embodiments, the target gene is an oncogene. As used herein, the term "oncogene" is used to mean a genetic sequence whose expression within a cell provides a function, including one of several functions, in the steps leading from a normal cell into a tumor cell. Oncogenes have been classified into three distinct groups: proto-oncogenes, tumour-suppressor genes, and stability genes, according to the biological roles they fulfil in a normal cell and hence, the aberrant process they effect in an oncogenic state. Exemplary oncogenes include, but are not limited to, growth factors or mitogens (e.g. c-Sis), receptor tyrosine kinase (e.g., epidermal growth factor receptor, platelet-derived growth factor receptor, vascular endothelial growth factor, and Her2.neu), cytoplasmic tyrosine kinases (e.g. Src-family, Syk-ZAP-70 family, BTK family of tyrosine kinases, and the Abl gene in CML-Philadelphia chromosome), Cytoplasmic Serine/threonine kinases and their regulatory subunits (e.g. Raf kinase and cyclin-dependent kinases), regulatory GTPases (e.g. Ras protein), and transcription factors (e.g. myc gene).

The aptamer-oligonucleotide agent conjugates and the methods described herein can be used to knock out any gene in CD4+ cells. Accordingly, the conjugates and/or the methods presented herein can be used to modulate immune responses orchestrated by CD4-phenotypes. For example, siRNAs targeting a given gene can be easily designed by utilizing publically available siRNA design algorithms and sequences available in public databases.

Oligonucleotides

While, the following are discussed in reference to oligonucleotides, it is to be understood that the term oligonucleotide comprises aptamers, siRNAs, microRNAs, pre-microRNAs, and the nucicotidic linkers. As used herein, the term "oligonucicotide" refers to a polymer or oligomer of nucleotide or nucleoside monomers consisting of naturally occurring bases, sugars and intersugar linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Unmodified oligonucleotides can be less than optimal in some applications, e.g., unmodified oligonucleotides can be prone to degradation by e.g., cellular nucleases. However, chemical modifications to one or more of the subunits of oligonucleotide can confer improved properties, e.g., can render oligonucleotides more stable to nucleases; enhance in vivo half-life in blood, serum, other body fluids, and within cells; etc. Typical oligonucleotide modifications can include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the 2' hydroxyl on the ribose sugar; (iii) wholesale replacement of the phosphate moiety with "dephospho" linkers; (iv) modification or replacement of a naturally occurring base with a non-natural base; (v) replacement or modification of the ribose-phosphate backbone, e.g. peptide nucleic acid (PNA); (vi) modification of the 3' end or 5' end of the oligonucleotide, e.g., removal, modification or replacement of a terminal phosphate group or conjugation of a moiety, e.g., conjugation of a ligand, to either the 3' or 5' end of oligonucleotide; and (vii) modification of the sugar, e.g., six membered rings.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule. As described below, modifications, e.g., those described herein, can be provided as asymmetrical modifications.

A modification described herein can be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein. Accordingly, the aptamer-gene modulator conjugates can comprise any oligonucleotide modification described herein.

In certain instances, it can be desirable to modify one or both strands of a double-stranded oligonucleotide. In some cases, the two strands will include different modifications. In other instances, multiple different modifications can be included on each of the strands. The various modifications on a given strand can differ from each other, and can also differ from the various modifications on other strands. For example, one strand can have a modification, e.g., a modification described herein, and a different strand can have a different modification, e.g., a different modification described herein. In other cases, one strand can have two or more different modifications, and the another strand can include a modification that differs from the at least two modifications on the first strand.

The phosphate group in the intersugar linkage can be modified by replacing one of the oxygens with a different substituent. One result of this modification to the phosphodiester intersugar linkages can be increased resistance of the oligonucleotide to nucleolytic breakdown. Examples of modified phosphate groups include phosphorothioate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the intersugar linkage can be replaced by any of the following: S, Se, BR$_3$ (R is hydrogen, alkyl, aryl), C (i.e. an alkyl group, an aryl group, etc. . . . ), H, NR$_2$ (R is hydrogen, optionally substituted alkyl, aryl), or OR (R is optionally substituted alkyl or aryl). The phosphorous atom in an unmodified phosphate group is achiral. However, replacement of one of the non-bridging oxygens with one of the above atoms or groups of atoms renders the phosphorous atom chiral; in other words, a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligonucleotides diastereomers. Thus, while not wishing to be bound by theory, modifications to both non-bridging oxygens, which eliminate the chiral center, e.g. phosphorodithioate formation, can be desirable in that they cannot produce diastereomer mixtures. Thus, the non-bridging oxygens can be independently any one of O, S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either one of the linking oxygens or at both linking oxygens. When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as "non-phosphodiester intersugar linkage" or "non-phosphodiester linker".

The preparation of phosphinate oligonucleotides is described in U.S. Pat. No. 5,508,270. The preparation of alkyl phosphonate oligonucleotides is described in U.S. Pat. No. 4,469,863. The preparation of phosphoramidate oligonucleotides is described in U.S. Pat. No. 5,256,775 or 5,366,878. The preparation of phosphotriester oligonucleotides is described in U.S. Pat. No. 5,023,243. The preparation of boranophosphate oligonucleotide is described in U.S. Pat. Nos. 5,130,302 and 5,177,198. The preparation of 3'-Deoxy-3'-amino phosphoramidate oligonucleotides is described in U.S. Pat. No. 5,476,925. 3'-Deoxy-3'-methylenephosphonate oligonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

The intersugar phosphate group can be replaced by non-phosphorus containing connectors, e.g. dephospho linkers. Dephospho linkers are also referred to as non-phosphodiester linkers herein. While not wishing to be bound by theory, it is believed that since the charged phosphodicster group is the reaction center in nucicolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include, but are not limited to, amides (for example amide-3 (3'-CH$_2$—C(=O)—N(H)-5') and amide-4 (3'-CH$_2$—N(H)—C(=O)-5')), hydroxylamino, siloxane (dialkylsiloxxane), carboxamide, carbonate, carboxymethyl, carbamate, carboxylate ester, thioether, ethylene oxide linker, sulfide, sulfonate, sulfonamide, sulfonate ester, thioformacetal (3'-S—CF$_2$—O-5'), formacetal (3'-O—CH$_2$—O-5'), oxime, methyleneimino, methykenecarbonylamino, methylenemethylimino (MMI, 3'-CH$_2$—N(CH$_3$)—O-5'), methylenehydrazo, methylenedimethylhydrazo, methyleneoxymethylimino, ethers (C3'-O-05'), thioethers (C3'-S-05'), thioacetamido (C3'-N(H)—C(=O)—CH$_2$—S-05', C3'-O—P(O)—O—SS-05', C3'-CH$_2$—NH—NH-05', 3'-NHP(O)(OCH$_3$)—O-5' and 3'-NHP(O)(OCH$_3$)—O-5' and nonionic linkages containing mixed N, O, S and CH$_2$ component parts. See for example, Carbohydrate Modifications in Antisense Research; Y. S. Sanghvi and P. D. Cook Eds. ACS Symposium Series 580; Chapters 3 and 4, (pp. 40-65). Preferred embodiments include methylenemethylimino (MMI), methylenecarbonylamino, amides, carbamate and ethylene oxide linker.

One skilled in the art is well aware that in certain instances replacement of a non-bridging oxygen can lead to enhanced cleavage of the intersugar linkage by the neighboring 2'-OH, thus in many instances, a modification of a non-bridging oxygen can necessitate modification of 2'-OH, e.g., a modification that does not participate in cleavage of the neighboring intersugar linkage, e.g., arabinose sugar, 2'-O-alkyl, 2'-F, LNA and ENA.

Preferred non-phosphodiester intersugar linkages include phosphorothioates, phosphorothioates with an at least 1%, 5%, 10%, 20%, 30%, 40%, 50%, 60%, 70%, 80%, 90% 95% or more enantiomeric excess of Sp isomer, phosphorothioates with an at least 1%, 5%, 10%, 20%, 30%, 40%, 50%, 60%, 70%, 80%, 90% 95% or more enantiomeric excess of Rp isomer, phosphorodithioates, phsophotriesters, aminoalkylphosphotriesters, alkyl-phosphonates (e.g., methyl-phosphonate), selenophosphates, phosphoramidates (e.g., N-alkylphosphoramidate), and boranophosphonates.

Methylenemethylimino linked oligonucleosides, also identified herein as MMI linked oligonucleosides, methylenedimethylhydrazo linked oligonucleosides, also identified herein as MDH linked oligonucleosides, and methylenecarbonylamino linked oligonucleosides, also identified herein as amide-3 linked oligonucleosides, and methyleneaminocarbonyl linked oligonucleosides, also identified herein as amide-4 linked oligonucleosides as well as mixed intersugar linkage compounds having, as for instance, alternating MMI and PO or PS linkages can be prepared as is described in U.S. Pat. Nos. 5,378,825, 5,386,023, 5,489,677 and in Int. Pat. App. Pub. Nos. WO1992/20822 and WO1992/20823, content of all of which is herein incorporated by reference. Formacetal and thioformacetal linked oligonucleosides can be prepared as is described in U.S. Pat. Nos. 5,264,562 and 5,264,564. Ethylene oxide linked oligonucleosides can be prepared as is described in U.S. Pat. No. 5,223,618. Siloxane replacements are described in Cormier, J. F. et al. Nucleic Acids Res. 1988, 16, 4583. Carbonate replacements are described in Tittensor, J. R. J. Chem. Soc. C 1971, 1933. Carboxymethyl replacements are described in Edge, M. D. et al. J. Chem. Soc. Perkin Trans. 1 1972, 1991. Carbamate replacements are described in Stirchak, E. P. Nucleic Acids Res. 1989, 17, 6129.

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine, peptide nucleic acid (PNA), aminoethylglycyl PNA (aegPNA) and backnone-extended pyrrolidine PNA (bepPNA) nucleoside surrogates. A preferred surrogate is a PNA surrogate.

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They can also be prepared in accordance with U.S. Pat. No. 5,539,083.

An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O($CH_2CH_2O$)$_n$$CH_2CH_2$OR, n=1-50; "locked" nucleic acids (LNA) in which the oxygen at the 2' position is connected by ($CH_2$), wherein n=1-4, to the 4' carbon of the same ribose sugar, preferably n is 1 (LNA) or 2 (ENA); 0-AMINE or O—($CH_2$)$_n$AMINE (n=1-10, AMINE=$NH_2$; alkylamino, dialkylamino, heterocyclyl, arylamino, diaryl amino, heteroaryl amino, diheteroaryl amino, ethylene diamine or polyamino); and O—$CH_2CH_2$(N$CH_2CH_2$N$Me_2$)$_2$.

"Deoxy" modifications include halo (e.g., fluoro); amino (e.g. $NH_2$; alkylamino, di alkyl amino, heterocyclyl, aryl amino, diary] amino, heteroaryl amino, diheteroaryl amino, or amino acid); NH($CH_2CH_2$NH)$_n$$CH_2CH_2$-AMINE (AMINE=$NH_2$; alkylamino, dialkylamino, heterocyclyl, arylamino, diaryl amino, heteroaryl amino, or diheteroaryl amino); —NHC(O)R (R=alkyl, cycloalkyl, aryl, aralkyl, heteroaryl or sugar); cyano; mercapto; alkyl-thio-alkyl; thioalkoxy; thioalkyl; alkyl; cycloalkyl; aryl; alkenyl and alkynyl, which can be optionally substituted with e.g., an amino functionality.

A modification at the 2' position can be present in the arabinose configuration The term "arabinose configuration" refers to the placement of a substituent on the C2' of ribose in the same configuration as the 2'-OH is in the arabinose.

Modifications to the 2' position of ribose sugars can be found in Verma, S. el al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Oligonucleotides can also include an abasic sugar, which lack a nucleobase at C-1' or has other chemical groups in place of a nucleobase at C1'. See for example U.S. Pat. No. 5,998,203, contents of which are herein incorporated in their entirety. These abasic sugars can also be further containing modifications at one or more of the constituent sugar atoms. Oligonucleotides can also contain one or more sugars that are the L isomer, e.g. L-nucleosides. Modification to the sugar group can also include replacement of the 4'-0 with a sulfur, optionally substituted nitrogen or $CH_2$ group. In some embodiments, linkage between C1' and nucleobase is in the a configuration.

Modifications can also include acyclic nucleotides, wherein a C—C bonds between ribose carbons (e.g., C1'-C2', C2'-C3', C3'-C4', C4'-04', C1'-04') is absent and/or at least one of ribose carbons or oxygen (e.g., C1', C2', C3', C4' or 04') are independently or in combination absent from the nucleotide. Exemplary acyclic nucleotides are described, for example, in U.S. Pat. Nos. 5,225,550; 5,336,770; 5,576,427; 5,583,225; 5688,948; 5,792,868; 5,869,943; 6,017,923; 6,043,364; and 6,184,376, content of all of which is herein incorporated by reference.

Preferred sugar modifications are 2'-O-Me (2'-O-methyl), 2'-O-MOE (2'-O-methoxyethyl), 2'-F, 2'-0[2-(methylamino)-2-oxoethyl] (2'-O-NMA), 2'-S-methyl, 2'-O—$CH_2$-(4'-C) (LNA), 2'-O—$CH_2CH_2$-(4'-C) (ENA), 2'-O-aminopropyl (2'-O-AP), 2'-O-dimethylaminoethyl (2'-O-DMAOE), 2'-O-dimethylaminopropyl (2'-O-DMAP), and 2'-O-dimethylaminoethyloxyethyl (2'-O-DMAEOE).

It is to be understood that when a particular nucleotide is linked through its 2'-position to the next nucleotide, the sugar modifications described herein can be placed at the 3'-position of the sugar for that particular nucleotide, e.g., the nucleotide that is linked through its 2'-position can comprise a modification at the 3'-position. A modification at the 3' position can be present in the xylose configuration The term "xylose configuration" refers to the placement of a substituent on the C3' of ribose in the same configuration as the 3'-OH is in the xylose sugar.

The 3' and 5' ends of an oligonucleotide can be modified. Such modifications can be at the 3' end, 5' end or both ends of the molecule. For example, the 3' and/or 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' 0, N, S or C group of the sugar. Alternatively, the linker can connect to or replace the terminal atom of a nucleotide surrogate (e.g., PNAs).

Terminal modifications useful for modulating activity of siRNAs include modification of the 5' end with phosphate or phosphate analogs. For example, in some embodiments antisense strand of the siRNA is 5' phosphorylated or include a phosphoryl analog at the 5' terminus. 5'-phosphate modifications include those which are compatible with RISC mediated gene silencing. Modifications at the 5'-terminal end can also be useful in stimulating or inhibiting the immune system of a subject. Exemplary 5'-modifications include, but are not limited to, 5'-monophosphate (($HO)_2$(O)P—O-5'); 5'-diphosphate (($HO)_2$(O)P—O—P(HO)(O)—O-5'); 5'-triphosphate (($HO)_2$(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); 5'-alpha-thiotriphosphate; 5'-beta-thiotriphosphate; 5'-gamma-thiotriphosphate; 5'-phosphoramidates (($H^0)2(^0$)P$^-$NH$^{-5'}$, (110)(NH2)(O)P—O-5'); and 5'-alkylphosphonates (R(OH)(O)P—O-5', R=alkyl, e.g., methyl, ethyl, isopropyl, propyl, etc.). Other embodiments, include replacement of oxygen and/or sulfur with $BH_3$, $BH_3$ and/or Se.

Terminal modifications can also be useful for monitoring distribution, and in such cases the preferred groups to be added include fluorophores, e.g., fluorescein or an ALEXA FLUOR® dye, e.g., ALEXA FLUOR® 488. Terminal modifications can also be useful for enhancing uptake, useful modifications for this include targeting ligands. Terminal modifications can also be useful for cross-linking an oligonucleotide to another moiety; modifications useful for this include mitomycin C, psoralen, and derivatives thereof.

Terminal modifications are described in Manoharan, M. et al. *Antisense and Nucleic Acid Drug Development* 12, 103-128 (2002) and references therein, content of which is herein incorporated by reference in its entirety.

An oligonucleotide can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as inosine, xanthine, hypoxanthine, nubularine, isoguanisine, tubercidine, 5-methylcytosine (5-me-C); 5-hydroxymethyl cytosine; xanthine; hypoxanthine; 2-aminoadenine; 6-methyl and other 6-alkyl derivatives of adenine and guanine; 2-propyl and other 2-alkyl derivatives of adenine and guanine; 2-thiouracil; 2-thiothymine; 2-thiocytosine; 5-propynyl uracil; 5-propynyl cytosine; 6-azouracil; 6-azocytosine; 6-azothymine; 5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methyl and other 7-alkyl derivatives of adenine and guanine; 8-azaguanine; 8-azaadenine; 7-deazaguanine; 7-deazaadenine; 3-deazaguanine; and 3-deazaadenine.

Alternatively, or in addition, substituted or modified analogs of any of the above bases and "universal bases" can be employed. As used herein, a universal nucleobase is any modified or nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, inosine; 4-nitrobenzimidazole; 2,4-difluorotoluene; nitropyrrolyl, nitroindolyl (e.g. 5-nitroindole); 8-aza-7-deazaadenine; 4-fluoro-6-methylbenzimidazle; 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof. See for example, Loakes, 2001, *Nucleic Acids Research*, 29, 2437-2447, content of which is herein incorporated by reference in its entirety.

When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

Further nucleobases include those disclosed in U.S. Pat. No. 3,687,808; those disclosed in the Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; those disclosed in Modified Nucleosides in Biochemistry, Biotechnology and Medicine, Herdewijin, P. Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Content of all of the above is herein incorporated by reference in its entirety. Certain of these nucleobases are particularly useful for increasing the binding affinity of the oligonucleotides of the invention. These include 5-substituted pyrimidines, 6-azapyrimidines and N-2, N-6 and 0-6 substituted purines, including 2-aminopropyladenine, 5-propynyluracil and 5-propynylcytosine. 5-Methylcytosine substitutions have been shown to increase nucleic acid duplex stability by 0.6-1.2° C.

Representative IL S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference in its entirety.

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications can be incorporated in a single oligonucleotide or even at a single nucleoside within an oligonucleotide.

In some cases the modification will occur at all of the subject positions in the oligonucleotide but in many, and in fact in most cases it will not. By way of example, a modification can occur at a 3' or 5' terminal position, can occur in the internal region, can occur in 3', 5' or both terminal regions, e.g. at a position on a terminal nucleotide or in the last 2-10, or the last 2, 3, 4, 5, 6, 7, 8, 9, or 10 nucleotides of an oligonucleotide. In some embodiments, the 3' terminal nucleotide does not comprise a modification. In some embodiments, the 5' terminal nucleotide does not comprise a modification. In some embodiments neither 3' or 5' terminal nucleotides comprise a modification.

In some embodiments, the terminal nucleotide or the last 2-10 or the last 2, 3, 4, 5, 6, 7, 8, 9, or 10 nucleotides of at least one end of the oligonucleotide all comprise at least one modification. In some embodiments, the modification is same. In some embodiments, the terminal nucleotide or the last 2-10, or the last 2, 3, 4, 5, 6, 7, 8, 9, or 10 nucleotides at both ends of the oligonucleotide all comprise at least one modification. It is to be understood that type of modification and number of modified nucleotides on one end is independent of type of modification and number of modified nucleotides on the other end.

A modification can occur in a double strand region, a single strand region, or in both. A modification can occur in the double strand region of an oligonucleotide or can occur in a single strand region of an oligonucleotide. In some embodiments, a modification described herein does not occur in the region corresponding to the target cleavage site region. For example, a phosphorothioate modification at a non-bridging oxygen position can occur at one or both termini, can occur in a terminal regions, e.g., at a position on a terminal nucleotide or in the last 2-10, or the last 2, 3, 4, 5, 6, 7, 8, 9, or 10 nucleotides of a strand, or can occur in double-stranded and single-stranded regions, particularly at termini.

Some modifications can preferably be included on an oligonucleotide at a particular location, e.g., at an internal position of a strand, or on the 5' or 3' end of an oligonucleotide. A preferred location of a modification on an oligonucleotide, can confer preferred properties on the oligonucleotide. For example, preferred locations of particular modifications can confer optimum gene silencing properties, or increased resistance to endonuclease or exonuclease activity.

In vivo applications of oligonucleotides are limited due to presence of nucleases in the serum and/or blood. Thus in certain instances it is preferable to modify the 3', 5' or both ends of an oligonucleotide to make the oligonucleotide resistant against exonucleases. In some embodiments, the oligonucleotide comprises a cap structure at 3' (3'-cap), 5' (5'-cap) or both ends. In some embodiments, oligonucleotide comprises a 3'-cap. In another embodiment, oligonucleotide comprises a 5'-cap. In yet another embodiment, oligonucleotide comprises both a 3' cap and a 5' cap. It is to be understood that when an oligonucleotide comprises both a 3' cap and a 5' cap, such caps can be same or they can be different.

As used herein, "cap structure" refers to chemical modifications, which have been incorporated at either terminus of oligonucleotide. See for example U.S. Pat. No. 5,998,203 and Int. Pat. Pub. No. WO03/70918, content of both of which is herein incorporated by reference. Exemplary 5'-caps include, but are not limited to, ligands, 5'-5'-inverted nucleotide, 5'-5'-inverted abasic nucleotide residue, 2'-5' linkage, 5'-amino, 5-amino-alkyl phosphate, 5'-hexylphosphate, 5'-aminohexyl phosphate, bridging and/or non-bridging 5'-phosphoramidate, bridging and/or non-bridging 5'-phosphorothioate and/or 5'-phosphorodithioate, bridging or non bridging 5'-methylphosphonate, non-phosphodiester intersugar linkage between the end two nucleotides, 4',5'-methylene nucleotide, I-(beta-D-erythrofuranosyl) nucleotide, 4'-thio nucleotide, carbocyclic nucleotide, 1,5-anhydrohexitol nucleotide, L-nucleotides, alpha-nucleotides, modified nucleobase nucleotide, phosphorodithioate linkage, threo-pentofuranosyl nucleotide, acyclic nucleotide, acyclic 3,4-dihydroxybutyl nucleotide, acyclic 3,5-dihydroxypentyl nucleotide, 5'-mercapto nucleotide and 5'-1,4-butanediol phosphate. Exemplary 3'-caps include, but are not limited to, ligands, 3'-3'-inverted nucleotide, 3'-3'-inverted abasic nucleotide residue, 3'-2'-inverted nucleotide moiety, 3'-2'-inverted abasic moiety, 2'-5'-linkage, 3'-amino, 3'-amino-alkyl phosphate, 3'-hexylphosphate, 3'-aminohexyl phosphate, bridging and/or non-bridging 3'-phosphoramidate, bridging and/or non-bridging 3'-phosphorothioate and/or 3'-phosphorodithioate, bridging or non bridging 3'-methylphosphonate, non-phosphodiester intersugar linkage between the end two nucleotides, I-(beta-D-erythrofuranosyl) nucleotide, 4'-thio nucleotide, carbocyclic nucleotide, 1,5-anhydrohexitol nucleotide, L-nucleotides, alpha-nucleotides, modified nucleobase nucleotide, phosphorodithioate linkage, threo-pentofuranosyl nucleotide, acyclic nucleotide, acyclic 3,4-dihydroxybutyl nucleotide, acyclic 3,5-dihydroxypentyl nucleotide, and 3'-1,4-butanediol phosphate. For more details see Beaucage and Iyer, 1993, Tetrahedron 49, 1925, incorporated by reference herein.

The present invention also includes oligonucleotides which contain two or more chemically distinct regions, each made up of at least one monomer unit, i.e., a modified or unmodified nucleotide in the case of an oligonucleotide. Accordingly, in some embodiments, the oligonucleotide comprises two or more chemically distinct regions and has a structure as described in Int. Pat. App. Pub. No. WO2009/142822, and in U.S. Pat. App. Pub. Nos. 2005/0080246; 2007/0173475; 2007/0179107; 2007/0275921; and 2008/0146788, content of all of which is herein incorporated by reference in its entirety.

In some embodiments, the oligonucleotide comprises at least one (e.g., 1, 2, 3, 4, 5, 6, 7, 8, 9, or 10 or more), of 5'-5', 3'-3', 3'-2', 2'-5', 2'-3' or 2'-2' intersugar linkage. In some embodiments, the last nucleotide on the terminal end is linked via a 5'-5', 3'-3', 3'-2', 2'-5', 2'-3' or 2'-2' intersugar linkage to the rest of the oligonucleotide. In some embodiments, the last nucleotide on both the terminal ends is linked via a 5'-5', 3'-3', 3'-2', 2'-3' or 2'-2' intersugar linkage to the rest of the oligonucleotide. In some embodiments, at least one 5'-5', 3'-3', 3'-2', 2'-5', 2'-3' or 2'-2' intersugar linkage is a non-phosphodiester linkage.

An oligonucleotide can comprise at least one (e.g., 1, 2, 3, 4, 5, 6, 7, 8, 9, or 10 more), 5'-pyrimidine-purine-3' (5'-PyPu-3') and/or 5'-pyrimidine-pyrimidine-3' (5'-PyPy-3') dinucleotide sequence motif, wherein the 5'-most pyrimidine ribose sugar is modified at the 2'-position. Preferred 2'-modifications include, but are not limited to, 2'-H, 2'-O-Me (2'-O-methyl), 2'-O-MOE (2'-O-methoxyethyl), 2'-F, 2'-O-12-(methylamino)-2-oxoethyl] (2'-O-NMA), 2'-O—CH2CH2N(CH2CH2NMe2)2, 2'-S-methyl, 2'-O—$CH_2$-(4'-C) (LNA) and 2'-O—$CH_2CH_2$-(4'-C) (ENA). Without wishing to be bound by a theory, double-stranded oligonucleotides including these modifications are particularly stabilized against endonuclease activity.

Chemical ligation of oligonucleotides to cholesterol or polyethylene glycol can improve circulating half-life and/or uptake by CD4+ cells. See, for example, Dassie, et al., Nat. Biotechnol. 27: 839-849 and Soutscheck, et al., Nature 432: 173-178 (2004). Accordingly, a wide variety of entities, e.g., ligands, can be coupled to the aptamer-modualtor conjugates described herein. Ligands can include naturally occurring molecules, or recombinant or synthetic molecules. Exemplary ligands include, but arc not limited to, polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG$_2$, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, prolamine, cationic lipid, cationic porphyrin, quaternary salt of a polyamine, thyrotropin, melanotropin, lectin, glycoprotcin, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transfenin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g., steroids, bile acids, cholesterol, cholic acid, adamantane acetic acid, 1-pyrene butyric acid, dihydrotestosterone, 1,3-Bis-0(hexadecyl) glycerol, geranyloxyhexyl group, hexadecylglycerol, borneol, menthol, 1,3-propanediol, heptadecyl group, palmitic acid, myristic acid,03-(oleoyl)lithocholic acid, 03-(oleoyl) cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu$^{3+}$ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-KB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a-helical cell-permeation agent).

Peptide and peptidomimetic ligands include those having naturally occurring or modified peptides, e.g., D or L peptides; a, 13, or 7 peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 5-50 amino acids long, e.g., about 5, 10, 15, 20, 25, 30, 35, 40, 45, or 50 amino acids long.

Exemplary amphipathic peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H$_2$A peptides, Xenopus peptides, esculentinis-1, and caerins.

As used herein, the term "endosomolytic ligand" refers to molecules having endosomolytic properties. Endosomolytic ligands promote the lysis of and/or transport of the composition of the invention, or its components, from the cellular compartments such as the endosome, lysosome, endoplasmic reticulum (ER), golgi apparatus, microtubule, peroxisome, or other vesicular bodies within the cell, to the cytoplasm of the cell. Some exemplary endosomolytic ligands include, but are not limited to, imidazoles, poly or oligoimidazoles, linear or branched polyethyleneimines (PEIs), linear and brached polyamines, e.g. spermine, cationic linear and branched polyamines, pH-sensitive peptides, natural and synthetic fusogenic lipids, and natural and synthetic cationic lipids.

Without wishing to be bound by theory, fusogenic lipids fuse with and consequently destabilize a membrane. Fusogenic lipids usually have small head groups and unsaturated acyl chains. Exemplary fusogenic lipids include, but are not limited to, 1,2-dileoyl-sn-3-phosphoethanolamine (DOPE), phosphatidylethanolamine (POPE), and palmitoyloleoylphosphatidylcholine (POPC).

Ligands can be coupled to the oligonucleotides at various places, for example, 3'-end, 5'-end, and/or at an internal position. When two or more ligands are present, the ligand can be on opposite ends of an oligonucleotide. In preferred embodiments, the ligand is attached to the oligonucleotides via an intervening tether/linker. The ligand or tethered ligand can be present on a monomer when said monomer is incorporated into the growing strand. In some embodiments, the ligand can be incorporated via coupling to a "precursor" monomer after said "precursor" monomer has been incorporated into the growing strand. For example, a monomer having, e.g., an amino-terminated tether (i.e., having no associated ligand), e.g., monomer-linker-NH, can be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. When a ligand is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing oligonucleotides-ligand conjugates. Generally, an oligonucleotide is attached to a ligand moiety by contacting a reactive group (e.g., OH, SH, amine, carboxyl, aldehyde, and the like) on the oligonucleotide with a reactive group on the ligand moiety. In some embodiments, one reactive group is electrophilic and the other is nucleophilic. For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, content of which is herein incorporated by reference in its entirety.

In some embodiments, the ligands are linked to a monomer which is then incorporated into the growing oligonucleotide strand during chemical synthesis. Such monomers are also referred to as carrier monomers herein. Generally, such a monomer is a cyclic group (e.g. pyrrolidinyl, pyrazolinyl, pyrazolidinyl, imidazolinyl, imidazolidinyl, piperidinyl, piperazinyl,11,3i-dioxolane, oxazolidinyl, isoxazolidinyl, morpholinyl, thiazolidinyl, isothiazolidinyl, quinoxalinyl, pyridazinonyl, tetrahydrofuryl and decalin) or an acyclic group (e.g. a serinol backbone or a diethanolamine backbone).

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; contents which are herein incorporated in their entireties by reference.

It is to be understood, the aptamer, the gene modulator, and the nucleotidic linker each can comprise one or more nucleic acid modifications independently selected from the nucleic acid modifications described herein. For example, only the aptamer, only the gene modualtor, or only the nucleotidic linker can comprise a nucleic acid modification. In another example, any two of aptamer, gene modulator and nucleotidic linker (e.g., the aptamer and the gene modulator; the aptamer and the nucleotidic linker, or the gene modulator and the nucleotidic linker) can comprise a nucleic acid modification. In another example, all three of the aptamer, the gene moduatlor, and the nucleotidic linker comprise a nucleic acid modification.

Conjugate Synthesis

The conjugates of the invention can be prepared using solution-phase or solid-phase organic synthesis, or enzymatically by methods known in the art. Organic synthesis offers the advantage that the oligonucleotide strands comprising non-natural or modified nucleotides can be easily prepared. Any other means for such synthesis known in the art can additionally or alternatively be employed. It is also known to use similar techniques to prepare other oligonucleotides, such as the phosphorothioates, phosphorodithioates and alkylated derivatives. The double-stranded oligonucleotides can be prepared using a two-step procedure. First, the individual strands of the double-stranded molecule are prepared separately. Then, the component strands are annealed. Similarly, each component of the conjugate, e.g. aptamer, gene mosulator and nucleotidic linker, can be produced separately and then linked with the other components.

Regardless of the method of synthesis, the conjugate can be prepared in a solution (e.g., conjugate preparation can be precipitated and redissolved in pure double-distilled water, and lyophilized. The dried conjugate can then be resuspended in a solution appropriate for the intended formulation process.

Teachings regarding the synthesis of particular modified oligonucleotides can be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having beta-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

The conjugate components can be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotides: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta,* 1995, 78, 486-504; Beaucage, S. L. and Iyer, R. P., *Tetrahedron,* 1992, 48, 2223-2311 and Beaucage, S. L. and Iyer, R. P., *Tetrahedron,* 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Formulations

The conjugate comprising the aptamer and the siRNA can be suitably formulated for delivery to a cell. Many formulations for nucleic acid delivery are known and can be used. For example, the conjugate can be formulated in buffer solutions such as phosphate buffered saline solutions.

In another example, the aptamer-siRNA conjugate can be formulated in liposomes. As used herein, a liposome is a structure having lipid-containing membranes enclosing an aqueous interior. Liposomes can have one or more lipid membranes. In some embodiments, liposomes have an average diameter of less than about 100 nm. More preferred embodiments provide liposomes having an average diameter from about 30-70 nm and most preferably about 40-60 nm. Oligolamellar large vesicles and multilamellar vesicles have multiple, usually concentric, membrane layers and are typically larger than 100 nm. Liposomes with several nonconcentric membranes, i.e., several smaller vesicles contained within a larger vesicle, are termed multivesicular vesicles.

Liposomes can further comprise one or more additional lipids and/or other components such as sterols, e.g., cholesterol. Additional lipids can be included in the liposome compositions for a variety of purposes, such as to prevent lipid oxidation, to stabilize the bilayer, to reduce aggregation during formation or to attach ligands onto the liposome surface. Any of a number of additional lipids and/or other components can be present, including amphipathic, neutral, cationic, anionic lipids, and programmable fusion lipids. Such lipids and/or components can be used alone or in combination. One or more components of the liposome can comprise a ligand, e.g., a targeting ligand.

Liposome compositions can be prepared by a variety of methods that are known in the art. See e.g., U.S. Pat. Nos. 4,235,871; 4,737,323; 4,897,355 and 5,171,678; published International Applications WO 96/14057 and WO 96/37194; Felgner, P. L. et al., Proc. Nall. Acad. Sci., USA (1987) 8:7413-7417, Bangham, et al. *M. Mol. Biol.* (1965) 23:238, Olson, et al. *Biochim. Biophys. Acta* (1979) 557:9, Szoka, et al. *Proc. Natl. Acad. Sci.* (1978) 75: 4194, Mayhew, et al. *Biochim. Biophys. Acta* (1984) 775:169, Kim, et al. *Biochim. Biophys. Acta* (1983) 728:339, and Fukunaga, et al. *Endocrinol.* (1984) 115:757.

The conjugates of the invention can also be prepared and formulated as micelles. As used herein, "micelles" are a particular type of molecular assembly in which amphipathic molecules are arranged in a spherical structure such that all hydrophobic portions on the molecules are directed inward, leaving the hydrophilic portions in contact with the surrounding aqueous phase. The converse arrangement exists if the environment is hydrophobic.

In some embodiments, the formulations comprises micelles formed from a conjugate described and at least one amphiphilic carrier, in which the micelles have an average diameter of less than about 100 nm, preferably. More preferred embodiments provide micelles having an average diameter less than about 50 nm, and even more preferred embodiments provide micelles having an average diameter less than about 30 nm, or even less than about 20 nm.

Micelle formulations can be prepared by mixing an aqueous solution of the conjugate composition, an alkali metal C8 to C22 alkyl sulphate, and an amphiphilic carrier. The amphiphilic carrier can be added at the same time or after addition of the alkali metal alkyl sulphate. Micelles will form with substantially any kind of mixing of the ingredients but vigorous mixing in order to provide smaller size micelles.

The conjugates can also be prepared and formulated as emulsions. As used herein, "emulsion" is a heterogeneous system of one liquid dispersed in another in the form of droplets. Emulsions are often biphasic systems comprising two immiscible liquid phases intimately mixed and dispersed with each other. Either of the phases of the emulsion can be a semisolid or a solid, as is the case of emulsion-style ointment bases and creams. The conjugate can be present as a solution in either the aqueous phase, oily phase or itself as a separate phase.

In some embodiments, the compositions are formulated as microemulsions. As used herein, "microemulsion" refers to a system of water, oil and amphiphile which is a single optically isotropic and thermodynamically stable liquid solution. Microemulsions also include thermodynamically stable, isotropically clear dispersions of two inumiscible liquids that are stabilized by interfacial films of surface-active molecules.

The application of emulsion formulations via dermatological, oral and parenteral routes and methods for their manufacture have been reviewed in the literature, for example see Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., volume 1, p. 245; and Block, in Pharmaceutical Dosage Forms, Lieberman, Rieger and Banker (Eds.), 1988, Marcel Dekker, Inc., New York, N.Y., volume 1, p. 335, contents of which are herein incorporated by reference in their entirety.

Formulations of the conjugate with cationic lipids can be used to facilitate transfection of the conjugate into cells. For example, cationic lipids, such as lipofectin (U.S. Pat. No. 5,705,188, incorporated herein by reference), cationic glycerol derivatives, and polycationic molecules, such as polylysine (Int. App. Pub. No. WO 97/30731, incorporated herein by reference), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Exemplary formulations amenable to the present invention include those described, for example, in U.S. Pat. Nos. 4,897,355; 4,394,448; 4,235,871; 4,231,877; 4,224,179; 4,753,788; 4,673,567; 4,247,411; 4,814,270; 5,567,434; 5,552,157; 5,565,213; 5,738,868; 5,795,587; 5,922,859; and 6,077,663, and U.S. Pat. App. Pub. Nos. 2004/0203145 and 2005/0054598, content of all of which is herein incorporated by reference in its entirety. Behr (1994) Bioconjugate Chem.

5:382-389, and Lewis et al. (1996) PNAS 93:3176-3181), content of both of which is herein incorporated by reference, also describe formulations for oligonucleotides that are amenable to the invention.

Methods of the Invention

One aspect of the present invention relates to a method of modulating the expression of a target gene in a cell. The method comprising contacting a cell with an aptamer-gene modulator conjugate described herein. In some embodiments, the method further comprising the step of allowing the cell to internalize the conjugate. In some embodiments, the method further comprising the step of providing a conjugate described herein.

The method can be performed in a cell culture, e.g., in vitro or ex vivo, or in vivo, e.g., to treat a subject identified as being in need of treatment by a composition of the invention.

The term "contacting" or "contact" as used herein in connection with contacting a cell includes subjecting the cell to an appropriate culture media which comprises a conjugate described herein. Where the cell is in vivo, "contacting" or "contact" includes administering the conjugate in a pharmaceutical composition to a subject via an appropriate administration route such that the oligonucleotide contacts the cell in vivo.

For in vivo methods, a therapeutically effective amount of a compound described herein can be administered to a subject. Methods of administering compounds to a subject are known in the art and easily available to one of skill in the art.

In some embodiments, the cell is a mammalian cell. Without limitations, the mammalian cell can be a human cell or a non-human mammalian cell. For example, the cell can be a non-human primate cell. Furthermore, the cell can be infected with a pathogen, e.g. virus, bacteria, mycobacteria, fungi, unicellular organisms, including wild types and mutants thereof.

In some embodiments, the cell is a CD4+ cell. As used herein, a "CD4+ cell" is a cell having CD4 affixed to the surface of its cell membrane. In some embodiments, the CD4+ cell is a CD4+ HeLa cell. In some other embodiments, the CD4+ cell is a PM 1 cell. In still some other embodiments, the CD4+ cell is a primary human T lymphocyte. In yet some other embodiments, the CD4+ cell is a primary human macrophage. In yet still some other embodiments, the cell is a Dendritic cell. In some embodiments, the cell is cell that transgenically expresses CD4.

In some embodiments, the cell is present in a mammal. The mammal can be a human or a non-human primate. Non-human primates include, but are not limited to, chimpanzees, cynomologous monkeys, spider monkeys, and macaques, e.g., Rhesus.

The mammal can be a transgenic non-human mammal. Without wishing to be bound by a theory, transgenic non-human animals can be used as models for human disesases and disorders. In some embodiments, the mammal is a humanized knockdown mammal transplanted with human hematopoietic cell(s). By "transgenic mammal" is meant a non-human mammal having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. Accordingly, a transgene includes such heterologous nucleic acid, e.g., heterologous nucleic acid in the form of an expression construct (e.g., for the production of a "knock-in" transgenic animal) or a heterologous nucleic acid that upon insertion within or adjacent a target gene results in a decrease in target gene expression (e.g., for production of a "knock-out" transgenic animal).

In some embodiments, the cell is in humanized knock-down mouse that has been transplanted with human hematopoietic cell(s).

In some embodiments, the cell is in a subject, which subject has a HIV infection.

In some embodiments, the cell is in a subject, which subject is need of treatment for HIV infection.

Without wishing to be bound by a theory, modulating the expression of gene in a CD4+ cell can be used to modulate the phenotypes of CD4+ cells (e.g., Th1, Th2, Th17, T-reg, etc.). Accordingly, in one aspect, the invention provide a method of modulating the phenotype of a CD4+ cell, the method comprising the method comprising contacting the cell with a conjugate comprising an aptamer and a gene modulator. The term "cell phenotype" includes any detectable aspect of a cell, such as the visual appearance or molecular function of the cell. Exemplary phenotypes of CD4 cells include, but are not limited to Th1, Th2, Th17, and T-reg. As used herein, the phrase "modulate the phenotype" refer to any measurable or observable change in any measurable or observable characteristic of a cell. As such, a phenotypic modulation can be any measurable change, for example, in the morphology of a cell, in the expression of one more proteins by a cell, in the functional characteristics of a cell (e.g., contractility, migratory behavior, secretion of a particular factor), and/or in the growth factor requirements of the cell. Without wishing to be bound by a theory, modulating the phenotype of a CD4+ cell can lead to treatment and/or reduction of aberrant immune reactions such as autoimmune responses.

In another aspect, the invention provides a method of a method of treating and/or preventing a cancer in a subject in need thereof, the method comprising administering to the subject a conjugate, typically at therapeutically effective amount, wherein the conjugate comprises an aptamer and a gene modulator, wherein the aptamer is a CD4+ aptamer, and the gene modulator inhibits the expression of an onco-gene.

The term "cancer" refers to a neoplasm or tumor resulting from abnormal uncontrolled growth of cells. As used herein, the term "cancer" includes any neoplasm, such as a carcinoma (derived from epithelial cells) or sarcoma (derived from connective tissue cells) or a cancer of the blood, such as leukemia. Examples of cancer include, but are not limited to, leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia Vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Gushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fingating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

HIV Prevention or Treatment

Another aspect of the present invention relates to a method of treating or preventing a HIV infection in a subject in need thereof, the method comprising administering to the subject a therapeutically effective amount of a conjugate comprising an aptamer and a siRNA, wherein the aptamer is a CD4+ aptamer and the siRNA inhibits the expression of a HIV gene and/or a endogenous cell gene required for or involved in HIV infection, replication and/or function.

As used herein, the term "HIV infection" generally encompasses infection of a host, particularly a human host, by the human immunodeficiency virus (HIV) family of retroviruses including, but not limited to, HIV I, HIV II, HIV III (also known as HTLV-II, LAV-1, LAV-2), and the like. Non-human hosts can include a host infected with simian immunodeficiency virus (SW), simian/human immunodeficiency virus (SHIV), feline immunodeficiency virus (FIV), and bovine immunodeficiency virus (BIV). "HIV" can be used herein to refer to any strains, forms, subtypes, clades and variations in the HIV family, e.g., clades A, B, C, D, and G, R5 and R5X4 viruses, etc. Thus, treating HIV infection will encompass the treatment of a subject who is a carrier of any of the HIV family of retroviruses or a person who is diagnosed of active AIDS, as well as the treatment or prophylaxis of the AIDS-related conditions in such persons. A carrier of HIV may be identified by any methods known in the art. For example, a person can be identified as an HIV carrier on the basis that the person is anti-HIV antibody positive, or is HIV-positive, or has symptoms of AIDS.

The term "treating" is used conventionally, e.g., the management or care of a subject for the purpose of combating, alleviating, reducing, relieving, improving, or elimination, one or more signs or symptoms associated with HIV infection. Treatment includes delaying the progression of I IV and its associated symptoms, thereby extending the life expectancy of an infected subject, and/or delaying or reducing the onset of symptoms associated with HIV infection. Treating can involve inhibiting, reducing, diminishing, etc., the replication and other events in the life cycle of the HIV virus. That is, "treating HIV infection" should be understood as treating a patient who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating CD4+T cells), and AIDS (which is defined by more serious AIDS-defining illnesses and/or a decline in the circulating CD4 cell count to below a level that is compatible with effective immune function). In addition, "treating or preventing HIV infection" will also encompass treating suspected infection by HIV after suspected past exposure to HIV by e.g., contact with HIV contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "treating HIV infection" also encompasses treating a person who has not been diagnosed as having HIV infection but is believed to be at risk of infection by HIV. The term "treating HIV" also means treating a patient who exhibits more serious AIDS-defining illnesses and/or a decline in the circulating CD4 cell count to below a level that is compatible with effective immune function. The term "treating HIV" also encompasses treating AIDS-related conditions, which means disorders and diseases incidental to or associated with AIDS or HIV infection such as AIDS related complex (ARC), progressive generalized lymphadenopathy (PGI), anti-HIV antibody positive conditions, and HIV-positive conditions, AIDS-related neurological conditions (such as dementia or tropical paraparesis), Kaposi's sarcoma, thrombocytopenia *purpurea* and associated opportunistic infections such as *Pneumocystis carinii* pneumonia, Mycobacterial tuberculosis, esophageal candidiasis, toxoplasmosis of the brain, CMV retinitis, HIV-related encephalopathy, HIV-related wasting syndrome, etc.

The term "preventing" HIV infection indicates that a subject's susceptibility to HIV infection upon exposure to the virus is reduced or diminished as a result of the administration of the poxvirus. The subject's resistance to HIV infection is increased or improved by the conjugate treatment since s/he is less likely to become infected by the virus. Any amount of improved resistance is useful, e.g., greater than 1.5-fold, greater than 2-fold, greater than 3-fold, greater than 4-fold, 5-fold, greater than 7-fold, greater than ten-fold, etc., and any such improvement can be regarded as prevention. Inhibition of HIV infection is considered a preventive measure even if it does not confer a complete immunity to HIV or AIDS.

Standard methods for measuring in vivo HIV infection can be used to determine whether a subject is positively responding to treatment with the HIV-specific gene modulator conjugate. For example, after treatment with an aptamer-gene modulator conjugate described herein, a subject's T cell count can be monitored. A rise in T cells indicates that the subject is benefiting from administration of conjugates. This, as well as other methods known to the art, may be used to determine the extent to which the methods of the present invention are effective at treating and/or preventing a HIV infection in a subject. Virus load can also be monitored using, e.g., quantitative RNA analysis using techniques, such as quantitative PCR, and the like.

As used herein, a "subject" means a human or animal, which can be infected by the human immunodeficiency virus (HIV) family of retroviruses including HIV 1, HIV 11, HIV III (also known as HTLV-II, LAV-1, LAV-2), simian immunodeficiency virus (SIV), simian/human immunodeficiency virus (SHIV), feline immunodeficiency virus (FIV), and bovine immunodeficiency virus (BIV). Examples of subjects include primates (e.g., humans, and monkeys). Non-human primates include chimpanzees, cynomologous monkeys, spider monkeys, and macaques, e.g., Rhesus. Patient or subject includes any subset of the foregoing, e.g., all of the above, but excluding one or more groups or species such as humans, primates or rodents. In certain embodiments the aspects described herein, the subject is a mammal, e.g., a primate, e.g., a human. The terms, "patient" and "subject" are used interchangeably herein. The terms, "patient" and "subject" are used interchangeably herein. A subject can be male or female. The subject can be of any agen, such as an adult, a child or a fetus.

Without limitations, the subject can be a non-human primate, which non-human-primate has been transplanted with human hematopoietic cells. In one embodiment, subject is a mouse transplanted with human hematopoietic cell(s), i.e., a humanized knockdown mouse.

Subjects, who have been exposed to HIV virus, or who are at risk for developing the disease, are particular candidates for methods of the invention. For instance, a subject who has not yet tested positive, but has been exposed to HIV, can be administered the conjugate as a prophylactic/therapeutic approach. Individuals at high-risk for the disease, such as sexually-active individuals particularly in risk populations, such as prostitutes, sexually active individuals in parts of the world where HIV infection is high, subjects receiving blood and/or other invasive medical procedures, can also receive the conjugates to increase their resistance to HIV infection.

A subject can be one who has been previously diagnosed with or identified as suffering from or having a HIV infection or a disease or disorder a disease or disorder caused by a HIV infection.

A subject can be one who is currently being treated for a HIV infection or a disease or disorder a disease or disorder caused by a HIV infection.

In some embodiments of the aspects described herein, the method further comprising diagnosing a subject for a HIV infection or a disease or disorder caused by a HIV infection before onset of treatment with a method described herein. Methods of diagnosing HIV infections are well known in the art. For example, a subject can be diagnosed with a HIV infection based on the presence of anti-virus antibodies, viral RNA, viral-DNA, viral proteins, or viral particles in a subject's serum or blood. Methods for detecting anti-virus antibodies, viral RNA, viral-DNA, viral proteins, or viral particles are well known to the skilled artisan. In many cases kits for diagnosing viral infections are commercially available.

In some embodiments, the method further comprising selecting a subject diagnosed with a HIV infection or a disease or disorder caused by a HIV infection before onset of administration of the conjugate.

Pharmaceutical Compositions

For administration to a subject, the conjugates of the invention can be provided in pharmaceutically acceptable compositions. Accordingly, in one aspect, the invention provides a pharmaceutical composition comprising a therapeutically-effective amount of one or more of the conjugates described herein, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8)

transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other nontoxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a conjugate which is effective for producing some desired therapeutic effect in at least a sub-population of cells in an animal at a reasonable benefit/risk ratio applicable to any medical treatment. For example, an amount of a conjugate described herein administered to a subject that is sufficient to produce a statistically significant, measurable inhibition of expression of a HIV gene, a cellular gene required for HIV infection and/or replication, and/or a cellular gene required for HIV function.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject.

A conjugate described herein can be administered by any appropriate route known in the art including, but not limited to, oral or parenteral routes, including intravenous, intramuscular, subcutaneous, transdermal, airway (aerosol), pulmonary, nasal, rectal, vaginal, and topical (including on the skin, and body cavities, such as buccal, vaginal, rectal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments of the aspects described herein, the compositions are administered by intravenous infusion or injection. In some embodiments, administration is by injection, infusion, instillation, inhalation, ingestion, and/or by topical application.

In some embodiments, the aptamer—modulator conjugate described herein can be used as the active ingredient of a microbicide. A microbicide can be used to prevent transmission of sexually transmitted diseases and viruses such as HIV.

Because the threat of spreading HIV is greatest via oral, vaginal, or rectal routes, in some embodiments it is preferable that the administration of the aptamer—modulator conjugates is intraorally, intravaginally, or intrarectally. Without wishing to be bound by a theory, intravaginal and/or intrarectal adminsteration can inhibit the transmission of sexually transmitted diseases and viruses such as HIV. Accordingly, the conjugate can be administered to a subject before sexual intercourse. Such administering can be at a sufficient time before sexual intercourse to allow the conjugate to be taken up by the cell(s).

The amount of a conjugate described herein that can be combined with a carrier material to produce a single dosage form will generally be that amount of the compound that produces a therapeutic effect. Generally out of one hundred percent, this amount will range from about 0.001% to 99% of the compound, preferably from about 0.01% to about 70%, most preferably from 5% to about 30%.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that a conjugate described herein is given at a dose from 1 pg/kg to 150 mg/kg, 1 pg/kg to 100 mg/kg, 1 pg/kg to 50 mg/kg, 1 Ng/kg to 20 mg/kg, 1 Ng/kg to 10 mg/kg, 1 pg/kg to 1 mg/kg, 100 p g/kg to 100 mg/kg, 100 p g/kg to 50 mg/kg, 100 pg/kg to 20 mg/kg, 100 pg/kg to 10 mg/kg, 100 pg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the conjugates are administered at a dosage so that the gene modulator has an in vivo, e.g., serum or blood, concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the conjugates described herein. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The conjugates described herein can be administered to a subject in combination with one or more pharmaceutically active agents. Exemplary pharmaceutically active compound include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of The Merck Index, the complete content of all of which are herein incorporated in its entirety.

In some embodiments, pharmaceutically active agent is an antiviral agent. As used herein, the term "antiviral agent" means an agent that is effective to inhibit the formation and/or replication of a virus in a mammal. This includes agents that interfere with either host or viral mechanisms necessary for the formation and/or replication of a virus in a mammal. Such agents can be selected from immunomodulatory agents, inhibitors of a virus polymerase or inhibitors of another target in the virus life cycle. Examples of antiviral agents include a-methyl-1-adamantanemethylamine, hydroxy-ethoxymethylguanine, adamantanamine, 5-iodo-2'-deoxyuridine, trifluorothymidine, AZT, adenine arabinoside, Abacavir, Aciclovir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Entry, inhibitors, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir, (Tamiflu), Peginterferon alfa-2a, Penciclovir, Peramivir, Pleconaril, Podophyllotoxin, Raltegravir, Ribavirin, Rimantadine, Ritonavir, Pyramidine, Saquinavir, Stavudine, Tenofovir, Tenofovir, disoproxil, lipranavir, Trifluridine, Trizivir, Tromantadine, Truvada, Valaciclovir, (Valtrex), Valganciclovir, Vicriviroc, Vidarabine, Viramidine, Zalcitabine, Zanamivir, (Relenza), and Zidovudine.

The conjugate and the pharmaceutically active agent can be administered to the subject in the same pharmaceutical composition or in different pharmaceutical compositions (at the same time or at different times). When administered at different times, the conjugate and the pharmaceutically active agent can be administered within 5 minutes, 10 minutes, 20 minutes, 60 minutes, 2 hours, 3 hours, 4, hours, 8 hours, 12 hours, 24 hours of administration of the other When the conjugate and the pharmaceutically active agent are administered in different pharmaceutical compositions, routes of administration can be different.

In some embodiment, a conjugate described herein is administered to a subject without administration of an additional pharmaceutically active agent.

Kits

In some aspects, the invention provides kits that include a suitable container containing an aptamer—modulator conjugate. In some embodiments, the aptamer—modulator conjugate is in a formulation, e.g., pharmaceutical composition. In addition to the conjugate or the formualtion, the kit can include informational material. The informational material can be descriptive, instructional, marketing or other material that relates to the methods described herein and/or the use of the compound for the methods described herein. For example, the informational material describes methods for administering the formulation to a subject or methods for inhibiting the expression of a gene in a cell. The kit can also include a delivery device.

In one embodiment, the informational material can include instructions to administer the formulation in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In some embodiments the individual components of the formulation can be provided in one container. Alternatively, it can be desirable to provide the components of the formulation separately in two or more containers, e.g., one container for conjugate preparation, and at least another for a carrier compound. The different components can be combined, e.g., according to instructions provided with the kit. The components can be combined according to a method described herein, e.g., to prepare and administer a pharmaceutical composition.

In addition to the conjugate and/or the formulation, the composition of the kit can include other ingredients, such as a solvent or buffer, a stabilizer or a preservative, and/or a second agent for treating a condition or disorder described herein. Alternatively, the other ingredients can be included in the kit, but in different compositions or containers than the conjugate and/or the formulation. In such embodiments, the kit can include instructions for admixing the conjugate and/or the formulation and the other ingredients, or for using the conjugate and/or the formulation together with the other ingredients.

The conjugate can be provided in any form, e.g., liquid, dried or lyophilized form. It is preferred that the conjugate be substantially pure and/or sterile. When the conjugate is provided in a liquid solution, the liquid solution preferably is an aqueous solution, with a sterile aqueous solution being preferred. When the conjugate is provided as a dried form, reconstitution generally is by the addition of a suitable solvent. The solvent, e.g., sterile water or buffer, can optionally be provided in the kit.

Similarly, when the conjugate is provided as a formulation, the formulation can be provided in any form, e.g., liquid, dried or lyophilized form. Preferably, the formulation is substantially pure and/or sterile. When the formualtion is provided as a dried form, reconstitution generally is by the addition of a suitable solvent, e.g., sterile water or buffer, which can optionally be provided in the kit.

In some embodiments, the kit contains separate containers, dividers or compartments for the conjugate and informational material. For example, the conjugate can be contained in a bottle, vial, or syringe, and the informational material can be contained in a plastic sleeve or packet. In other embodiments, the separate elements of the kit are contained within a single, undivided container. For example, the conjugate is contained in a bottle, vial or syringe that has attached thereto the informational material in the form of a label.

In some embodiments, the kit includes a plurality, e.g., a pack, of individual containers, each containing one or more unit dosage forms of the conjugate, e.g. conjugate formulation. For example, the kit includes a plurality of syringes, ampules, foil packets, or blister packs, each containing a single unit dose of the conjugate. The containers of the kits can be air tight and/or waterproof.

Definitions

Unless slated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Thus for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein, the term "transgene" refers to a nucleic acid which codes for a specific protein or RNA product and which is capable of becoming integrated into at least one chromosome of an organism. The transgene nucleic acids include the promoter region from the same gene or another gene. The transgene nucleic acid can be obtained from another species or the same species as the host organism.

As used herein, the term "exogenous gene" refers to to a gene foreign to the cell, e.g. a gene of a pathogen, which is present in the cell after infection thereof.

The term "alkyl" refers to saturated or unsaturated nonaromatic hydrocarbon chains that may be a straight chain or branched chain, containing 1 to 24 carbon atoms, which may be optionally inserted with N, O, or S. For example, $C_1$-$C_6$ indicates that the group may have from 1 to 6 (inclusive) carbon atoms in it. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like.

The term "alkenyl" refers to an alkyl that comprises at least one double bond. Exemplary alkenyl groups include, but are not limited to, for example, ethylenyl, propylenyl, 1-butenyl, 2-butenyl, isobutylenyl, 1-pentenyl, 2-pentenyl, 3-methyl-1-butenyl, 1-methyl-2-buten-1-yl, 2-methyl-2-butenyl, 2,3-dimethyl-2-butenyl, and the like The term "alkynyl" refers to an alkyl that comprises at least one triple bond. Exemplary alkynyl groups include, acetylenyl, propynyl, 1-butynyl, 2-butynyl, 1-pentynyl, 2-pentynyl, 3-methyl-1-butynyl, and the like.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 4-nitrophenyl, and the like.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "haloalkyl" refers to an alkyl group having one, two, three or more halogen atoms attached thereto. Exemplary haloalkyl groups include, but are not limited to chloromethyl, bromoethyl, trifluoromethyl, and the like.

The term "optionally substituted" means that the specified group or moiety, such as an alkyl group, alkenyl group, and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, or heteroaryl group at any atom of that group. Suitable substituents include, without limitation, halogen, hydroxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

As used herein, the term "small molecule" can refer to compounds that are "natural product-like," however, the term "small molecule" is not limited to "natural product-like" compounds. Rather, a small molecule is typically characterized in that it contains several carbon—carbon bonds, and has a molecular weight of less than 5000 Daltons (51(D), preferably less than 3 kD, still more preferably less than 21(D, and most preferably less than 1 kD. In some cases it is preferred that a small molecule have a molecular mass equal to or less than 700 Daltons.

As used herein, the term "biological activity" or "bioactivity" refers to the ability of a compound to affect a biological sample. Biological activity can include, without limitation, elicitation of a stimulatory, inhibitory, regulatory, toxic or lethal response in a biological assay. For example, a biological activity can refer to the ability of a compound to modulate the effect/activity of an enzyme, block a receptor, stimulate a receptor, modulate the expression level of one or more genes, modulate cell proliferation, modulate cell division, modulate cell morphology, or any combination thereof. In some instances, a biological activity can refer to the ability of a compound to produce a toxic effect in a biological sample.

The biological activity can be determined by assaying a cellular response. Exemplary cellular responses include, but are not limited to, lysis, apoptosis, growth inhibition, and growth promotion; production, secretion, and surface exposure of a protein or other molecule of interest by the cell; membrane surface molecule activation including receptor activation; transmembrane ion transports; transcriptional regulations; changes in viability of the cell; changes in cell morphology; changes in presence or expression of an internal component of the cell; changes in presence or expression of a nucleic acid produced within the cell; changes in the activity of an enzyme produced within the cell; and changes in the presence or expression of a receptor.

Assaying of cellular responses can be done in a number of ways. Detection can be by just visual inspection; e.g. cell growth or not, cell morphology, etc. or can be by the use of detector molecules. Detector molecules can be already present in the microwells; e.g. when looking at expression of a gene with a GFP reporter or present in the culture media in the microwell. Alternatively, the detector molecule can be added after the test compound has been allowed to transfer to the cell culture media in the microwell for a sufficient time. Also, the detector molecules can be deposited with the test compound so that the detector molecules are transferred to the cell culture media at the same time as the test compound. The assaying can optionally include a step of washing off excess detector molecule.

Detector molecules can be selected from the group consisting of nucleic acids including modified analogues thereof, peptides, proteins, and antibodies including antibody fragments, enzyme substrates and specific dyes. Non-limiting suitable examples of specific dyes are well known in the art and include Fluo-3, Fluo-4, calecin A M, ethedium bromide, TO-PRO-3, Alexa Fluor 488 conjugated Annexin V, and Ca-dyes such as e.g. Calcium Green-1. Other dyes amenable to the present invention include those described available from Molecular Probes (Eugene, Oreg., USA). Dyes such as DAPI and Hoechst can be used for staining cell nuclei to analyze total cell counts.

Some embodiments of the invention can be described by the following numbered paragraphs:
1. A conjugate comprising an aptamer and a gene modulator linked to each other by a linker, wherein the linker is a double-stranded oligonucleotide comprising a first oligonucleotide strand and a second oligonucleotide strand, wherein the first oligonucleotide strand is linked to the aptamer and the second oligonucleotide strand is linked to the gene modulator and the gene modulator and the second oligonucleotide strand are linked by a non-nucleotidic linker.
2. The conjugate of paragraph 1, wherein nucleotide sequence of the first oligonucleotide is part of the nucleotide sequence of the aptamer.
3. The conjugate of any of paragraphs 1-2, wherein the gene modulator is a siRNA, microRNA, a pre-microRNA, an antisense RNA or a mRNA.
4. The conjugate of any of paragraphs 1-3, wherein the linker double-stranded oligonucleotide comprises 5 to 15 nucleotide base pairs.
5. The conjugate of any of paragraphs 1-4, wherein the non-nucleotidic linker is an optionally substituted C3-C10 alkyl.
6. The conjugate of any of paragraphs 1-5, wherein the non-nucleotidic linker is —OCH2CH2CH2O— (C3 linker).
7. The conjugate of any of paragraphs 1-6, wherein the first strand is linked to 3'-end of the aptamer.
8. The conjugate of any of paragraphs 1-7, wherein the gene modulator is a double-stranded oligonucleotide comprising a sense strand and an antisense strand.
9. The conjugate of paragraph 8, wherein the second strand is linked to 3'-end of the sense strand.
10. The conjugate of any of paragraphs 1-9, wherein the conjugate comprises a nucleic acid modification selected from the group consisting of internucleotide linkage modification (intersugar linkage modification), sugar modification, nucleobase modification, and any combinations thereof.
11. The conjugate of paragraph 10, wherein the internucleotide linkage modification is selected from the group consisting of phosphorothioate, phosphorodithioate, phosphotriester (e.g. alkyl phosphotriester), aminoalkylphosphotriester, alkyl-phosphonate (e.g., methyl-phosphonate), selenophosphate, phosphoramidate (e.g., N-alkylphosphoramidate), boranophosphonate, and any combinations thereof.
12. The conjugate of any of paragraphs 10-11, wherein the sugar modification is selected from the group consisting of 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), arabinose sugar, and any combinations thereof.
13. The conjugate of any of paragraphs 10-12, wherein the nucleobase modification is selected from the group consisting of inosine, xanthine, hypoxanthine, nubularine, isoguanisine, tubercidine, 5-methylcytosine (5-me-C); 5-hydroxymethyl cytosine; xanthine; hypoxanthine; 2-aminoadenine; 6-methyl and other 6-alkyl derivatives of adenine and guanine; 2-propyl and other 2-alkyl derivatives of adenine and guanine; 2-thiouracil; 2-thiothymine; 2-thiocytosine; 5-propynyl uracil; 5-propynyl cytosine; 6-azouracil; 6-azocytosine; 6-azothymine; 5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methyl and other 7-alkyl derivatives of adenine and guanine; 8-azaguanine; 8-azaadenine; 7-deazaguanine; 7-deazaadenine; 3-deazaguanine; 3-deazaadenin; universal base; and any combinations thereof.

14. The conjugate of any of paragraphs 10-13, wherein the backbone modification is selected from the group consisting of morpholino, cyclobutyl, pyrrolidine, peptide nucleic acid (PNA), aminoethylglycyl PNA (aegPNA), backnone-extended pyrrolidine PNA (bepPNA), and any combinations thereof.

15. The conjugate of any of paragraphs 1-14, wherein the gene modulator is 15-30 nucleotides in length.

16. The conjugate of any of paragraphs 1-15, wherein the gene modulator inhibits the expression of an endogenous gene, a transgene, or an exogenous gene (e.g. a gene of a pathogen, which is present in the cell after infection thereof).

17. The conjugate of any of paragraphs 1-16, wherein the gene modulator inhibits the expression of a gene selected from the group consisting of genes promoting unwanted cell proliferation, growth factor gene, growth factor receptor gene, genes expressing kinases, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, and a gene which mediates a neurological disease 18. The conjugate of any of paragraphs 1-17, wherein the gene modulator inhibits the expression of a gene selected from the group consisting of CCR-5 gene, CD45 gene, TREX1 gene, lamin A gene, EG5 gene, FoxP3 gene, a HIV gene, a gene required for HIV replication, a gene required for HIV infection, and any combinations thereof.

19. The conjugate of any of paragraphs 1-18, wherein the gene modulator comprises any one or more of the nucleotide sequences selected from the group consisting of SEQ ID NOs: 43-61 and any combinations thereof.

20. The conjugate of any of paragraphs 1-19, wherein the aptamer directs cell-specific delivery of the conjugate when contacted with a cell.

21. The conjugate of paragraph 20, wherein the cell is a CD4+ cell, a macrophage, or a dendritic cell.

22. The conjugate of any of paragraphs 1-21, wherein the aptamer is a CD4 aptamer.

23. The conjugate of any of paragraphs 1-22, wherein the aptamer comprise a nucleotide sequence selected from the group consisting of SEQ ID NOs: 62-66 and any combinations thereof.

24. The conjugate of any of paragraphs 1-23, wherein the conjugates comprises nucleotide sequences selected from: (i) SEQ ID NOs: 58 and 68; (ii) SEQ ID NOs: 58 and 70; (iii) SEQ ID NOs: 59 and 75, 62, and 71; and (iv) SEQ ID NOs: 61 and 67.

25. A pharmaceutical composition comprising a conjugate of any of paragraphs 1-24 and a pharmaceutically acceptable carrier.

26. A method of inhibiting HIV infection in a cell, the method comprising contacting the cell with a conjugate comprising an aptamer and gene modulator, wherein the aptamer is a CD4 aptamer and the gene modulator inhibits the expression of a HIV gene, a cell gene required for HIV infection, or any combinations thereof.

27. The method of paragraph 26, wherein the gene modulator is a siRNA, microRNA, a pre-microRNA, or an antisense.

28. The method of any of paragraphs 26-27, wherein the aptamer and the gene modulator are linked by a phosphodiester, a modified intersugar linkage, a nucleotidic or a non-nucleotidic linker.

29. The conjugate of any of paragraphs 26-28, wherein the gene modulator is linked to 3'-end of the aptamer.

30. The method of any of paragraphs 26-29, wherein the gene modulator is a double-stranded oligonucleotide comprising a sense strand and an antisense strand.

31. The method of paragraph 30, wherein the aptamer is linked to 5'-end of the sense strand.

32. The method of any of paragraphs 26-31, wherein the conjugate comprises a nucleic acid modification selected from the group consisting of internucleotide linkage modification (intersugar linkage modification), sugar modification, nucleobase modification, and any combinations thereof.

33. The method of paragraph 32, wherein the internucleotide linkage modification is selected from the group consisting of phosphorothioate, phosphorodithioate, phosphotriester (e.g. alkyl phosphotriester), aminoalkylphosphotriester, alkyl-phosphonate (e.g., methyl-phosphonate), selenophosphate, phosphoramidate (e.g., N-alkylphosphoramidate), boranophosphonate, and any combinations thereof.

34. The method of any of paragraphs 32-33, wherein the sugar modification is selected from the group consisting of 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH2-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), arabinose sugar, and any combinations thereof.

35. The method of any of paragraphs 32-34, wherein the nucleobase modification is selected from the group consisting of inosine, xanthine, hypoxanthine, nubularine, isoguanisine, tubercidine, 5-methylcytosine (5-me-C); 5-hydroxymethyl cytosine; xanthine; hypoxanthine; 2-aminoadenine; 6-methyl and other 6-alkyl derivatives of adenine and guanine; 2-propyl and other 2-alkyl derivatives of adenine and guanine; 2-thiouracil; 2-thiothymine; 2-thiocytosine; 5-propynyl uracil; 5-propynyl cytosine; 6-azouracil; 6-azocytosine; 6-azothymine; 5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methyl and other 7-alkyl derivatives of adenine and guanine; 8-azaguanine; 8-azaadenine; 7-deazaguanine; 7-deazaadenine; 3-deazaguanine; 3-deazaadenin; universal base; and any combinations thereof.

36. The method of any of paragraphs 32-35, wherein the backbone modification is selected from the group consisting of morpholino, cyclobutyl, pyrrolidine, peptide nucleic acid (PNA), aminoethylglycyl PNA (aegPNA), backnone-extended pyrrolidine PNA (bepPNA), and any combinations thereof.

37. The method of any of paragraphs 26-36, wherein the gene modulator is 15-30 nucleotides in length.

38. The method of any of paragraphs 26-37, wherein the gene modulator inhibits the expression of a gene selected from the group consisting of CCR-5 gene, CD45 gene, TREX1 gene, lamin A gene, EG5 gene, FoxP3 gene, and any combinations thereof.

39. The method of any of paragraphs 26-38, wherein the gene modulator comprises any one or more of the nucleotide sequences selected from the group consisting of SEQ ID NOs: 43-61 and any combinations thereof.

40. The method of any of paragraphs 26-39, wherein the aptamer directs cell-specific delivery of the conjugate when contacted with the cell.

41. The method of any of paragraphs 26-40, wherein the cell is a CD4+ cell, a macrophage, or a dendritic cell.

42. The method of any of paragraphs 26-41, wherein the aptamer comprise a nucleotide sequence selected from the group consisting of SEQ ID NOs: 62-66 and any combinations thereof.

43. The method of any of paragraphs 26-42, wherein the conjugates comprises nucleotide sequences selected from: (i) SEQ ID NOs: 58 and 68; (ii) SEQ ID NOs: 58 and 70; (iii) SEQ ID NOs: 59 and 75, 62, and 71; and (iv) SEQ ID NOs: 61 and 67.

44. The method of any of paragraphs 26-43, wherein the conjugate is a conjugate of any of paragraphs 1-24.

45. A method of treating or inhibiting HIV infection in a subject in need thereof, the method comprising administering to the subject a therapeutically effective amount of a conjugate or a pharmaceutical composition comprising the conjugate and a pharmaceutically acceptable carrier, wherein the conjugates comprises an aptamer and a gene modulator; the aptamer is a CD4 aptamer; and the gene modulator inhibits the expression of HIV gene, a cell gene required for HIV infection, or any combinations thereof.

46. The method of paragraph 45, wherein the gene modulator is a siRNA, microRNA, a pre-microRNA, or an antisense.

47. The method of any of paragraphs 45-46, wherein the aptamer and the gene modulator are linked by a phosphodiester, a modified intersugar linkage, a nucleotidic or a non-nucleotidic linker.

48. The conjugate of any of paragraphs 45-47, wherein the gene modulator is linked to 3'-end of the aptamer.

49. The method of any of paragraphs 45-48, wherein the gene modulator is a double-stranded oligonucleotide comprising a sense strand and an antisense strand.

50. The method of paragraph 48, wherein the aptamer is linked to 5'-end of the sense strand.

51. The method of any of paragraphs 45-50, wherein the conjugate comprises a nucleic acid modification selected from the group consisting of internucleotide linkage modification (intersugar linkage modification), sugar modification, nucleobase modification, and any combinations thereof.

52. The method of paragraph 51, wherein the internucleotide linkage modification is selected from the group consisting of phosphorothioate, phosphorodithioate, phosphotriester (e.g. alkyl phosphotriester), aminoalkylphosphotriester, alkyl-phosphonate (e.g., methyl-phosphonate), selenophosphate, phosphoramidate (e.g., N-alkylphosphoramidate), boranophosphonate, and any combinations thereof.

53. The method of any of paragraphs 51-52, wherein the sugar modification is selected from the group consisting of 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH$_2$-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), arabinose sugar, and any combinations thereof.

54. The method of any of paragraphs 51-53, wherein the nucleobase modification is selected from the group consisting of inosine, xanthine, hypoxanthine, nubularine, isoguanisine, tubercidine, 5-methylcytosine (5-me-C); 5-hydroxymethyl cytosine; xanthine; hypoxanthine; 2-aminoadenine; 6-methyl and other 6-alkyl derivatives of adenine and guanine; 2-propyl and other 2-alkyl derivatives of adenine and guanine; 2-thiouracil; 2-thiothymine; 2-thiocytosine; 5-propynyl uracil; 5-propynyl cytosine; 6-azouracil; 6-azocytosine; 6-azothymine; 5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methyl and other 7-alkyl derivatives of adenine and guanine; 8-azaguanine; 8-azaadenine; 7-deazaguanine; 7-deazaadenine; 3-deazaguanine; 3-deazaadenin; universal base; and any combinations thereof.

55. The method of any of paragraphs 51-54, wherein the backbone modification is selected from the group consisting of morpholino, cyclobutyl, pyrrolidine, peptide nucleic acid (PNA), aminoethylglycyl PNA (aegPNA), backnone-extended pyrrolidine PNA (bepPNA), and any combinations thereof.

56. The method of any of paragraphs 45-55, wherein the gene modulator is 15-30 nucleotides in length.

57. The method of any of paragraphs 45-56, wherein the gene modulator inhibits the expression of a gene selected from the group consisting of CCR-5 gene, CD45 gene, TREX1 gene, lamin A gene, EG5 gene, FoxP3 gene, and any combinations thereof.

58. The method of any of paragraphs 45-57, wherein the gene modulator comprises any one or more of the nucleotide sequences selected from the group consisting of SEQ ID NOs: 43-61 and any combinations thereof.

59. The method of any paragraphs 45-58, wherein the aptamer the aptamer directs cell-specific delivery of the conjugate when contacted with a cell.

60. The method of paragraph 59, wherein the cell is a CD4+ cell, a macrophage, or a dendritic cell.

61. The method of any of paragraphs 45-60, wherein the aptamer comprise a nucleotide sequence selected from the group consisting of SEQ ID NOs: 62-66 and any combinations thereof.

62. The method of any of paragraphs 45-61, wherein the conjugates comprises nucleotide sequences selected from: (i) SEQ ID NOs: 58 and 68; (ii) SEQ ID NOs: 58 and 70; (iii) SEQ ID NOs: 59 and 75, 62, and 71; and (iv) SEQ ID NOs: 61 and 67.

63. The method of any of paragraphs 45-62, wherein the conjugate is a conjugate of any of paragraphs 1-24.

64. The method of any of paragraphs 45-63, wherein said administering is intravaginal and/or intrarectal.

65. The method of any of paragraphs 45-64, further comprising a step of selecting the subject by diagnosing the subject with HIV infection or a disease or disorder caused by HIV infection before administering the conjugate.

66. The method of any of paragraphs 45-65, further comprising selecting a subject previously diagnosed with HIV infection or a disease or disorder caused by HIV infection before onset of said administering.

67. The method of any of paragraphs 45-66, wherein the subject is being treated for HIV infection or a disease or disorder caused by HIV infection before onset of said administering.
68. A method of inhibiting the expression of a gene in a CD4+ cell, the method comprising contacting a CD4+ cell with a conjugate comprising an aptamer and a gene modulator, wherein the aptamer is a CD4 aptamer and the gene modulator inhibits the expression of a target gene.
69. The method of paragraph 68, wherein the gene modulator is a siRNA, microRNA, a pre-microRNA, or an antisense.
70. The method of any of paragraphs 68-69, wherein the aptamer and the gene modulator are linked by a phosphodiester, a modified intersugar linkage, a nucleotidic or a non-nucleotidic linker.
71. The conjugate of any of paragraphs 68-70, wherein the gene modulator is linked to 3'-end of the aptamer.
72. The method of any of paragraphs 68-71, wherein the gene modulator is a double-stranded oligonucleotide comprising a sense strand and an antisense strand.
73. The method of paragraph 72, wherein the aptamer is linked to 5'-end of the sense strand.
74. The method of any of paragraphs 68-73, wherein the conjugate comprises a nucleic acid modification selected from the group consisting of internucleotide linkage modification (intersugar linkage modification), sugar modification, nucleobase modification, and any combinations thereof.
75. The method of paragraph 74, wherein the internucleotide linkage modification is selected from the group consisting of phosphorothioate, phosphorodithioate, phosphotriester (e.g. alkyl phosphotriester), aminoalkylphosphotriester, alkyl-phosphonate (e.g., methyl-phosphonate), selenophosphate, phosphoramidate (e.g., N-alkylphosphoramidate), boranophosphonate, and any combinations thereof.
76. The method of any of paragraphs 74-75, wherein the sugar modification is selected from the group consisting of 2'-O-Me (2'-O-methyl), 2'-O-MOE (2'-O-methoxyethyl], 2'-F, 2'-O-[2-(methylamino)-2-oxoethyl] (2'-O-NMA), 2'-S-methyl, 2'-O—CH2-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), arabinose sugar, and any combinations thereof.
77. The method of any of paragraphs 74-76, wherein the nucleobase modification is selected from the group consisting of inosine, xanthine, hypoxanthine, nubularine, isoguanisine, tubercidine, 5-methylcytosine (5-me-C); 5-hydroxymethyl cytosine; xanthine; hypoxanthine; 2-aminoadenine; 6-methyl and other 6-alkyl derivatives of adenine and guanine; 2-propyl and other 2-alkyl derivatives of adenine and guanine; 2-thiouracil; 2-thiothymine; 2-thiocytosine; 5-propynyl uracil; 5-propynyl cytosine; 6-azouracil; 6-azocytosine; 6-azothymine; 5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methyl and other 7-alkyl derivatives of adenine and guanine; 8-azaguanine; 8-azaadenine; 7-deazaguanine; 7-deazaadenine; 3-deazaguanine; 3-deazaadenin; universal base; and any combinations thereof.
78. The method of any of paragraphs 74-77, wherein the backbone modification is selected from the group consisting of morpholino, cyclobutyl, pyrrolidine, peptide nucleic acid (PNA), aminoethylglycyl PNA (aegPNA), backnone-extended pyrrolidine PNA (bepPNA), and any combinations thereof.
79. The method of any of paragraphs 68-78, wherein the gene modulator is 15-30 nucleotides in length.
80. The method of any of paragraphs 68-79, wherein the gene modulator inhibits the expression of a gene selected from the group consisting of CCR-5 gene, CD45 gene, TREX1 gene, lamin A gene, EG5 gene, FoxP3 gene, and any combinations thereof.
81. The method of any of paragraphs 68-80, wherein the gene modulator comprises any one or more of the nucleotide sequences selected from the group consisting of SEQ ID NOs: 43-61 and any combinations thereof.
82. The method of any of paragraphs 68-81, wherein the aptamer the aptamer directs cell-specific delivery of the conjugate when contacted with the cell.
83. The method of any of paragraphs 68-82, wherein the cell is selected from the group consisting of T cells, macrophages, and dendritic cells.
84. The method of any of paragraphs 68-83, wherein the aptamer comprise a nucleotide sequence selected from the group consisting of SEQ ID NOs: 62-66 and any combinations thereof.
85. The method of any of paragraphs 68-84, wherein the conjugates comprises nucleotide sequences selected from: (i) SEQ ID NOs: 58 and 68; (ii) SEQ ID NOs: 58 and 70; (iii) SEQ ID NOs: 59 and 75, 62, and 71; and (iv) SEQ ID NOs: 61 and 67.
86. The method of any of paragraphs 68-85, wherein the conjugate is a conjugate of any of paragraphs 1-24.
87. The method of any of paragraphs 68-86, wherein the target gene is an endogenous gene, a transgene, and/or an exogenous gene.
88. The method of any of paragraphs 68-87, wherein the target gene is selected from the group consisting of a growth factor gene, a growth factor receptor gene, a gene expressing a kinase, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease and any combinations thereof.
89. The method of any of paragraphs 68-88, wherein the gene modulator inhibits the expression of a gene selected from the group consisting of CCR-5 gene, CD45 gene, TREX1 gene, lamin A gene, EG5 gene, FoxP3 gene, a HIV gene, a gene required for HIV replication, a gene required for HIV infection, and any combinations thereof.
90. A method of blocking transmission of HIV into a subject, the method comprising providing an aptamer-gene modulator conjugate to the subject at the site of HIV entry, wherein the aptamer is a CD4 aptamer; and the gene modulator inhibits the expression of HIV gene, a cell gene required for HIV infection, or any combinations thereof.
91. The method of paragraph 90, wherein the gene modulator is a siRNA, microRNA, a pre-microRNA, or an antisense.
92. The method of any of paragraphs 90-91, wherein the aptamer and the gene modulator are linked by a phosphodiester, a modified intersugar linkage, a nucleotidic or a non-nucleotidic linker.

93. The conjugate of any of paragraphs 90-92, wherein the gene modulator is linked to 3'-end of the aptamer.
94. The method of any of paragraphs 90-93, wherein the gene modulator is a double-stranded oligonucleotide comprising a sense strand and an antisense strand.
95. The method of paragraph 94, wherein the aptamer is linked to 5'-end of the sense strand.
96. The method of any of paragraphs 90-95, wherein the conjugate comprises a nucleic acid modification selected from the group consisting of internucleotide linkage modification (intersugar linkage modification), sugar modification, nucleobase modification, and any combinations thereof.
97. The method of paragraph 96, wherein the internucleotide linkage modification is selected from the group consisting of phosphorothioate, phosphorodithioate, phosphotriester (e.g. alkyl phosphotriester), aminoalkylphosphotriester, alkyl-phosphonate (e.g., methyl-phosphonate), selenophosphate, phosphoramidate (e.g., N-alkylphosphoramidate), boranophosphonate, and any combinations thereof.
98. The method of any of paragraphs 96-97, wherein the sugar modification is selected from the group consisting of 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—CH2-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), arabinose sugar, and any combinations thereof.
99. The method of any of paragraphs 96-98, wherein the nucleobase modification is selected from the group consisting of inosine, xanthine, hypoxanthine, nubularine, isoguanisine, tubercidine, 5-methylcytosine (5-me-C); 5-hydroxymethyl cytosine; xanthine; hypoxanthine; 2-aminoadenine; 6-methyl and other 6-alkyl derivatives of adenine and guanine; 2-propyl and other 2-alkyl derivatives of adenine and guanine; 2-thiouracil; 2-thiothymine; 2-thiocytosine; 5-propynyl uracil; 5-propynyl cytosine; 6-azouracil; 6-azocytosine; 6-azothymine; 5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methyl and other 7-alkyl derivatives of adenine and guanine; 8-azaguanine; 8-azaadenine; 7-deazaguanine; 7-deazaadenine; 3-deazaguanine; 3-deazaadenin; universal base; and any combinations thereof.
100. The method of any of paragraphs 96-99, wherein the backbone modification is selected from the group consisting of morpholino, cyclobutyl, pyrrolidine, peptide nucleic acid (PNA), aminoethylglycyl PNA (aegPNA), backnone-extended pyrrolidine PNA (bepPNA), and any combinations thereof.
101. The method of any of paragraphs 90-100, wherein the gene modulator is 15-30 nucleotides in length.
102. The method of any of paragraphs 90-101, wherein the gene modulator inhibits the expression of a gene selected from the group consisting of CCR-5 gene, CD45 gene, TREX1 gene, lamin A gene, EG5 gene, FoxP3 gene, and any combinations thereof.
103. The method of any of paragraphs 90-102, wherein the gene modulator comprises any one or more of the nucleotide sequences selected from the group consisting of SEQ ID NOs: 43-61 and any combinations thereof.
104. The method of any paragraphs 90-103, wherein the aptamer the aptamer directs cell-specific delivery of the conjugate when contacted with the cell.
105. The method of paragraph 104, wherein the cell is a CD4+ cell, a macrophage, or a dendritic cell.
106. The method of any of paragraphs 90-105, wherein the aptamer comprise a nucleotide sequence selected from the group consisting of SEQ ID NOs: 62-66 and any combinations thereof.
107. The method of any of paragraphs 90-106, wherein the conjugates comprises nucleotide sequences selected from: (i) SEQ ID NOs: 58 and 68; (ii) SEQ ID NOs: 58 and 70; (iii) SEQ ID NOs: 59 and 75, 62, and 71; or (iv) SEQ ID NOs: 61 and 67.
108. The method of any of paragraphs 90-107, wherein the conjugate is a conjugate of any of paragraphs 1-24.
109. The method of any of paragraphs 90-108, wherein the site of HIV entry is vaginal or rectal.
110. A kit comprising an aptamer-gene modulator conjugate, wherein the aptamer is a CD4 aptamer and the gene modulator inhibits the expression of a target gene.
111. The kit of paragraph 110, wherein the gene modulator is a siRNA, microRNA, a pre-microRNA, or an antisense.
112. The kit of any of paragraphs 110-111, wherein the aptamer and the gene modulator are linked by a phosphodiester, a modified intersugar linkage, a nucleotidic or a non-nucleotidic linker.
113. The kit of any of paragraphs 110-112, wherein the gene modulator is linked to 3'-end of the aptamer.
114. The kit of any of paragraphs 110-113, wherein the gene modulator is a double-stranded oligonucleotide comprising a sense strand and an antisense strand.
115. The kit of paragraph 114, wherein the aptamer is linked to 5'-end of the sense strand.
116. The kit of any of paragraphs 110-115, wherein the conjugate comprises a nucleic acid modification selected from the group consisting of internucleotide linkage modification (intersugar linkage modification), sugar modification, nucleobase modification, and any combinations thereof.
117. The kit of paragraph 116, wherein the internucleotide linkage modification is selected from the group consisting of phosphorothioate, phosphorodithioate, phosphotriester (e.g. alkyl phosphotriester), aminoalkylphosphotriester, alkyl-phosphonate (e.g., methyl-phosphonate), selenophosphate, phosphoramidate (e.g., N-alkylphosphoramidate), boranophosphonate, and any combinations thereof.
118. The kit of any of paragraphs 116-117, wherein the sugar modification is selected from the group consisting of 2'-O-Me (2'-O-methyl), 2'-O-MOE (2'-O-methoxyethyl), 2'-F, 2'-O-12-(methylamino)-2-oxoethyl] (2'-O-NMA), 2'-S-methyl, 2'-O—CH2-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), arabinose sugar, and any combinations thereof.
119. The kit of any of paragraphs 116-118, wherein the nucleobase modification is selected from the group consisting of inosine, xanthine, hypoxanthine, nubularine, isoguanisine, tubercidine, 5-methylcytosine (5-me-C); 5-hydroxymethyl cytosine; xanthine; hypoxanthine; 2-aminoadenine; 6-methyl and other 6-alkyl derivatives of adenine and guanine; 2-propyl and other 2-alkyl derivatives of adenine and guanine; 2-thiouracil; 2-thiothymine; 2-thiocytosine; 5-propynyl uracil; 5-propynyl cytosine; 6-azouracil; 6-azocytosine; 6-azothymine;

5-uracil (pseudouracil); 4-thiouracil; 8-halo, 8-amino, 8-thiol, 8-thioalkyl, 8-hydroxyl and other 8-substituted adenines and guanines; 5-halo particularly 5-bromo, 5-trifluoromethyl and other 5-substituted uracils and cytosines; 7-methyl and other 7-alkyl derivatives of adenine and guanine; 8-azaguanine; 8-azaadenine; 7-deazaguanine; 7-deazaadenine; 3-deazaguanine; 3-deazaadenin; universal base; and any combinations thereof.
120. The kit of any of paragraphs 116-119, wherein the backbone modification is selected from the group consisting of morpholino, cyclobutyl, pyrrolidine, peptide nucleic acid (PNA), aminoethylglycyl PNA (aegPNA), backnone-extended pyrrolidine PNA (bepPNA), and any combinations thereof.
121. The kit of any of paragraphs 110-120, wherein the gene modulator is 15-30 nucleotides in length.
122. The kit of any of paragraphs 110-121, wherein the gene modulator comprises any one or more of the nucleotide sequences selected from the group consisting of SEQ ID NOs: 43-61 and any combinations thereof.
123. The kit of any paragraphs 110-122, wherein the aptamer the aptamer directs cell-specific delivery of the conjugate when contacted with the cell.
124. The kit of paragraph 123, wherein the cell is a CD4+ cell, a macrophage, or a dendritic cell.
125. The kit of any of paragraphs 110-124, wherein the aptamer comprise a nucleotide sequence selected from the group consisting of SEQ ID NOs: 62-66 and any combinations thereof.
126. The kit of any of paragraphs 110-124, wherein the conjugates comprises nucleotide sequences selected from: (i) SEQ ID NOs: 58 and 68; (ii) SEQ ID NOs: 58 and 70; (iii) SEQ ID NOs: 59 and 75, 62, and 71; and (iv) SEQ ID NOs: 61 and 67.
127. The kit of any of paragraphs 110-126, wherein the conjugate is a conjugate of any of paragraphs 1-24.
128. The kit of any of paragraphs 110-126, wherein the gene modulator inhibits the expression of an endogenous gene, a trans gene, and/or an exogenous gene.
129. The kit of any of paragraphs 110-128, wherein the gene modulator inhibits the expression of a gene selected from the group consisting of a growth factor gene, a growth factor receptor gene, a gene expressing a kinase, an adaptor protein gene, a gene encoding a G protein super family molecule, a gene encoding a transcription factor, a gene which mediates angiogenesis, a viral gene, a gene required for viral replication, a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease and any combinations thereof.
130. The kit of any of paragraphs 110-129, wherein the gene modulator inhibits the expression of a gene selected from the group consisting of CCR-5 gene, CD45 gene, TREX1 gene, lamin A gene, EG5 gene, FoxP3 gene, a HIV gene, a gene required for HIV replication, a gene required for HIV infection, and any combinations thereof
131. To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Materials and Methods
Chimera Synthesis.

Aptamer-siRNA chimera synthesis was modified from previously described methods (McNamara J O 2nd, et al. *Nat Biotechnol.* 2006; 24(8):1005-1015 and Davis K A, Lin Y, Abrams B, Jayasena S D. *Nucleic Acids Res.* 1998; 26(17):3915-3924 3, 17). Primers and template DNAs (Table 1) were commercially synthesized (IDT). RNA intermediates, transcribed in vitro using Epicentre's DuraScribe kit, were resolved on 15% dPAGE gels (Invitrogen) and eluted into either buffer A for in vitro studies (1% $LiClO_4$, 7 mM triethylamine; Sigma-Aldrich) or buffer B for in vivo studies (10 mM Tris, pH 7.5-8.0, 50 mM NaCl, 1 mM EDTA) prior to ethanol precipitation and desalting using a G25 column (GE). RNAs were mixed in a 1:1 molar ratio with commercially synthesized active siRNA strands (Dharmacon), heated to 90° C., and allowed to cool slowly to room temperature. In some cases, the active strand was synthesized with a Cy3 label at its 3' end.

Vaginal Stability Assay.

2 nmol CCR5 CD4-AsiC synthesized using 2'-fluoropyrimidines, chemically stabilized cholesterol-conjugated CCR5-siRNA, and unmodified 21-mer CCR5 siRNA in 100 μl PBS were added to 100 μl of vaginal fluid obtained from a healthy preovulatory donor. At regular intervals, 20 μl was removed, resuspended in TRIzoL reagent (Invitrogen) for RNA extraction, and frozen at −80° C. prior to resolution by PAGE analysis 24 hours after the final collection time point. RNA content was analyzed by densitometry, and amounts were calculated relative to RNA content at time 0.

Cell Lines.

HeLa, Jurkat, and K562 cells (ATCC) were cultured as previously described (Song E, et al. *J Virol.* 2003; 77(13): 7174-7181 and Song E, et al. *Nat Biotechnol.* 2005; 23(6): 709717). HeLa-CD4 and HeLa-MAGI CCR5 cell lines, obtained from the NIH AIDS Reagent Program, were maintained in DMEM supplemented with 0.5 mg/ml G41 8. HCT-116 cells (ATCC) were cultured according to the supplier's instructions. $Dicer^{-/-}$ HCT-116 cells were a gift of B. Vogelstein (Johns Hopkins Medical Institutions, Baltimore, Md., USA; Cummins J M, et al. *Proc Natl Acad Sci USA.* 2006; 103(10):3687-3692).

Primary Cells.

Primary cells from the blood of healthy donors were isolated by Ficoll (GE) density centrifugation and cultured in H10 medium (RPMI 1640 [Cellgro] containing 10% Human AB Serum RiemCelli, 100 I J/ml penicillin, and 100 μg/ml streptomycin sulfate). In some cases, CD4+ cells were separated using immunomagnetic beads (Miltenyi). $CD4^+$ T cells and MDMs were prepared as previously described (Song E, et al. *J Virol.* 2003; 77(13):7174-7181). $CD4^+$ T cells were cultured in H10 containing 60 IU/ml IL-2 and were activated using 4 lig/ml PHA (Difco). Resting PBMCs were cultured in H10 containing 4 fig/ml IL-15.

Viruses.

$HIV_{BaL}$ and HIVniB virus were obtained from the NIH AIDS Reagent Program. I $HV_{BaL}$ was generated by infecting pooled PBMCs that had been stimulated with PITA (4 μg/ml) in H10 plus 60 'Wm' rIL-2 (Chiron). HIVIIIB was propagated as previously described (Brass A L, et al. Science. 2008; 319(5865):921-926). p24 Ag levels in culture supernatants were measured by HIV-1 p24 Antigen ELISA kit (Perkin Elmer). VSV(G)-pseudotyped HIV-Luc (provided by A. Engelman; Dana-Farber Cancer Institute, Boston, Mass., USA) was generated in 239T cells as previously described (Shun M C, et al. *Genes Dev.* 2007; 21(14):1767-1778). Viral stocks of the HIV-$1_{R\_em}$ molecular clone were produced through transfection of HEK293 cells as previously described (Boutwell C L, Rowley C F, Essex M. *J Virol.* 2009; 83(6):2460-2468). Supernatant virus was concentrated 1:50 using the PEG-it Virus Precipitation Solution (System Biosciences) per the manufacturer's protocol.

HIV-1 Infection In Vitro and In Situ.

Cells were infected with the indicated HIV-1 isolates using an MOI of approximately 1. Infection of Jurkat and CD4$^+$ T cells was by spinoculation at 1,200 g for 2 hours in the presence of 2 mg/ml Polybrene. HeLa-CD4 and MDM cells were infected by incubating the cells with virus at 37° C. for 48 hours. Cells were infected with the single-round VSV(G)-pseudotyped virus for 6-8 hours at 37° C., washed, and incubated again at 37° C. in fresh media for approximately 48 hours prior to analysis as previously described (Shun M C, et al. *Genes Dev.* 2007; 21(14):1767-1778). For HIV infection of polarized explants, HIV$_{BaL}$ (~100 ng p24) was applied to the apical surface of agarose-embedded explants in 200 ttl, and the explants were then incubated at 37° C. Viral replication in the tissue was assessed by measuring p24 Ag in the lower transwell chamber using the HIV-1 p24 Antigen ELISA kit (Perkin Elmer).

siRNA Transfection.

HeLa-CD4 and MDM cells were transfected with Oligofectamine per the manufacturer's protocol. CD4$^+$ T cells, Jurkat cells, and K562 cells were transfected by AMAXA according to the manufacturer's protocol (Lonza). Table 3 for all siRNA sequences.

Flow Cytometry.

Direct immunostaining of CD3, CD4, CD8, CD14, CD45, and CCR5 was performed using 1:20 dilutions of murine mAb for 30-60 minutes at 4° C. (BioLegend). Cells were stained in PBS containing 0.5% FCS, 1 mM EDTA, and 25 mM HEPES. Samples were washed twice in the same buffer. Data for 1- and 2-color staining experiments were acquired using FACSCalibur (BD Biosciences); for multicolor experiments, data were acquired using FACS-Canto 11 (BD Biosciences). All data analysis was performed using FlowJo (Treestar Inc.).

Fluorescence Microscopy.

Fluorescence microscopy was performed as previously described (Wu Y, et al. *Cell Host Microbe.* 2009; 5(1):84-94) using primary antibodies (BioLegend) and secondary donkey anti-mouse antibodies (Invitrogen). All images were acquired using a ×60 oil objective.

Intracellular p24 Staining.

Intracellular staining, performed as previously described (Song E, et al. *J Virol.* 2003; 77(13):7174-7181), was analyzed on a FACSCalibur with Cell Quest software (Becton Dickinson) and/or FlowJo software. The p24 MFI was normalized relative to the mock-treated control.

Immunoblot.

Total cell extracts were prepared in RIPA buffer (50 mM Tris-HCl pH 7.4, 150 mM NaCl, 1 mM EDTA, 1% Triton X-100, 1% sodium deoxycholate, 0.1% SDS). Protein concentration was measured using the BCA Protein Assay Reagent (Pierce), and 10 tig of total protein was resolved on 10% SDS-PAGE, transferred to cellulose membranes (Immobilon-P, Millipore), and probed with mouse mAb against lamin A (BioLegend). The membranes were developed using SuperSignal West Femto (Pierce). For loading control, 10 μg of total protein was resolved on 10% SDS-PAGE and probed using anti-tubulin mouse mAb (Sigma-Aldrich).

In Vitro Dicer Cleavage Assay.

Recombinant Dicer cleavage assay was performed using the Turbo Dicer siRNA Generation Kit (Genlantis) according to the manufacturer's protocol.

5'-RACE and Sequence Analysis

5'-RACE was performed using the First Choice RLM-RACE Kit (Ambion) according to the manufacturer's protocol, modified to use 45 cycles of amplification for the nested PCR reaction. The nested PCR product was cloned using standard M13 and T7 primers into the PGEM-T Easy vector (Promega) for sequencing at the Dana-Farber Harvard Cancer Center Sequencing Core (Boston, Mass., USA).

Luciferase Assay.

The luciferase activity of VSV(G)-pseudotyped reporter virus—infected samples was measured 48 hours after transfection using the Luciferase Assay System (Promega) and a Top count NXT microplate reader (Perkin Elmer) per the manufacturer's instructions. Background luminescence was subtracted from all values, and data were normalized relative to mock-treated controls.

Qrt-PCR.

qRT-PCR was performed as previously described (Palliser D, et al. *Nature.* 2006; 439(7072):89-94.) using primers in Table 2. mRNA expression was normalized to GAPDT-I, then calculated as a percentage relative to mock-treated controls.

Human Cervical Polarized Tissue Explants.

Human cervical tissue was obtained from healthy human donors undergoing hysterectomy for benign conditions. Tissue was immediately sectioned into approximately 3-mm$^3$ specimens and then oriented with the apical epithelial surface facing up on the membrane of a 12-transwell system (Corning). Explants were then embedded in 3% agarose as described previously (Collins K B, Patterson B K, Naus G J, Landers D V, Gupta P. *Nat Med.* 2000; 6(4):475-479), and the integrity of the agarose seal was tested using Trypan blue. The polarized explants were cultured in 200 μl H10 medium. Cy3-labeled AsiCs in 50 μl Optimem (Invitrogen) were applied to the apical surface, and the explants were then incubated at 37° C. for 4-6 hours before adding 150 [d H10 to each well. The treatment was repeated 24 hours later, then the tissue was incubated for an additional 48 hours at 37° C. prior to collagenase digestion and analysis. All tissues were obtained anonymously and were considered exempt from informed consent. Approval was obtained from the IRBs of Massachusetts General Hospital and Brighan and Women's Hospital. Human tissues from Beth Israel Deaconess Medical Center were deemed exempt from IRB approval. E. Oliva (Massachusetts General Hospital, Boston, Mass., USA) provided some of the human samples.

Collagenase Digestion of Human and Mouse Vaginal Tissue.

48 hours after the second application of RNA, specimens were removed from the transwell. 10 polarized explants per treatment condition were pooled and digested in 10 ml RPMI containing 1 mg/ml collagenase II (Sigma-Aldrich) for 30 minutes at 37° C. with shaking. Samples were disrupted in a gentleMACS dissociator (Miltenyi) using the C.01 program for 30 minutes at 37° C. both before and after collagenase digestion. Cell suspensions were passed through a 70-pm cell strainer (BD Falcon), washed with 30 ml RPMI, and stained for flow cytometry.

Hematoxylin and Eosin Staining.

Explants treated for 24 hours with 4 µM AsiCs were fixed in 3.7% formalin (Sigma-Aldrich) and paraffin embedded. 5-gm tissue sections were stained with hematoxylin and eosin (ThermoFisher Scientific). Images were acquired using a Zeiss Axiovert 200M microscope and Slidebook software (Intelligent Imaging).

Cytotoxicity Assay.

Cellular cytotoxicity was quantified by measuring LDH release into the culture medium using the Roche LDH assay according to the manufacturer's instructions. Briefly, 100 pl of culture medium harvested 24 hours after treatment was mixed with 100 pl LDH reaction mix and incubated for 30 minutes at room temperature. Absorbance at 490 nm was measured using a Spectra MAX 340PC microplate counter (Molecular Devices) and normalized to absorbance at 650 nm. Culture medium from tissue treated with 1% Triton X-100 (ThermoFisher Scientific) served as a positive control.

IFN and Cytokine Induction.

An equimolar mixture of CD4-AsiC or PSMA-AsiC targeting gag and vif (total concentration 4 µM) was applied to the apical surface of the explant, and RNA was extracted using TRIzoL reagent (Invitrogen) 6 and 24 hours later. Treatment with poly(I:C) (50 µg/ml; Invivogen) served as a positive control. qRT-PCR was performed as above (see Table 2 for primers). mRNA expression was normalized to GAPDH, then normalized relative to mock-treated controls.

In Vivo Treatment and HIV Challenge.

All in vivo experiments were performed using immunodeficient mice bearing human bone marrow (either NOD/SCID or NSG) following reconstitution with $CD34^+$ cells from human fetal liver and surgical human thymic graft (i.e., BLT mice) as previously described (Brainard D M, et al. *J Virol.* 2009; 83(14):7305-7321.). Uptake and silencing was assessed in NOD/SCID-BLT mice following 2 IVAG treatments of Cy3-labeled AsiCs, at the indicated doses, 72 hours and 48 hours prior to sacrifice. Vaginal tissue was extracted, and a single-cell suspension was isolated by collagenase digestion and stained as described above. HIV protection was assessed in NSG-BLT mice treated IVAG (a) 48 hours before challenge with 10 µl PBS containing 80 pmol CCR5 CD4-AsiCs; (b) 24 hours before challenge with 10 pl PBS containing 40 pmol each of CCR5, gag, and vif CD4-AsiCs; and (c) 4 hours after challenge with 10 pl PBS containing 40 pmol each of gag and vif CD4-AsiCs. Female mice were challenged with atraumatic IVAG instillation of $10^5$-$TCID_{50}$ $HIV_{JR\_csF}$ in 10 pl PBS as previously described (Denton P W, et al. *PLoS Med.* 2008; 5(1):e16). Animal work was approved by the Animal Care and Use Committees of Massachusetts General Hospital and Harvard Medical School.

Analysis of HIV Infection.

Blood was obtained by venipuncture at weekly intervals for 12 weeks after HIV challenge. Cells were pelleted by centrifugation, and plasma was stored at −80° C. until analysis. Cell pellets were twice treated with rbc lysis buffer (Sigma-Aldrich), washed with flow cytometry buffer described above, and stained for CD3, CD4, and CD8. Viral RNA was extracted from 75 µl plasma using the QiaAmp Viral RNA kit (QIAGEN) according to the manufacturer's instructions. eDNA was reverse transcribed using Superscriptlll (Invitrogen) and HIV-gag—specific primers (Supplemental FIG. 2) according to the manufacturer's protocol. qRT-PCR was performed as described above. The remaining serum was aliquoted for p24 Ag ELISA (Perkin Elmer), performed according to the manufacturer's instructions.

Statistics.

Data for most experiments were analyzed by Student's t test. All P values are for 2-tailed significance tests. For analysis of data based on independent experiments using samples from multiple donors, 1-way ANOVA with Dunnett multiple-comparison test was performed using GraphPad Prism (GraphPad Software). Assessment of HIV infection was by 2-way ANOVA with Dunnett multiple-comparison test. P values less than 0.05 were considered significant. The limit of detection was calculated using a previously described method (Armbruster D A, Pry T. *Clin Biochem Rev.* 2008; 29(suppl 1):S49-552) and is shown as the average of the calculated limit of detection for each individual assay.

Results and Discussion

Chimeric RNAs, composed of an siRNA fused to an aptamer (a structured RNA selected to bind a cell surface ligand with high affinity), provide an attractive alternative for in vivo gene knockdown (de Fougerolles, A. et al., *Nat Rev Drug Discov,* 6, 443-453 (2007); McNamara, J. O., 2nd et al. *Nat Biotechnol* 24, 1005-1015 (2006); Dassie, J. P. et al. *Nat Biotechnol* 27, 839-849 (2009); Zhou, J., et al. *Mol Ther* 16, 1481-1489 (2008); Zhou, J. et al. *Nucleic Acids Res* 37, 3094-3109 (2009)). Aptamer-siRNA chimeras (AsiCs) efficiently transfect and knockdown gene expression in cells bearing the surface receptor the aptamer recognizes. Intravenous injection of AsiCs incorporating aptamers targeting prostate surface membrane antigen (PSMA) silence target gene expression in orthotopic prostate cancer mouse xenografts (McNamara, J. O., 2nd et al. *Nat Biotechnol* 24, 1005-1015 (2006); Dassie, J. P. et al. *Nat Biotechnol* 27, 839-849 (2009)). AsiCs containing an aptamer that recognizes HIV-120 inhibit HIV replication in already infected cells in vitro (Zhou, J., et al. *Mol Ther* 16, 1481-1489 (2008); Zhou, J. et al. *Nucleic Acids Res* 37, 3094-3109 (2009)). However, to prevent HIV transmission, it might be better to inhibit de novo infection of uninfected cells. Accordingly, the invention provides aptamer-siRNA conjugates and methods for cell-specific transfection of immune cells, which can inhibit de novo infection of uninfected cells.

Synthesis and Purification of CD4-AsiCs.

Figure 5A:
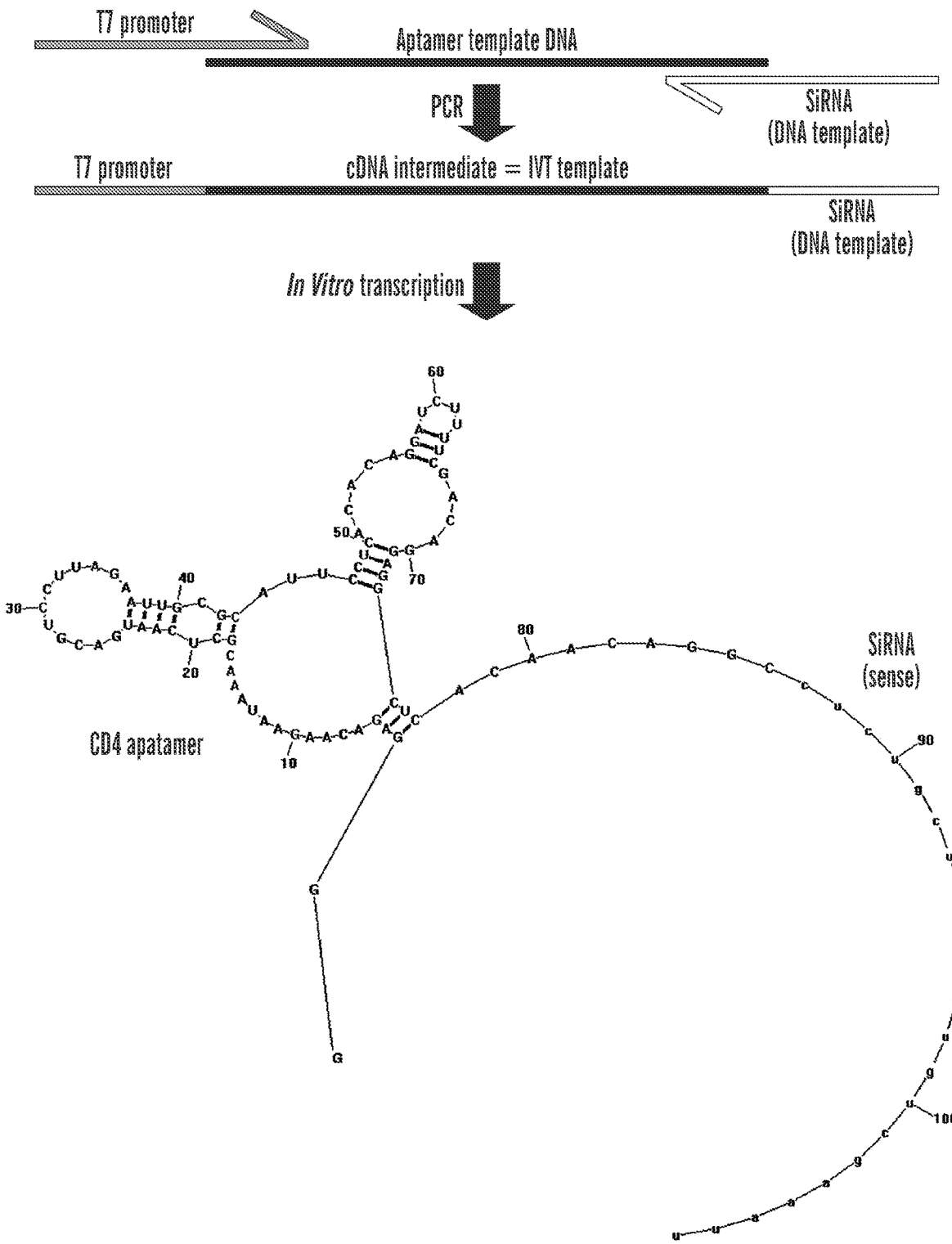
FIG. 5A is a schematic of the synthesis of aptamer-siRNA chimeras (AsiC). AsiC were synthesized from a DNA oligomer, encoding previously described CD4 aptamers (Davis K A, Lin Y, Abrams B, Jayasena S D. Nucleic Acids Res. 1998; 26(17):3915-3924), which was PCR amplified to introduce a 5'-T7 RNA polymerase promoter sequence and an siRNA sense strand at the 3'-end. From this cDNA intermediate, an ssRNA that bears the sense (passenger) strand of an siRNA at its 3' end was generated by in vitro transcription (IVT). This ssRNA was annealed to a commercially synthesized anti-sense siRNA strand.
Figure 5A:
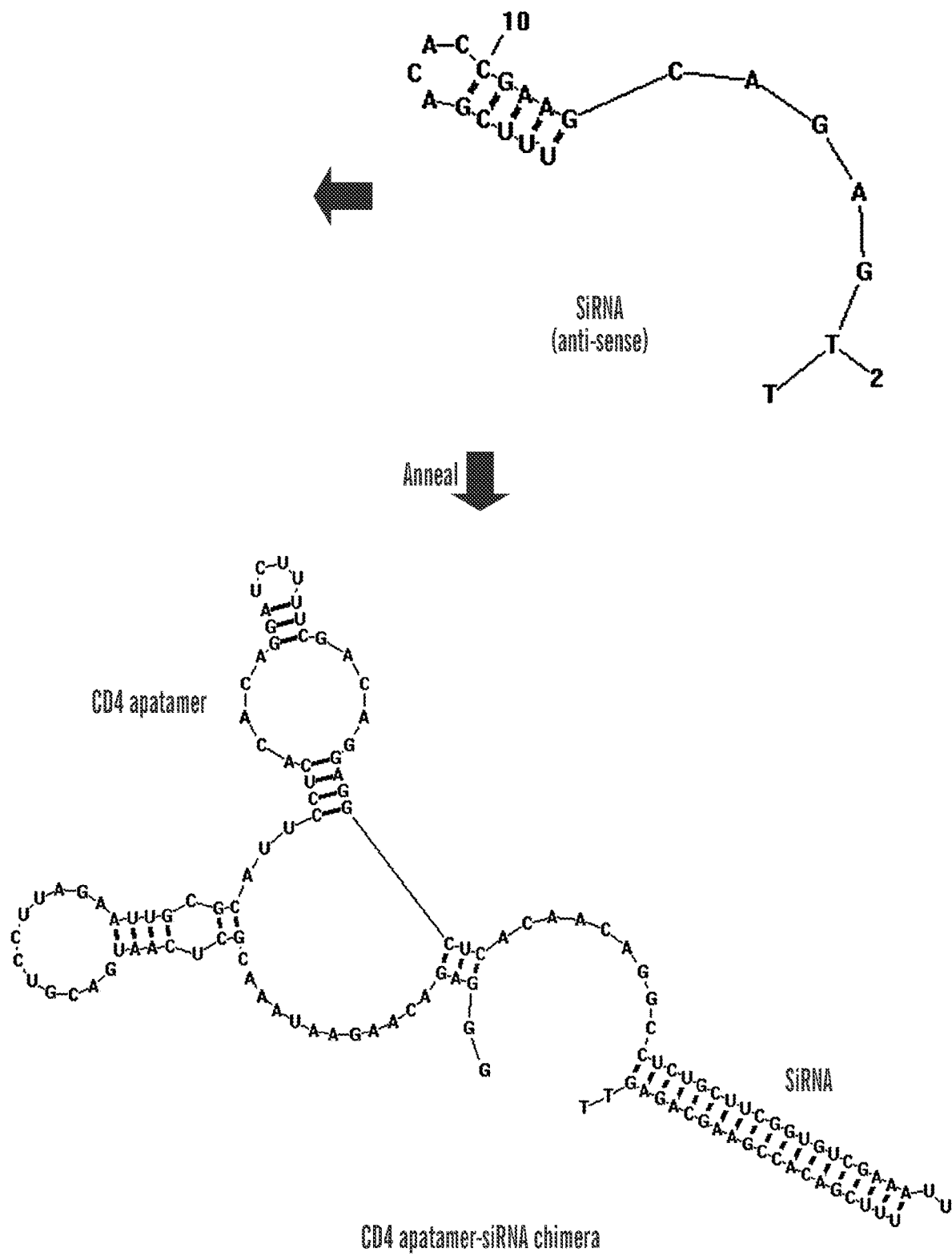
Figure 5B:
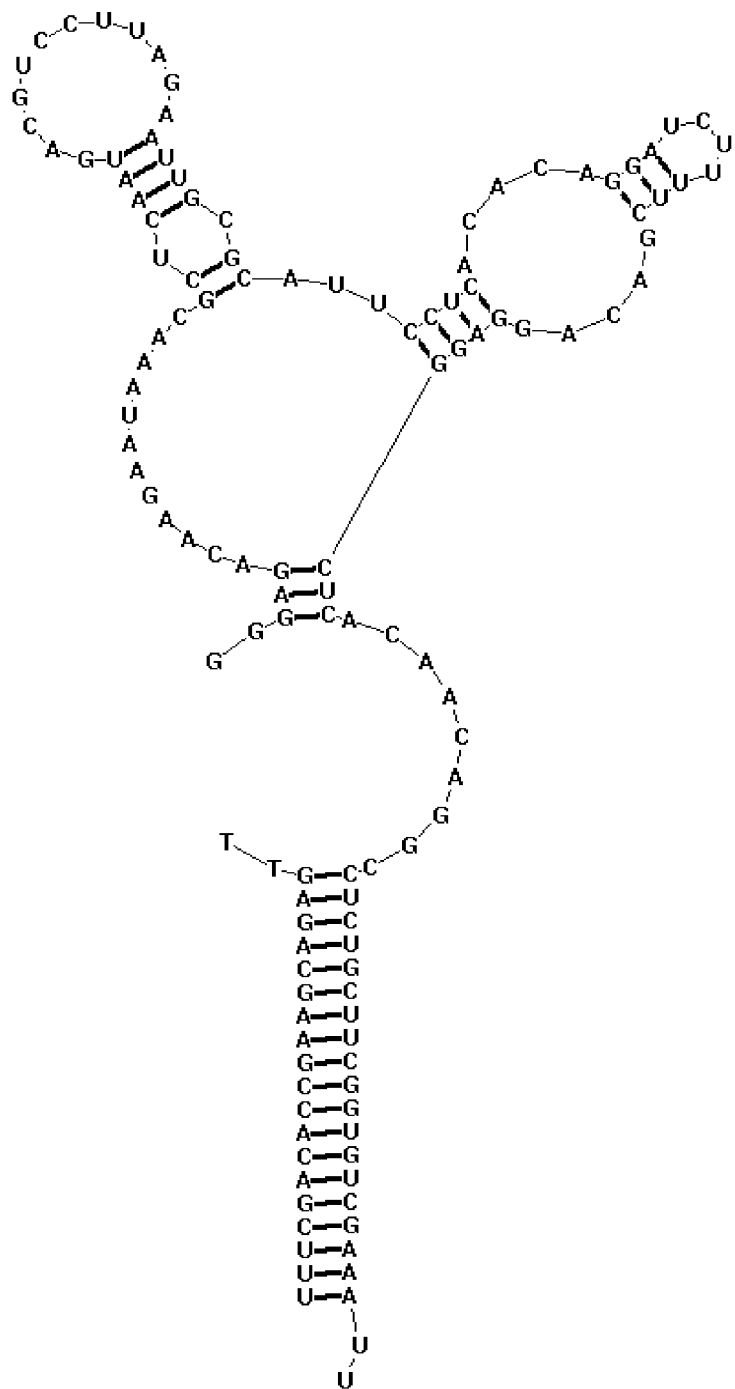
FIGS. 5B and 5C show the predicted secondary structures for two chimeras, each containing a specific CD4-aptamer clone, clone 9 (FIG. 5B) and clone 12 (FIG. 5C) from 3, linked to a CCR5-siRNA duplex at their 3'-end. Sequences shown are SEQ ID NO: 68 (aptamer clone 9+ sense) and SEQ ID NO: 58 (antrisense) (FIG. 5B) and SEQ ID NO: 70 (aptamer clone 12+ sense) and SEQ ID NO: 58 (antisense) (FIG. 5C).
Figure 5C:
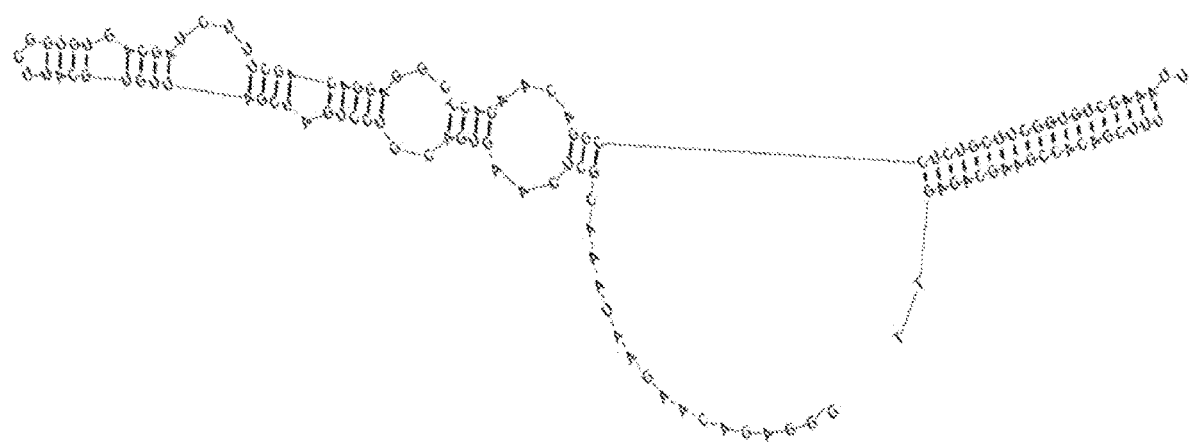
Figure 6A:
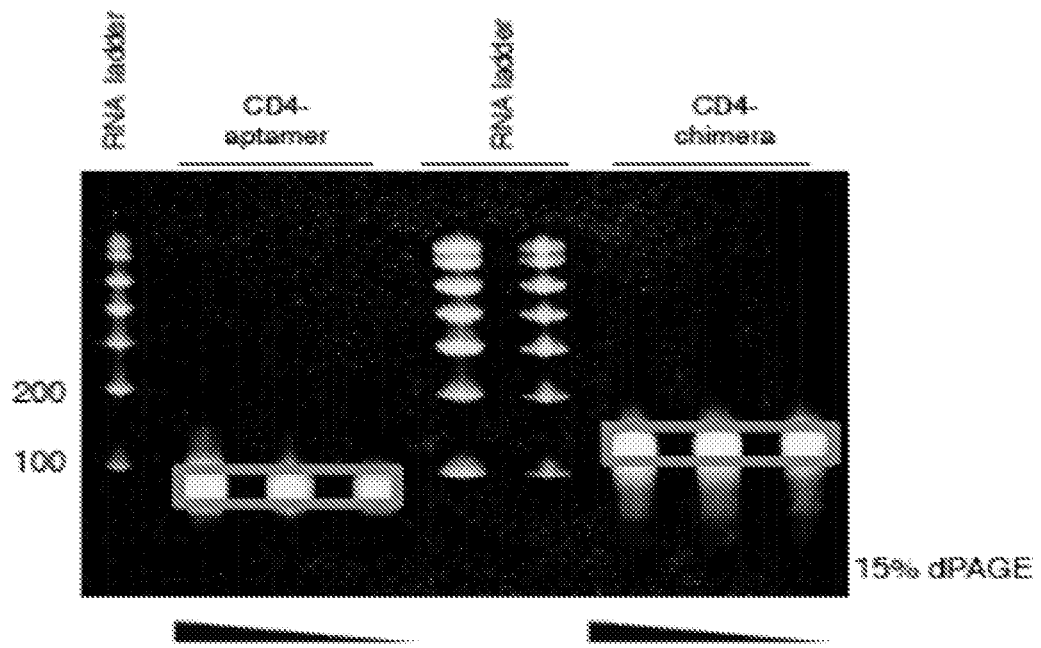
FIGS. 6A and 6B show the characterization of the in vitro transcribed (IVT) CD4-AsiC.
Figure 6B:
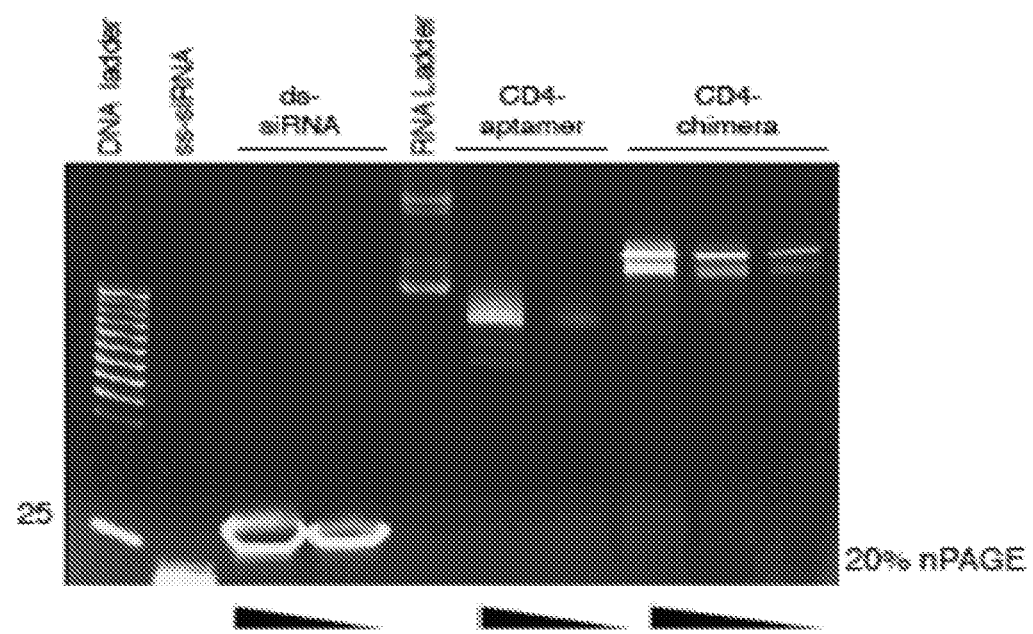
Figure 16A:
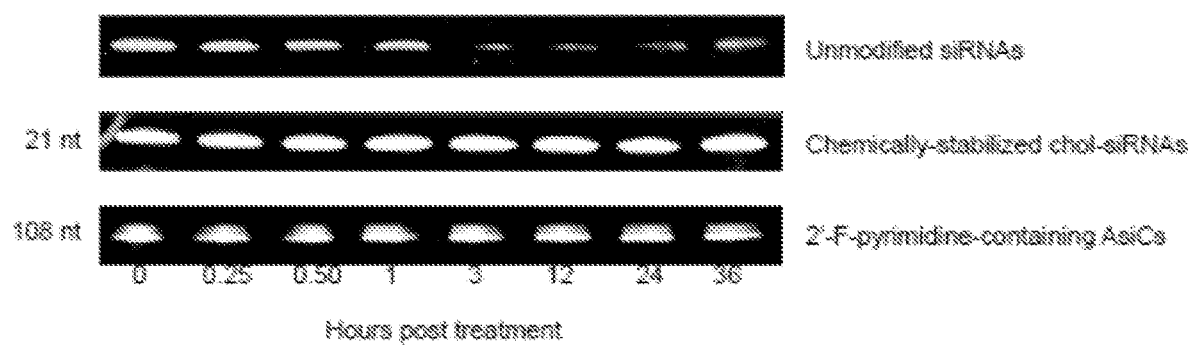
FIGS. 16A and 16B show that CD4-AsciCs are stable in vaginal fluids. Two nmols of AsiCs synthesized using 2'-fluoro-pyrimidines, chemically-stabalized 21-mer chlosteril-conjugated CCR5-siRNAs (chol-siRNA), and unmodified 21-mer CCR siRNAs, each in 100 uL PBS were added to 100 uL of vaginal fluid obtained from a healthy pre-ovulatory patient to a final volume of 200 uL and incubated at 37° C. At each indicated timepoint, 20 uL were removed from each tube, resuspended in Trizol reagent (Invitrogen), and froze at −80° Celsius. One day following the final timepoint, the RNA was extracted from the Trizol for each sample as per the manufacturer's instructions, resuspended in 20 uL distilled water+5 uL gel loading buffer, and resolved on a PAGE gel. All results were quantified by dosimetry and divided by the baseline amount at time 0 to give a percentage remaining over time. Representative PAGE gels (FIG. 16A) and the average inensity (±SEM) of two hands from two independent experiments (FIG. 16B) analyzed by densitometry are shown. Both the stabilized cholesterol conjugated siRNA and CD4-Asci are stable over the 36 h of experiment, but unmodified siRNAs have a half-life in vaginal fluid of between 3 and 10 h.
Figure 16B:
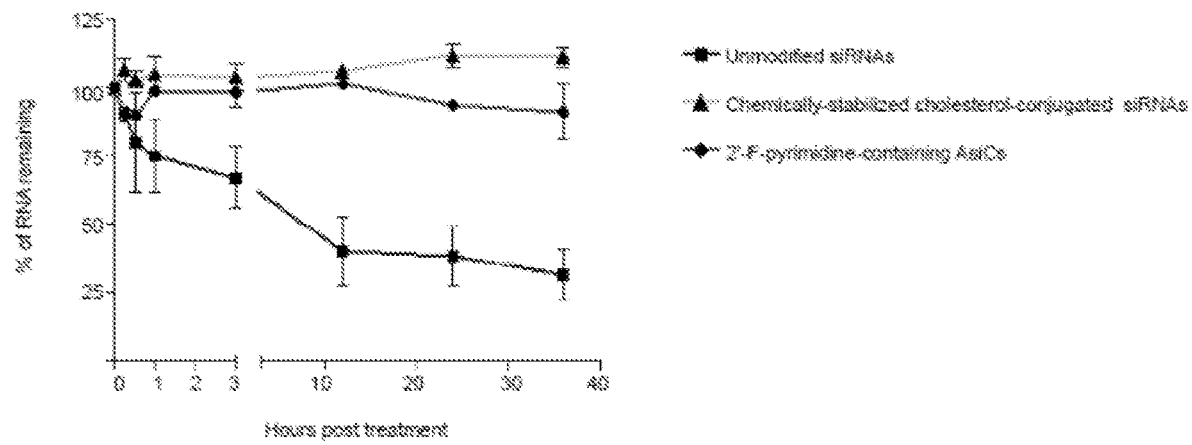

CD4-AsiCs were designed with a CD4 aptamer at the 5'-end ligated to the sense (inactive) siRNA strand (FIGS. 1A and 5A). These were in vitro transcribed (IVT) from a PCR template, using 2'-fluoropyrimidines to enhance stability (FIG. 16) and reduce stimulation of immune sensors that detect foreign nucleic acids. Transcripts were eluted from denaturing SDS-PAGE gels and analyzed by column chromatography and native SDS-PAGE gels (FIG. 6), before annealing the antisense (active) siRNA strand. A chimera using an aptamer targeting prostate specific membrane antigen (PSMA) (McNamara, J. O., 2nd et al. *Nat Biotechnol* 24, 1005-1015 (2006)), was synthesized as a binding control, while scrambled siRNA sequences controlled for gene silencing specificity. CD4-AsiCs engineered with one of the aptamers (clone 9) was consistently more effective than the other (clone 12) (Davis, K. A. et al. Nucleic Acids Res 26, 3915-3924 (1998)) (FIGS. 5B and 5C, and data not shown) and was used for most experiments unless otherwise indicated. Sequences of clone 9 and clone 12 are shown in FIGS. 5B and 5C respectively.

CD4-AsiCs are taken up by primary CD4+ cells in vitro.

Figure 1B:
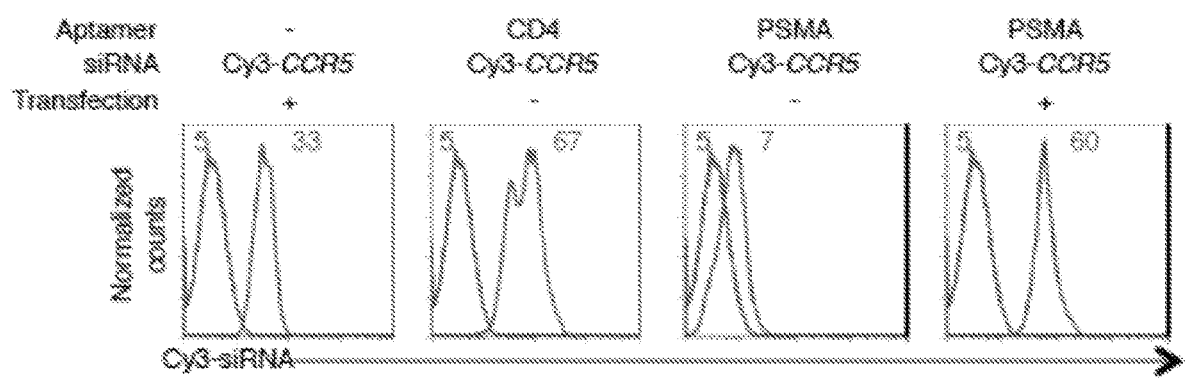
Figure 1C:
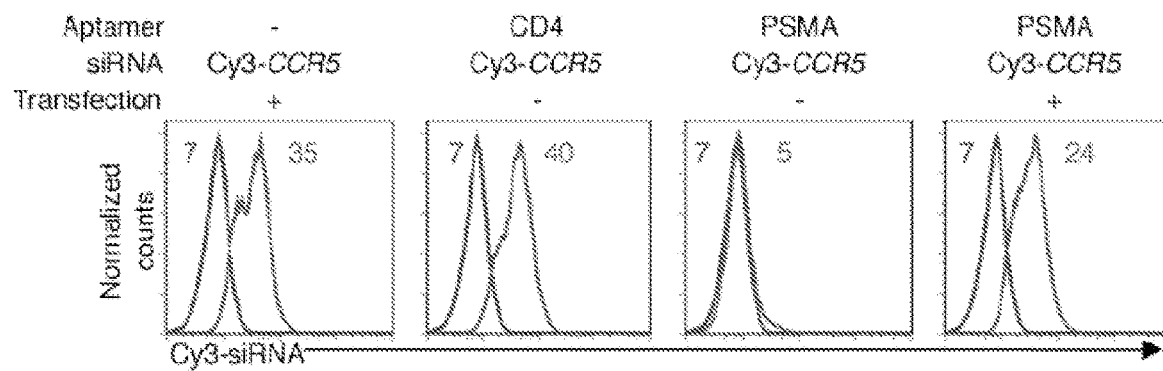
Figure 1D:
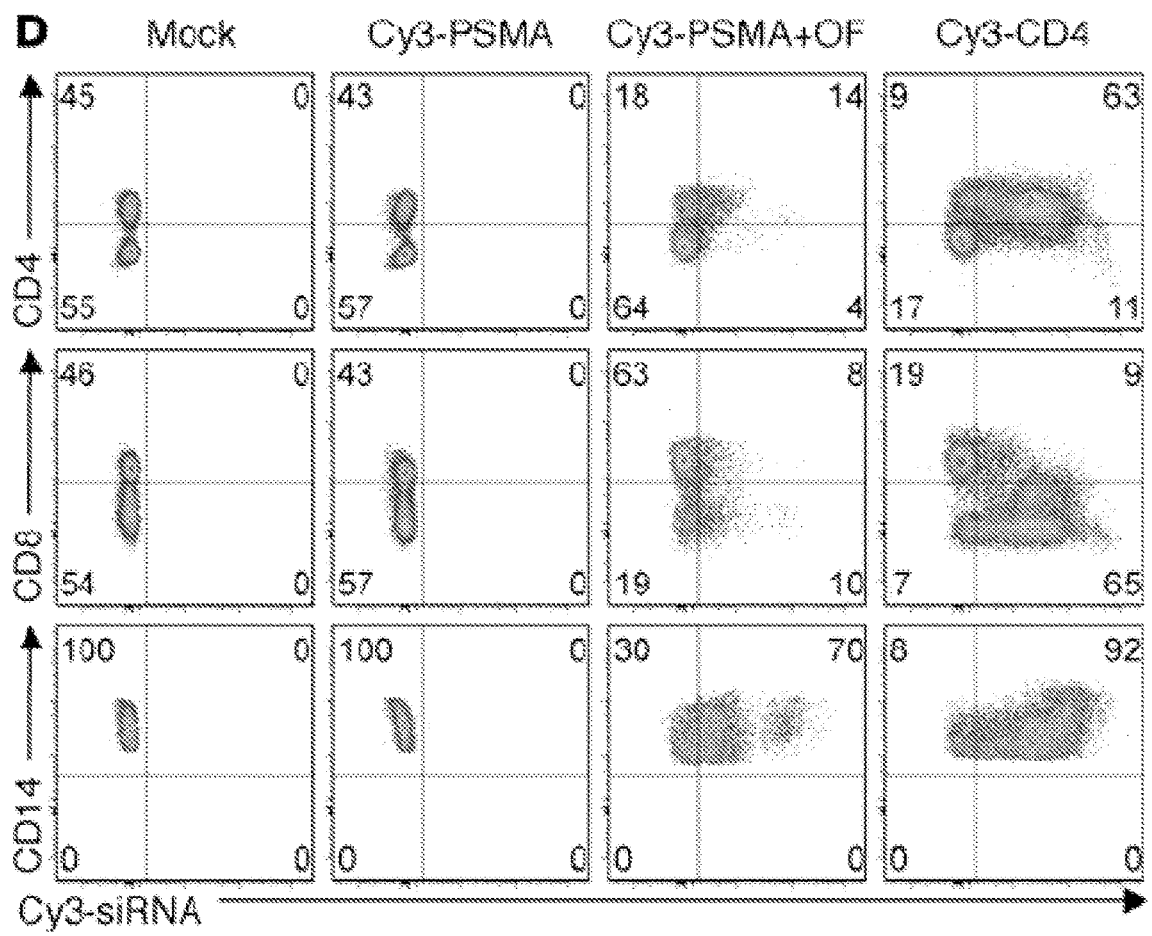

To test for siRNA uptake into CD4+ cells, primary monocyte-derived macrophages (MDMs) and CD4+ T cells freshly isolated from the blood of healthy donors were incubated with CD4-AsiCs labeled with Cy3 at the 3' terminus of the antisense strand. CD4-AsiCs were efficiently and uniformly taken up by both MDMs (FIG. 1B), and CD4+ T cells (FIG. 1C). Uptake was assessed by flow cytometry (FIGS. 1B and 1C) and fluorescence microscopy (data not shown). In fluorescence microscopy experiments, cells were labeled with DAPI and CD4-AF488. Only Cy3-labeled siRNA conjugated with CD4 aptamer or transacted with a transfection reagent was uptaken by the cells (data not shown); Cy3-labeled siRNA conjugated with the PSMAn aptamer was not seen to be uptaken by the cells (data not shown). PSMA-AsiCs were not internalized without transfection (complexation with a transfection lipid for MDMs or electroporation for T cells). When added to resting peripheral blood mononuclear cells (PBMCs), Cy3-labeled CD4-AsiCs were selectively taken up by CD4+ monocytes and T cells, but only to a limited extent by CD8+ T cells (FIG. 1D). Without wishing to be bound by a theory, the small subpopulation of circulating CD8 T cells that took up the Cy3-labeled CD4-AsiCs can represent recently activated CD8 T cells that express low levels of CD4 (data not shown). PSMA-AsiCs on their own were not internalized by any immune cells, except as lipoplexes. In that case, the fluorescent RNA was internalized by CD14+ monocytes, but not by CD3+ lymphocytes, which are refractory to lipid-based transfection.

CD4-AsiCs Knock Down Target Gene Expression in Primary CD4+ Cells in Vitro in a Dose-Dependent Manner.

Figure 2A:
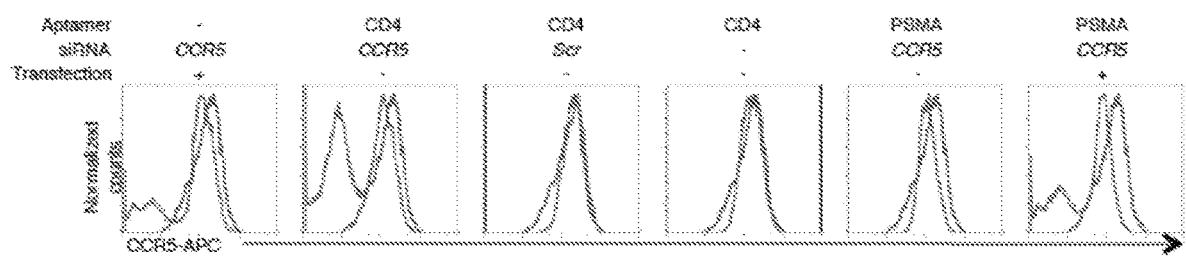
FIGS. 2A-2D show that CD4 aptamer-siRNA chimera (CD4-AsiC) knocks down CCR5 in primary MDM and CD4 lymphocytes in vitro. Primary MDMs (FIGS. 2A-2B) and CD4 T-lymphocytes (FIGS. 2C-2D) were treated with either CD4- or PSMA-AsiCs against CCR5 or containing a scrambled siRNA sequence (Scr), or CD4-aptamers alone, in the presence or absence of transfection (OF, FIGS. 2A-2C; nucleofection 2D and 2E). Shown are representative flow cytometry histograms of CCR5 expression (FIGS. 2A and 2C) (mock treated cells, blue; treated cells, red) and the mean (±S.E.M.) relative mean fluorescence intensity (MFI) for five healthy human subjects, normalized to the mock-treated sample (FIGS. 2B and 2D). (*p<0.005; p<0.0005; and *p<0.00005, 2-tailed t test). Without transfection, CCR5 was knocked down only in cells treated with the CCR5 CD4-AsiC. CCR5 knockdown in MDMs was confirmed by fluorescence microscopy, comparing mock treated cells, to cells either transfected with Cy3-labeled siRNA using OF or treated with 4 µM Cy3-labeled CD4-AsiC (data not shown).
Figure 2B:
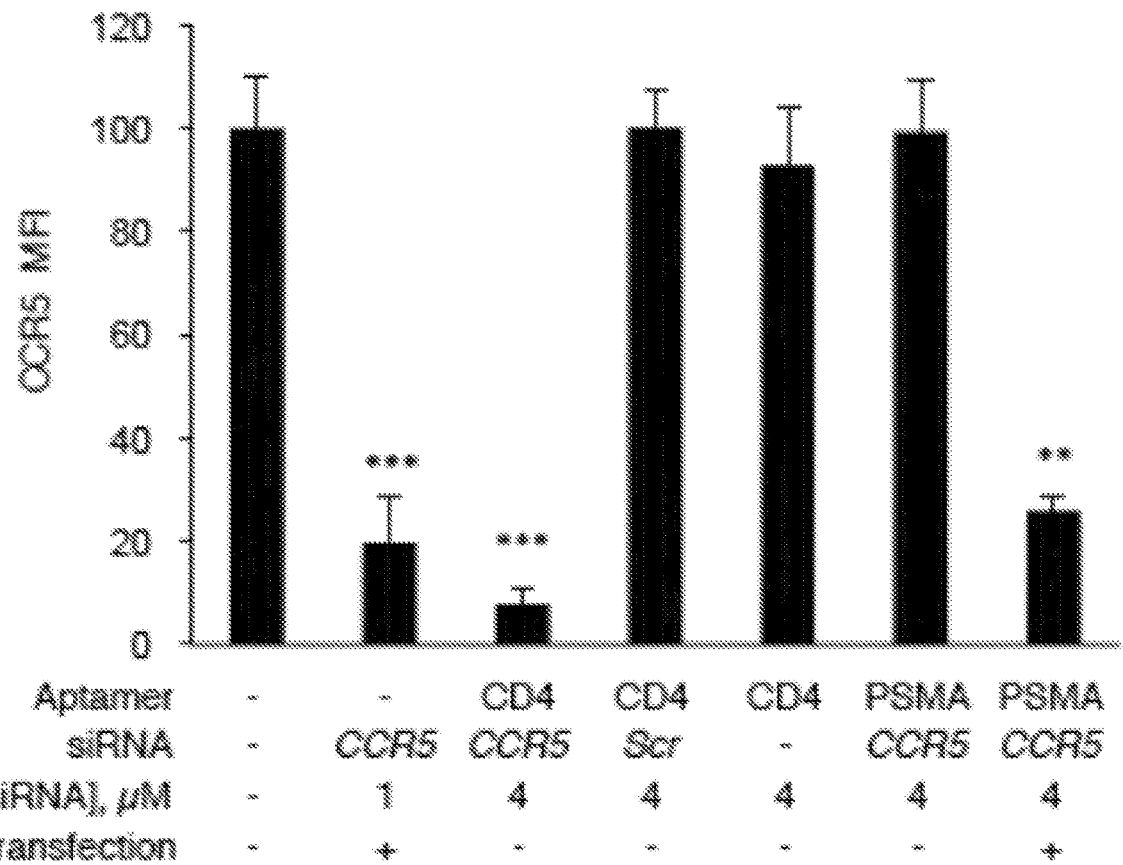
Figure 2C:
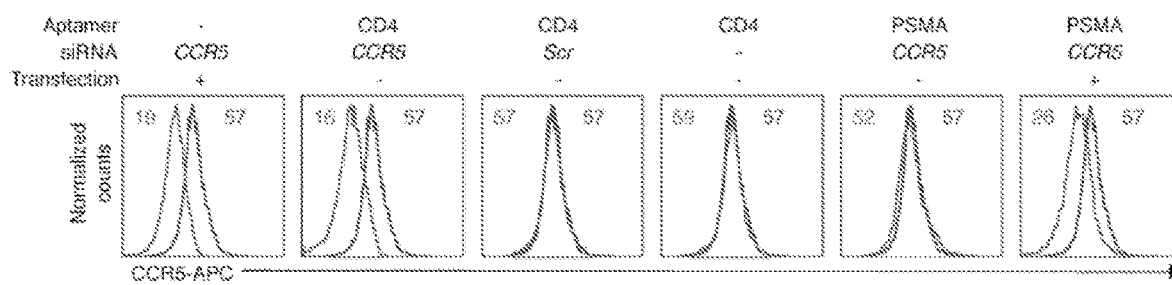
Figure 2D:
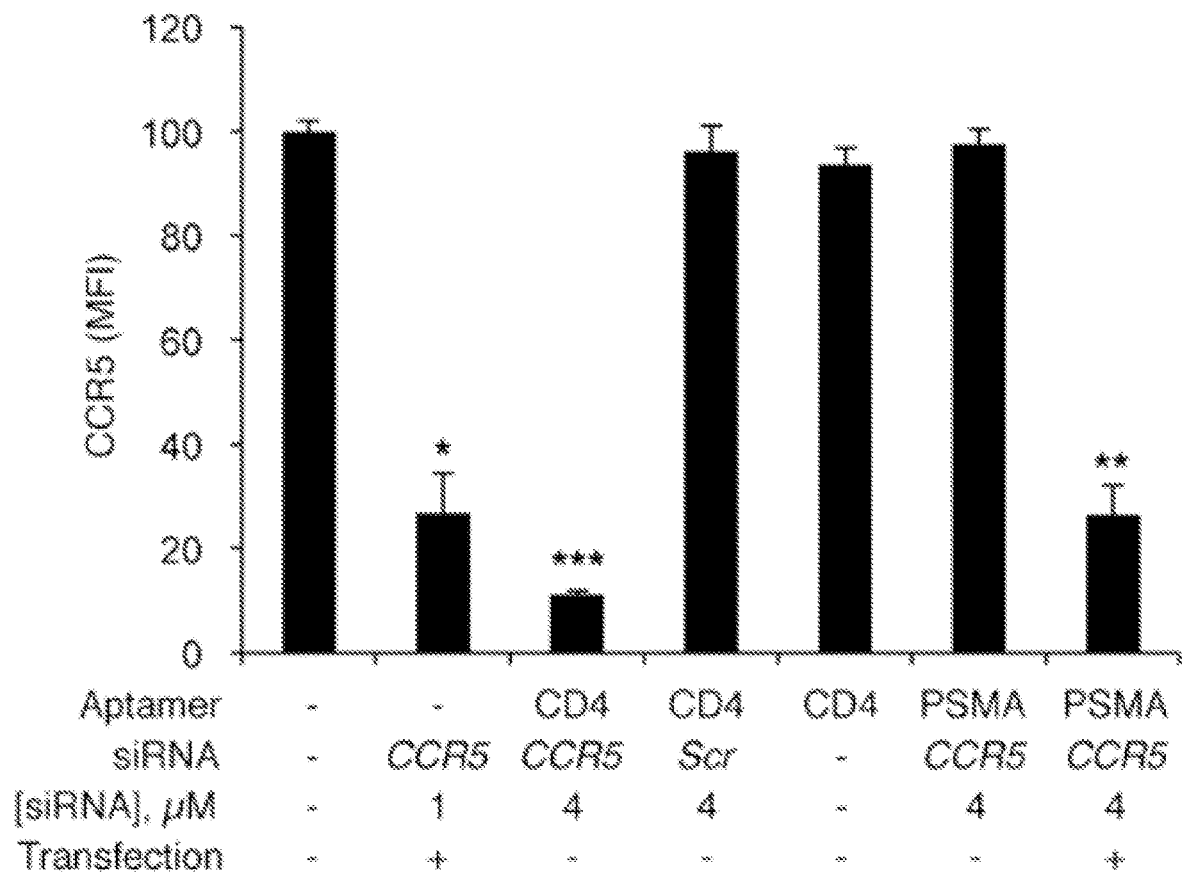

After showing selective uptake by CD4+ immune cells, gene silencing was evaluated. Primary CD4+ cells were treated with CD4-AsiCs bearing a CCR5 siRNA, and CCR5 expression was quantified by flow cytometry. CCR5 was knocked down in both MDMs (FIGS. 2A and 2B) and CD4 T cells (FIGS. 2C and 2D). Gene silencing was specific since CCR5 expression was unchanged when chimeras containing a scrambled siRNA sequence or the PSMAn aptamer were tested, or when cells were incubated with the CD4 aptamer alone. Transfection of the CCR5 PSMA-AsiC knocked down CCR5 expression in both cell types. Although silencing in CD4+ T cells was uniform, two populations of MDMs were observed; in one population knockdown was virtually complete, while in the other CCR5 was only partially down-modulated. These two populations were also seen with lipid transfection. The reason for this is unclear, but is unlikely to be secondary to differential uptake since uptake of Cy3-labeled CD4-AsiCs was uniform in macrophages (FIG. 1B). CCR5 knockdown in MDMs was also confirmed by fluorescence microscopy, comparing mock treated cells, to cells either transfected with Cy3-labeled siRNA using OF or treated with 4 µM Cy3-labeled CD4-AsiC (data not shown).

Figures 7A, 7B:
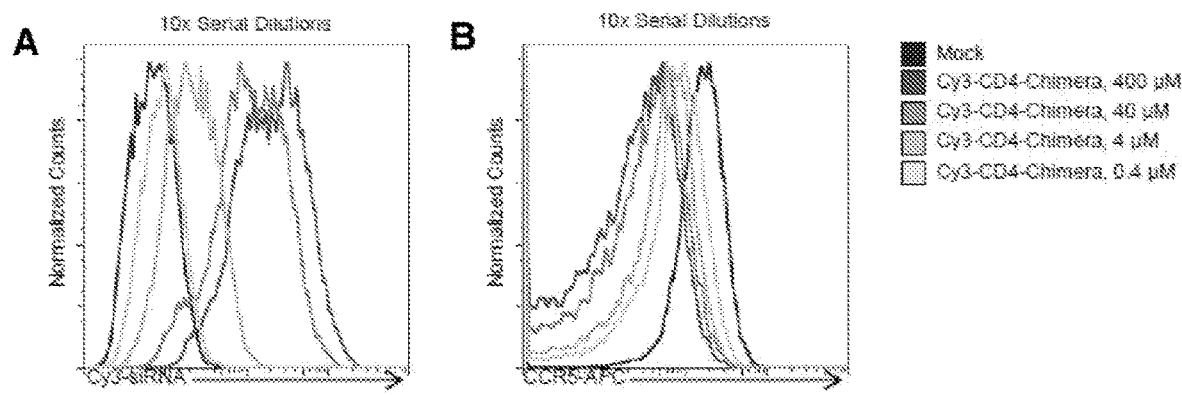
FIGS. 7A-7C show that uptake of Cy3-labeled CD4-aptamer siRNA chimeras (CD4-AsiC) and knockdown of its target gene product CCR5 is dose-dependent in MAGI cells. MAGI cells (HeLa cells that stably express CD4 and CCR5) were treated with 10-fold dilutions of CD4-AsiC bearing Cy3-labeled CCR5 siRNA. Uptake of Cy3-siRNA (FIG. 7A) and knockdown of CCR5 (FIG. 7B) analyzed 3 d later were both dose-dependent.
Figure 7C:
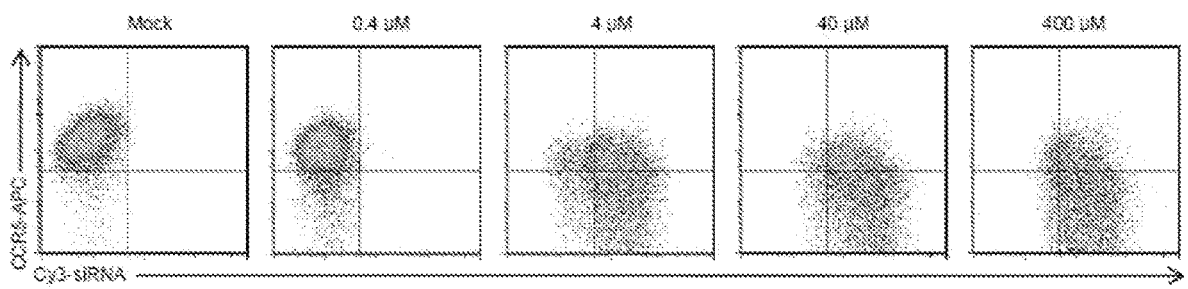
Figure 8A:
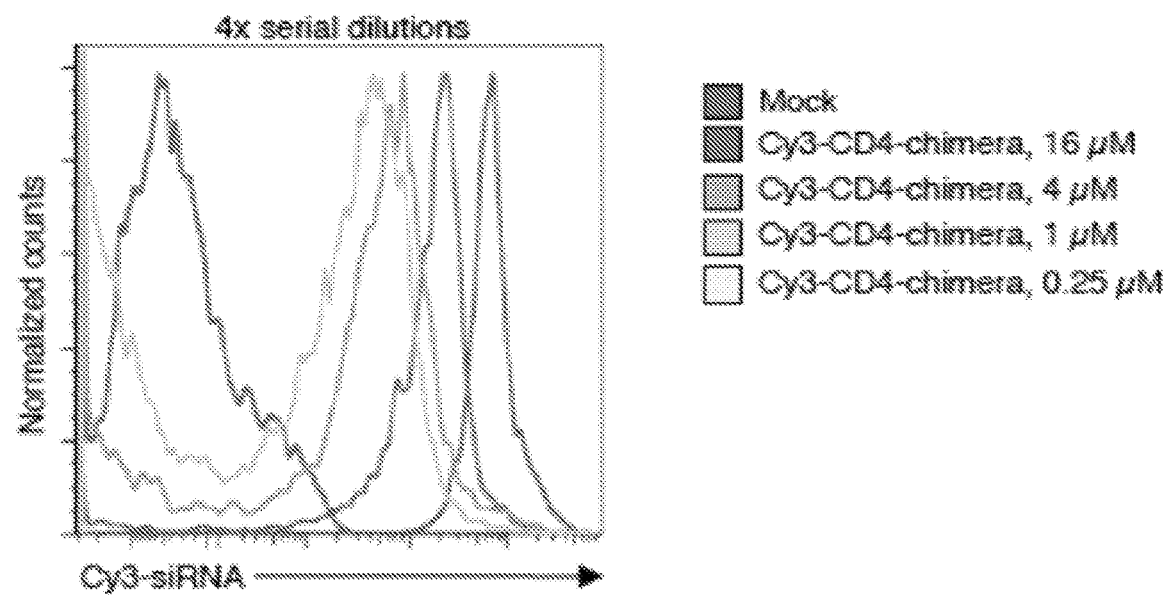
FIGS. 8A-8D show the dose-dependent uptake of Cy3-labeled CD4 Aptamer siRNA chimeras (CD4-AsiC) and knockdown of CCR5 in primary monocyte-derived macrophages (MDMs). MDMs purified from freshly isolated PBMCs, were treated with 4-fold dilutions of CD4-AsiC bearing Cy3-labeled CCR5 siRNA and analyzed by flow cytometry 72 h later. Representative data are shown in FIGS. 8A and 8B and the aggregate mean fluorescence intensity (MFI) (mean±SEM) from duplicate samples from 2 healthy donors in two independent experiments are plotted in FIGS. 8C and 8D. Cy3-siRNA uptake increased (FIG. 8C) and CCR5 levels decreased (FIG. 8D) with increasing concentrations of CD4-AsiCs. (*p<0.05, **p<0.01, two-tailed t test).
Figure 8B:
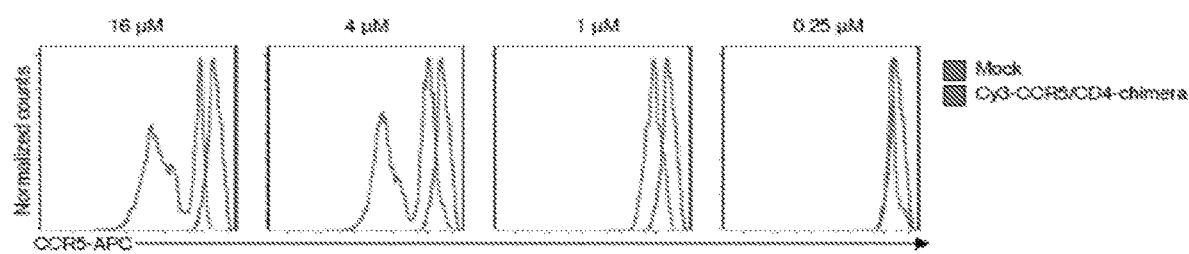
Figure 8C:
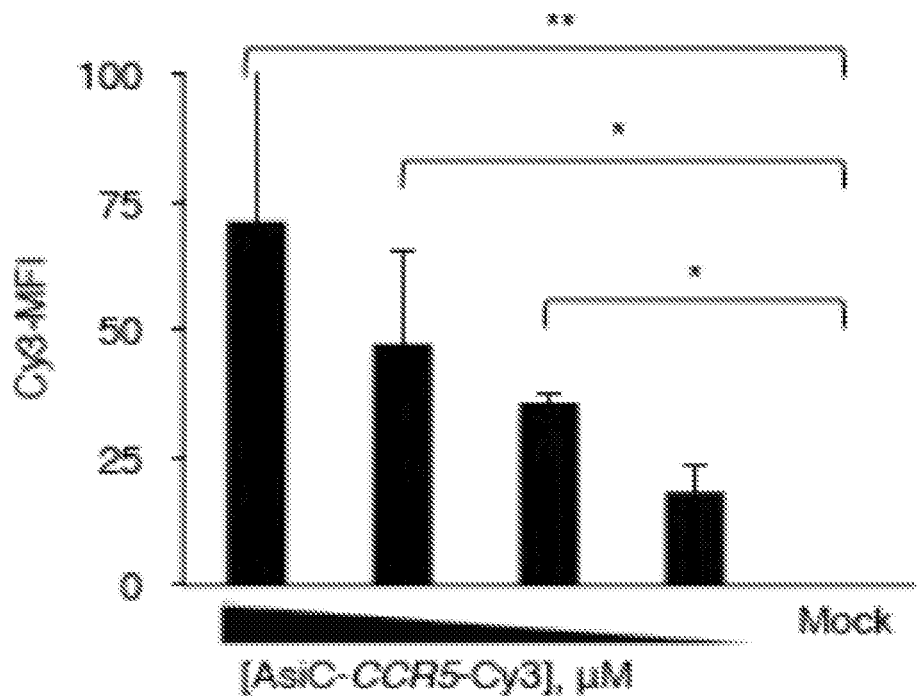
Figure 8D:
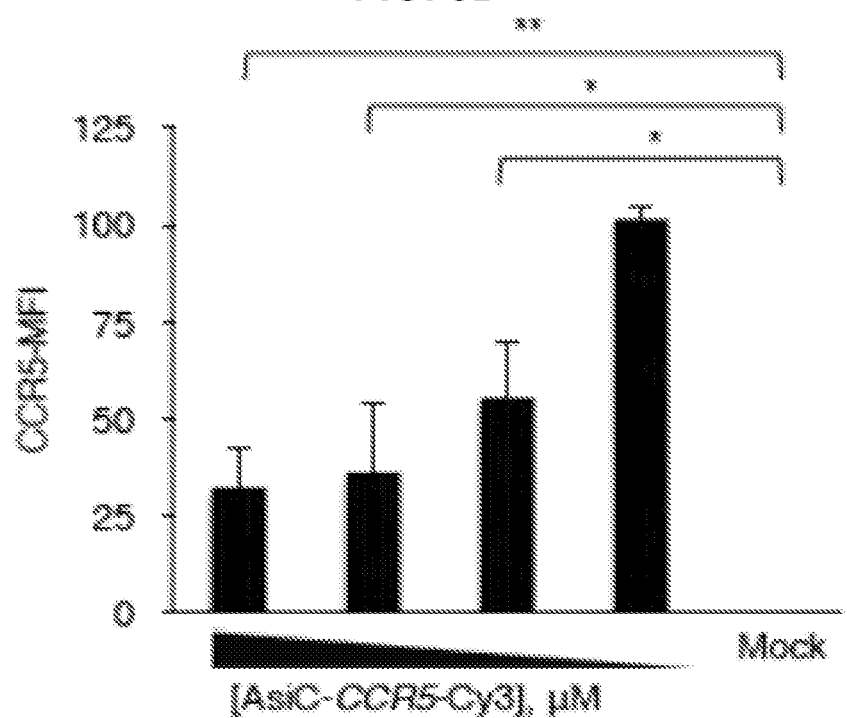
Figure 9A:
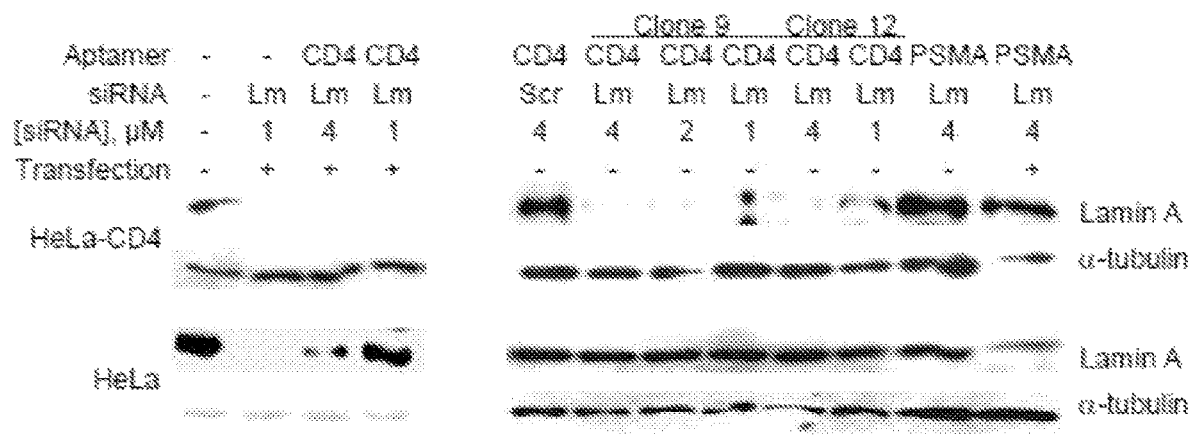
FIGS. 9A-9D show that CD4 aptamer-siRNA chimeras (CD4-AsiC) knocks down lamin A expression specifically in HeLa-CD4 cells and primary human CD4+ cells in vitro. Immunoblot of lamin A protein expression following treatment with CD4-AsiC or PSMA-AsiC bearing siRNAs to lamin A (Lm) or a scrambled (Scr) siRNA control in (FIG. 9A) HeLa cells stably expressing CD4 (HeLa-CD4 (top panels)), compared to parental HeLa cells that do not express CD4 (bottom panels); and in primary MDM and CD4 T cells (FIG. 9B). As positive controls, HeLa-CD4 cells and MDMs were transfected with Oligofectamine and T cells were transfected by electroporation. Without transfection, lamin A knockdown was restricted to cells treated with CD4-AsiC bearing the lamin A siRNA. In separate experiments, specific knockdown of lamin A mRNA relative to GAPDH by CD4-AsiCs was also assessed by qRT-PCR in MDM (FIG. 9C, n=3) and CD4 T cells (FIG. 9D, n=3). Shown are mean±SEM (*p<0.05, "p<0.005, two-tailed t test).
Figure 9B:
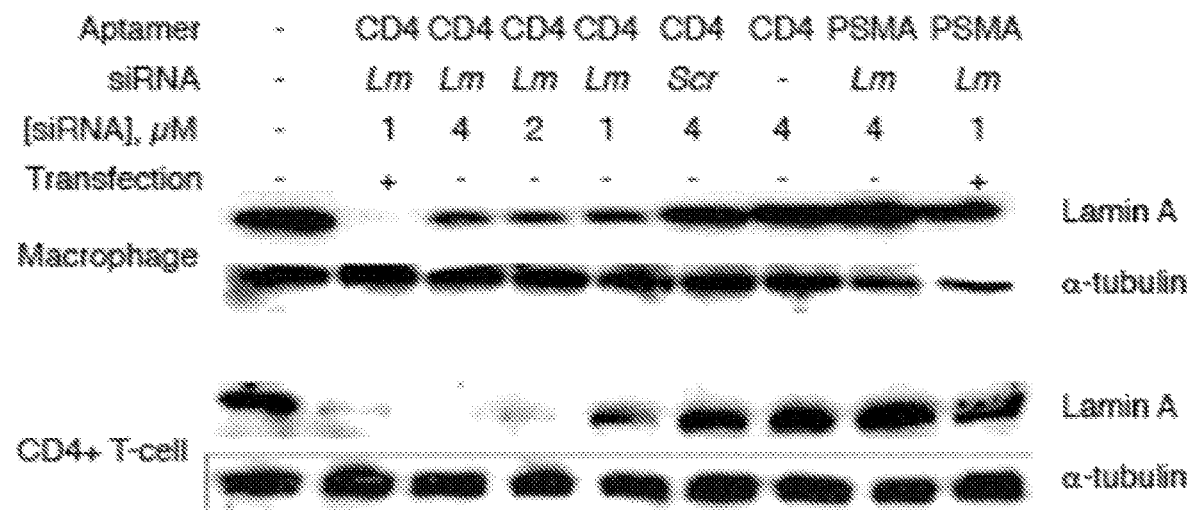
Figure 9C:
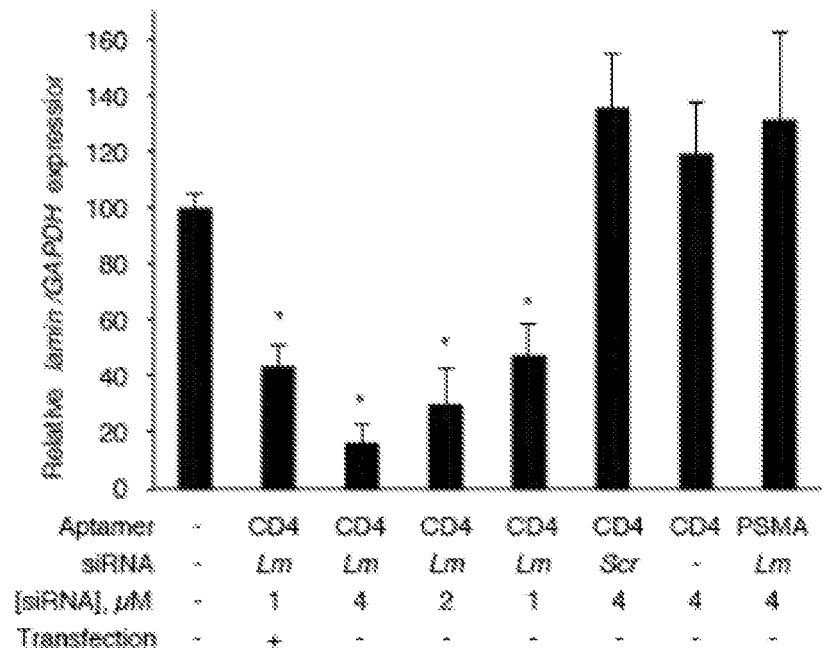
Figure 9D:
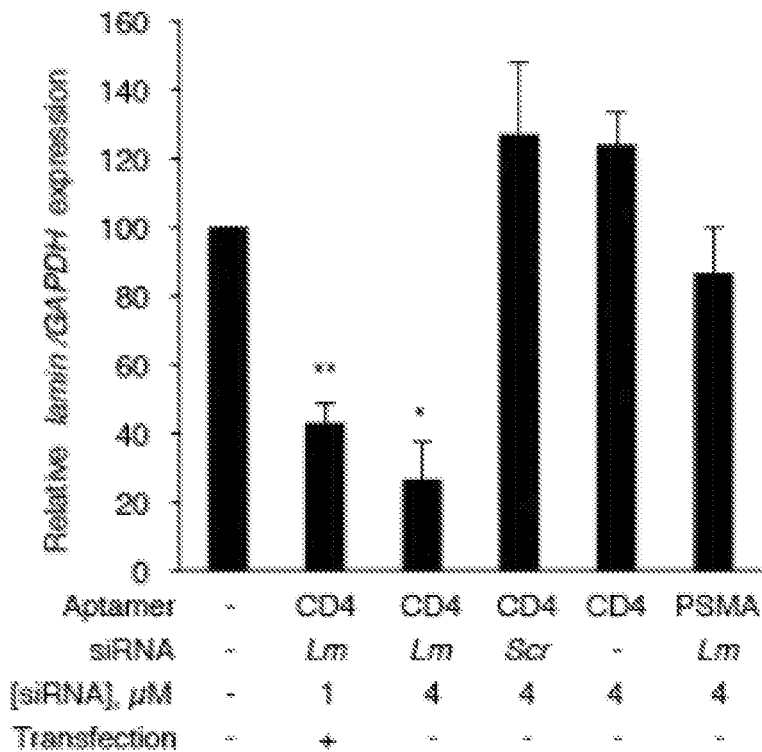
Figure 10:
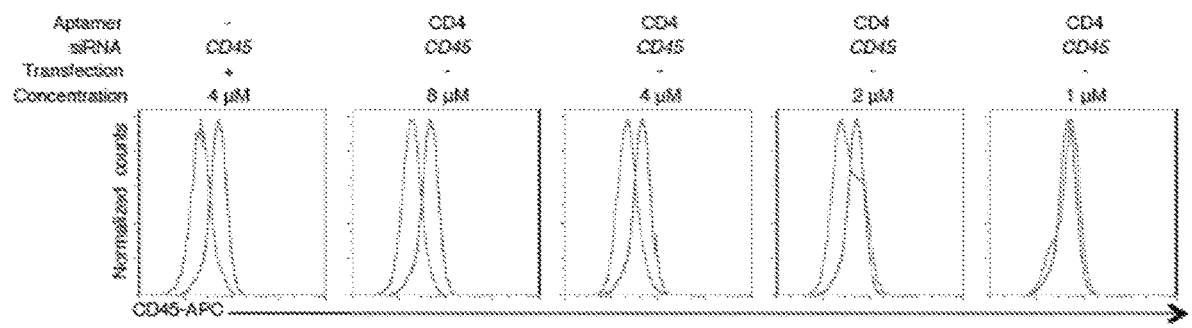
FIG. 10 shows the CD4 Aptamer-siRNA chimera (AsiC)-mediated knockdown of CD45 expression. Treatment with a CD4-AsiC targeting CD45 knocked down CD45 expression in CD4+ Jurkat cells. CD45 surface expression is reduced in a dose-dependent manner 72 h after Jurkat T-cells are treated with increasing amounts of CD4-AsiCs targeting CD45. Transfection was by nucleofection in the positive control (left); the mock-treated sample histogram is shown in blue in all panels.

Dose-dependent uptake of Cy3-labeled CD4-AsiCs and CCR5 knockdown occurred in both HeLa cells expressing CD4 and CCR5 (FIG. 7) and primary MDMs (FIG. 8). Uptake and gene silencing in MDM after 72 h were confirmed by fluorescence microscopy, where Cy3-uptake coincided with FITC-CCR5 knockdown, and neither uptake nor gene silencing occurred in MDMs incubated with Cy3-labeled siRNAs on their own (data not shown). CD4-AsiCs were readily designed to silence other genes, including the nuclear envelope gene lamin A (FIG. 9), the pan-leukocyte marker CD45 (FIG. 10) and the mitotic spindle gene EG5 (data not shown). Dose-dependent silencing was restricted to CD4+ cells, as assessed by immunoblot to measure protein and quantitatve RT-PCR (qRT-PCR) for mRNA. Based on these results, CD4-AsiCs can be used to manipulate expression of virtually any gene in human CD4+ immune cells.

Figure 19A:
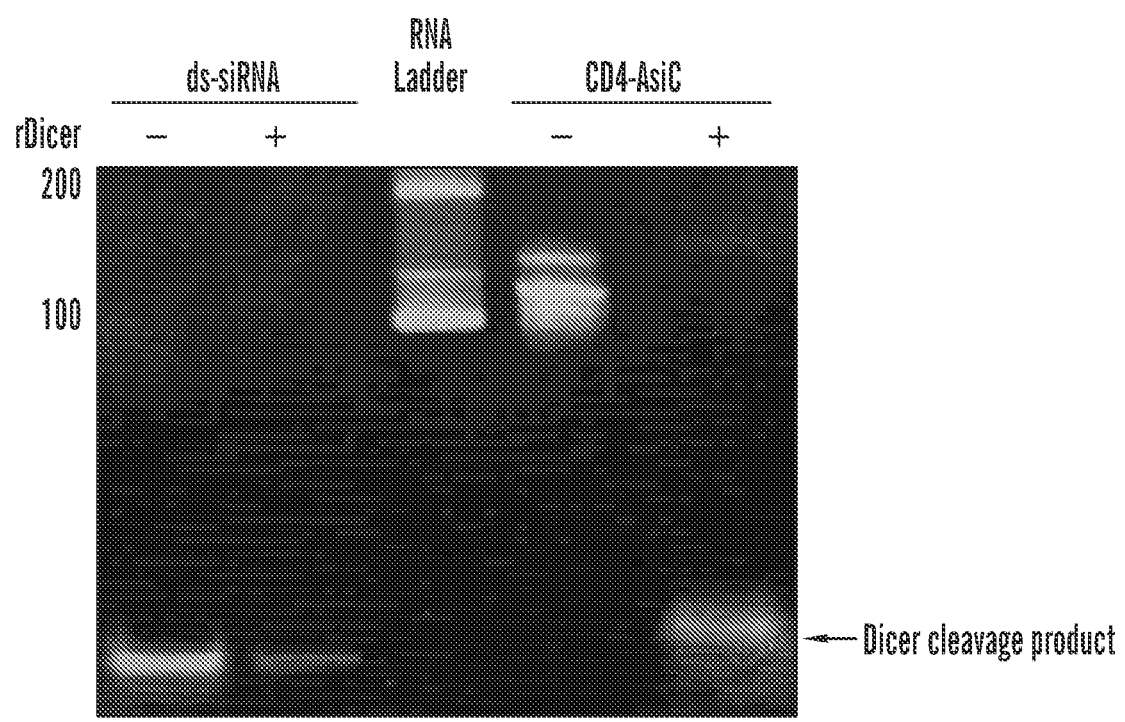
FIGS. 19A-19C show CD4-AsiCs are Dicer substrates and are processed into functional siRNAs intracellularly in a Dicer-dependent fashion.
Figure 19B:
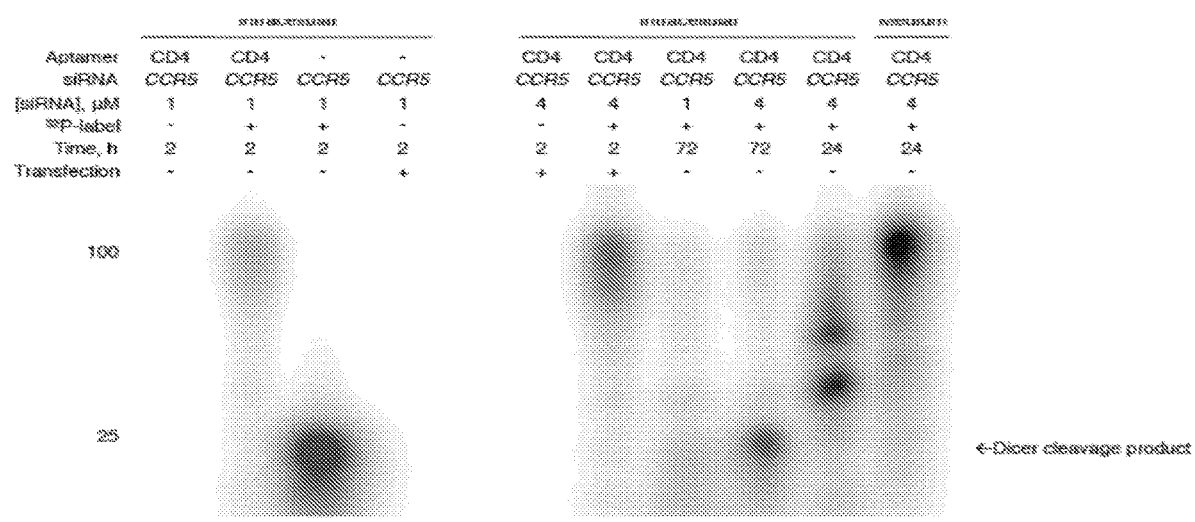
Figure 19C:
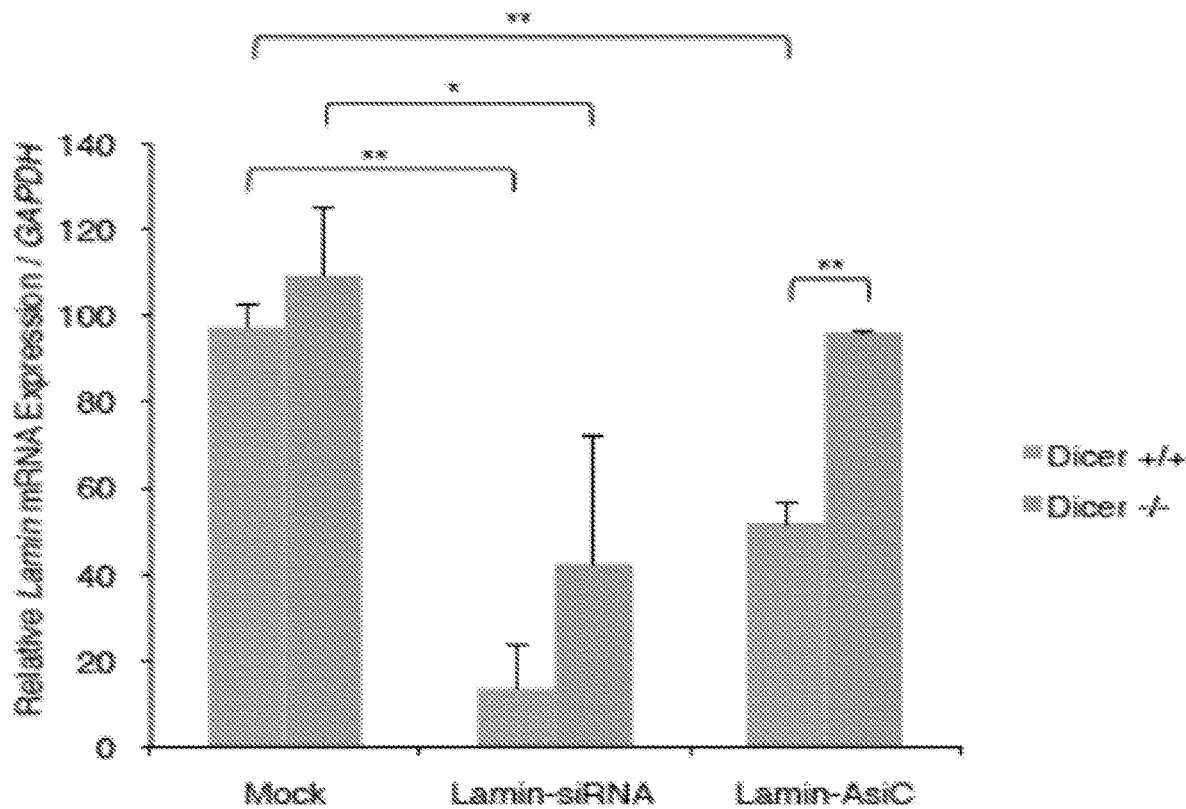
Figure 20A:
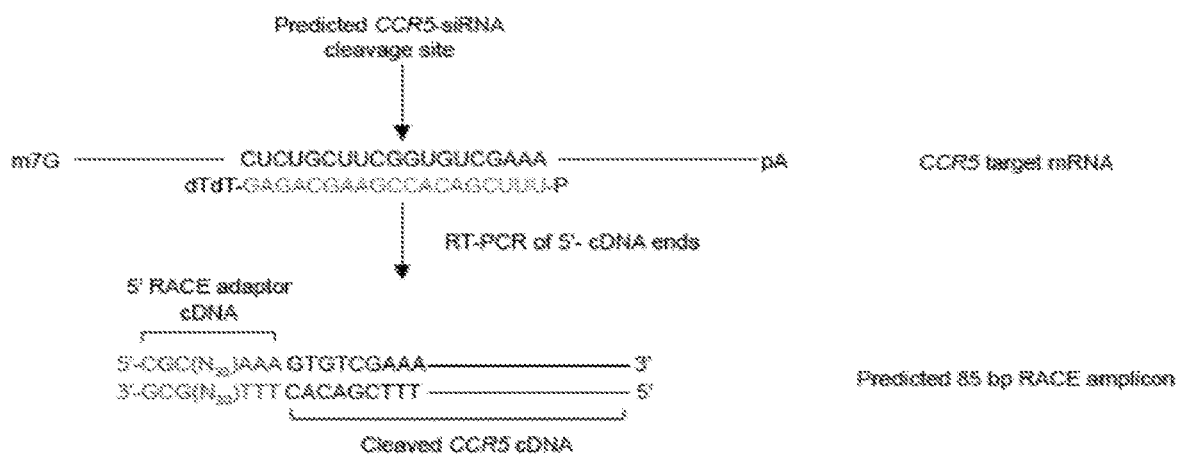
FIGS. 20A-20C show CD4-AsiCs knockdown of gene expression occurs by cleavage of target mRNA.
Figure 20B:
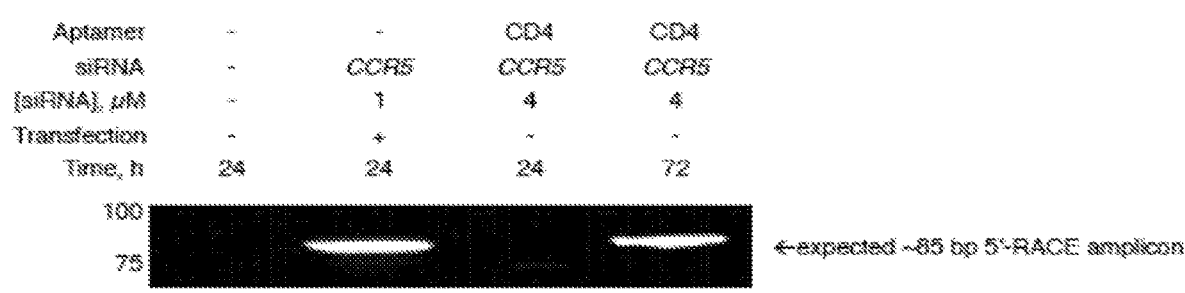
Figure 20C:
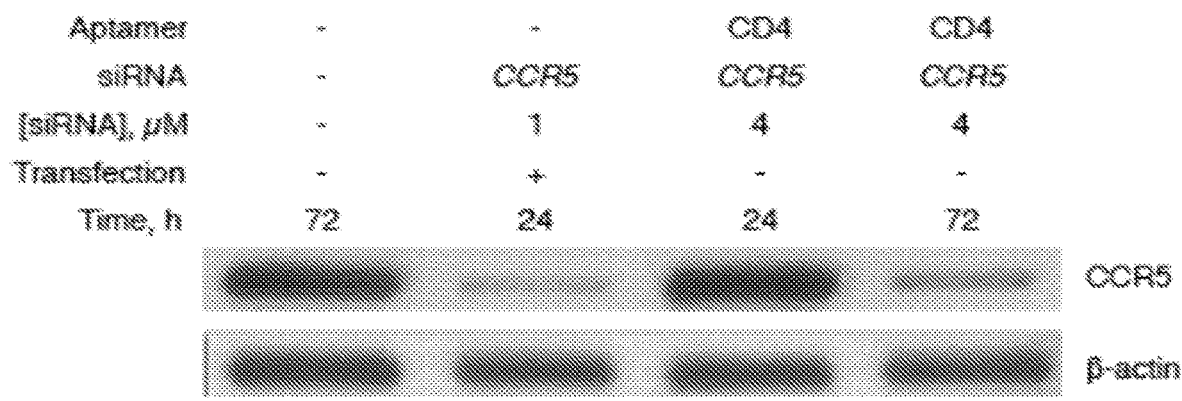

CD4-AsiCs are Dicer substrates and are processed intracellularly into functional siRNAs that use the RNAi pathway to direct mRNA cleavage. To understand the mechanism of CD4-AsiC-mediated silencing, the inventors tested whether these chimeras are substrates for the endoribonuclease Dicer, which processes longer endogenous RNA precursors to short 20- to 25-nt RNAs as part of the RNAi pathway in the cell. When CD4-AsiCs bearing CCR5 siRNAs were incubated with recombinant Dicer, they were virtually completely digested to an expected approximately 21- to 23-nt cleavage product that migrated like a CCR5 siRNA (FIG. 19A). Treatment of primary CD4+ T cells with $^{32}$P-end-labeled CD4-AsiCs also resulted in their processing to an approximately 21- to 23-nt duplex RNA (FIG. 19B), which indicates that similar Dicer cleavage also occurs within cells. Gene silencing by CD4-AsiCs also depended on intracellular Dicer expression in HCT-116 cells, since knockdown of lamin A by CD4-AsiCs only occurred in WT cells, but not in Dicer$^{-/-}$ cells (FIG. 19C and Cummins J, et al. Proc Nall Acad Sci USA. 2006, 103(10):3687-3692). To confirm that AsiC-mediated silencing was caused by siRNA-directed cleavage of target gene mRNA, modified 5'-rapid amplification of cDNA ends (5'-RACE; Soutschek J, et al. Nature. 2004, 432(7014):173-178) was used to analyze RNA isolated from primary MDMs treated with CCR5 CD4-AsiCs for CCR5 mRNA cleavage fragments (FIG. 20). An amplified CCR5 RNA fragment of the expected size was detected 72 hours after adding the CCR5 CD4-AsiCs. Sequencing of the amplified fragments confirmed that cleavage occurred 10 nt from the 5' end where the CCR5 antisense strand bound, at the expected site (Elbashir S M, Lendeckel W, Tuschl T. Genes Dev. 2001; 15(2):188-200). Thus, the data shows that CD4-AsiCs are processed by Dicer to release functional siRNA duplexes that direct target mRNA cleavage via the RNAi pathway.

CD4-AsiCs Inhibit HIV Replication in Primary CD4+ Cells In Vitro.

Figures 3A, 3B:
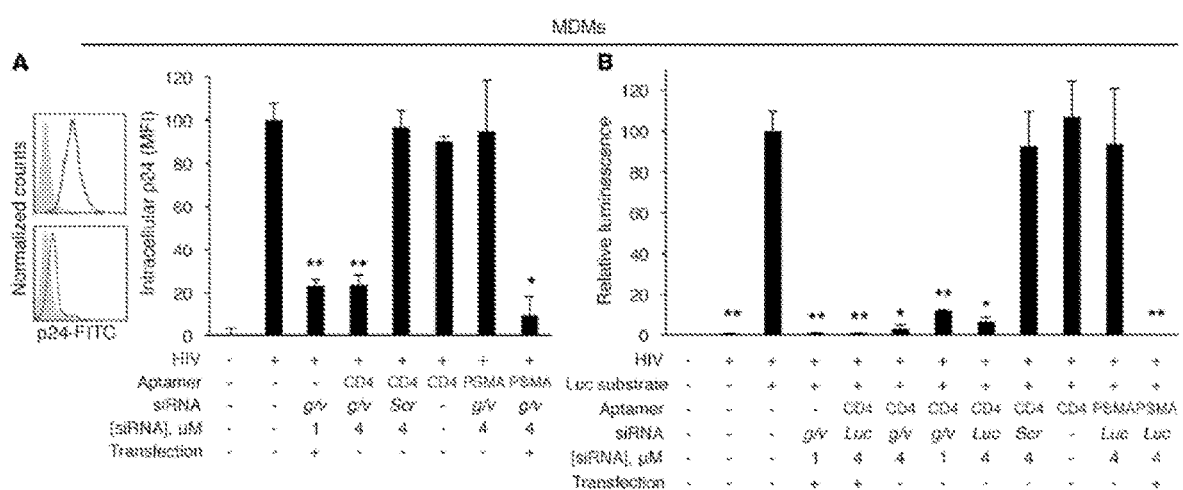
FIGS. 3A-3D demonstrate that CD4 aptamer-siRNA chimera (CD4-AsiC) inhibits HIV replication in primary cells in vitro. MDMs (FIGS. 3A, 3C), and CD4+ T-cells (FIGS. 3D, 3E), were infected with HIV-1$_{BaL}$ and HIV-limab, respectively, for 48 h and then treated with the indicated final total concentration of mixtures of CD4-AsiC or PSMA-AsiC containing siRNAs targeting HIV gag and vif (g/v). Controls contained a PSMAn aptamer or scrambled (Scr) siRNA.
Figures 3C, 3D:
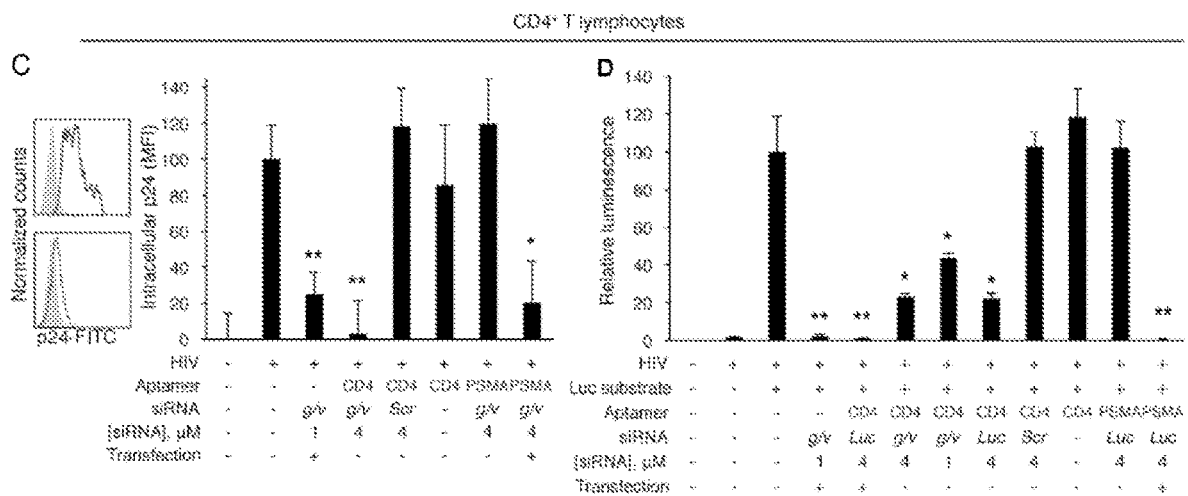
Figure 11A:
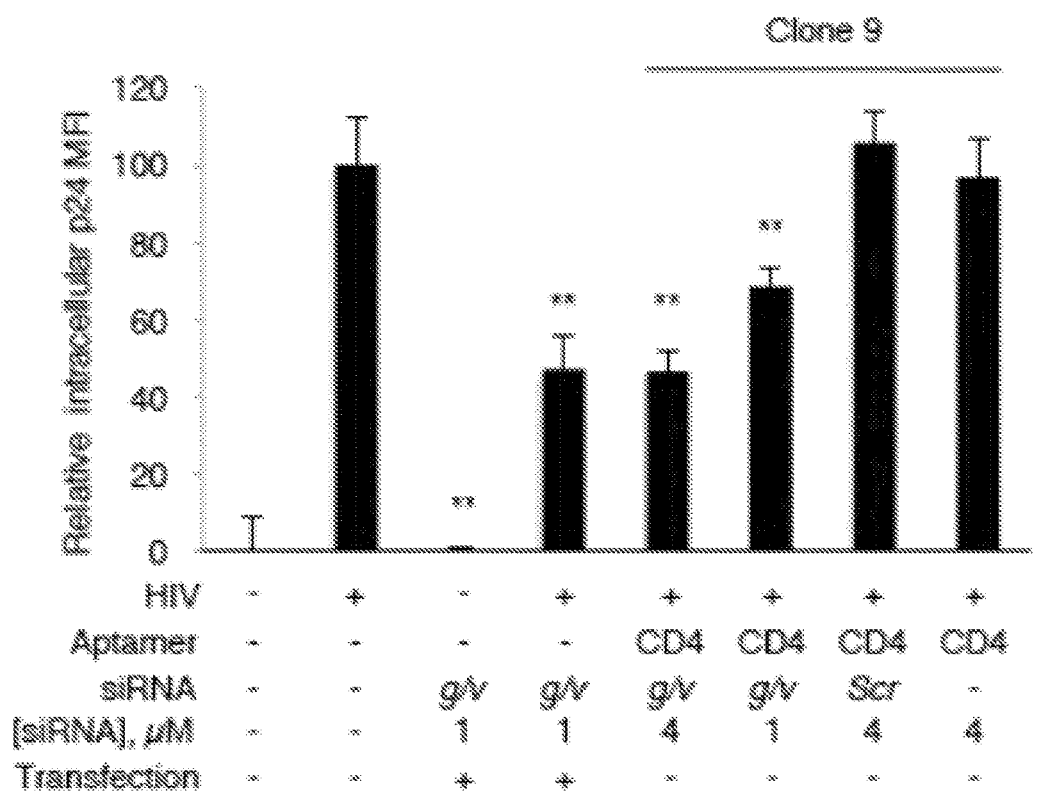
FIGS. 11A-11C show the suppression of HIV replication in HeLa-CD4 and Jurkat cells by CD4 aptamer-siRNA chimeras (CD4-AsiC). Cells were infected for 48 h with HIV-1$_{mb}$ and then treated with a 4 μM mixture of CD4-AsiCs designed to knockdown HIV gag and vif (g/v) or a control scrambled (Scr) sequence. CD4-AsiCs were generated using either the clone 9 aptamer (FIG. 11A) or the clone 12 aptamer (FIG. 12B). Aptamer sequences are shown in FIGS. 5B and 5C. 48 h later cells were stained for intracellular HIV-1 p24 and analyzed by flow cytometry.
Figure 11B:
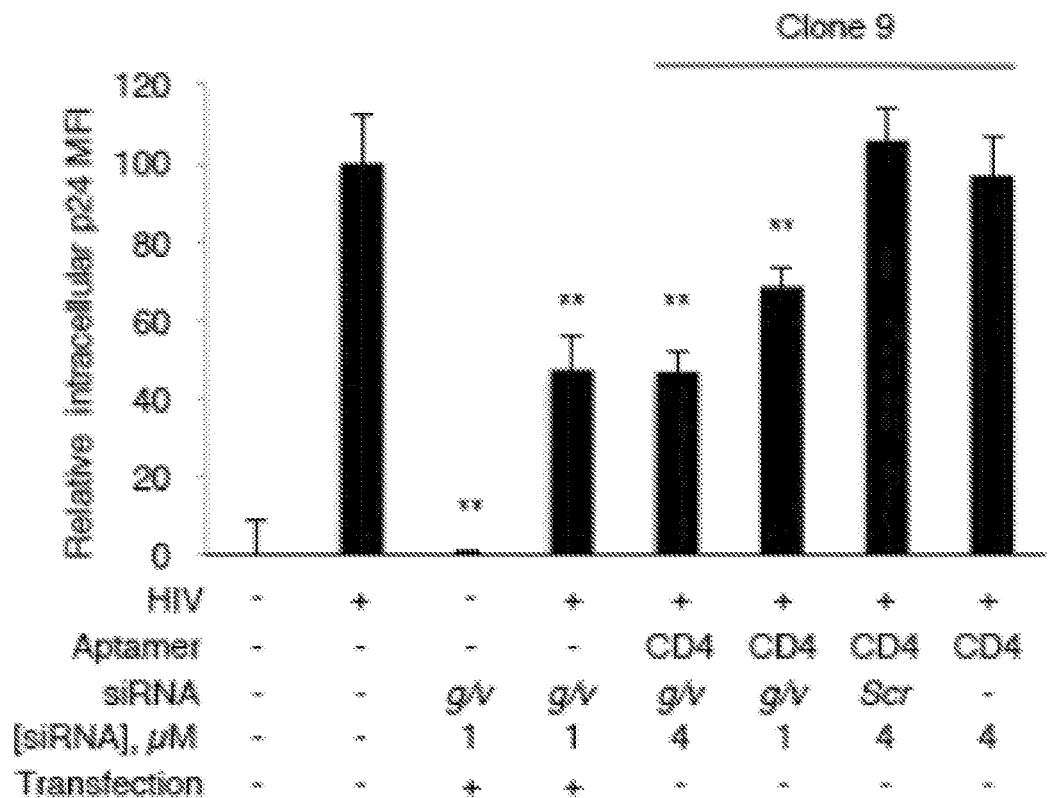
Figure 11C:
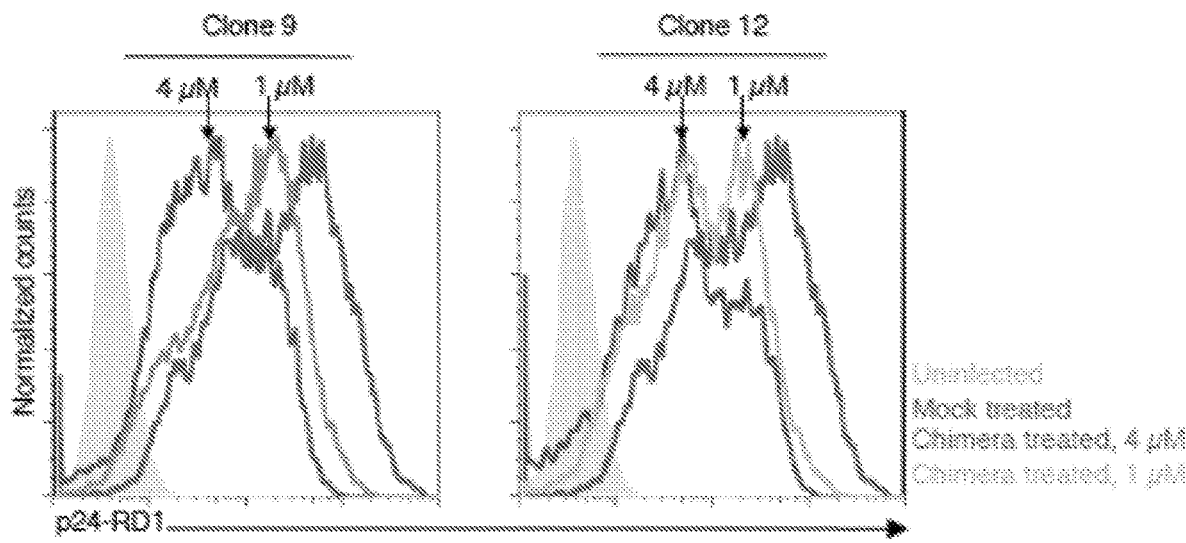
Figure 21A:
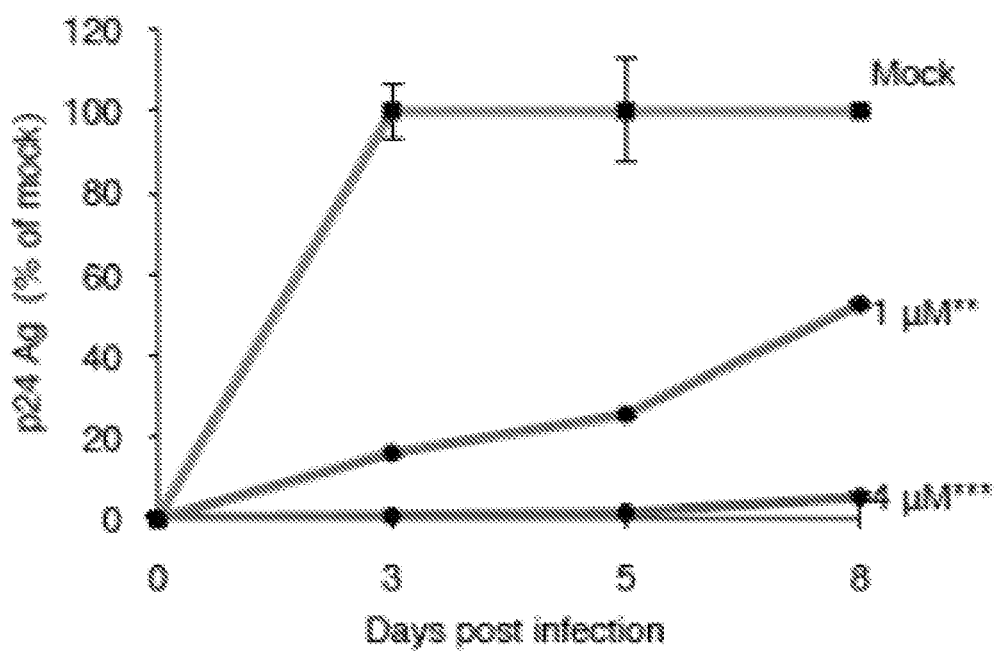
FIGS. 21A-21C show CD4-AsiCs against CCR5 inhibit HIV replication in primary MDMs in vitro.
Figure 21B:
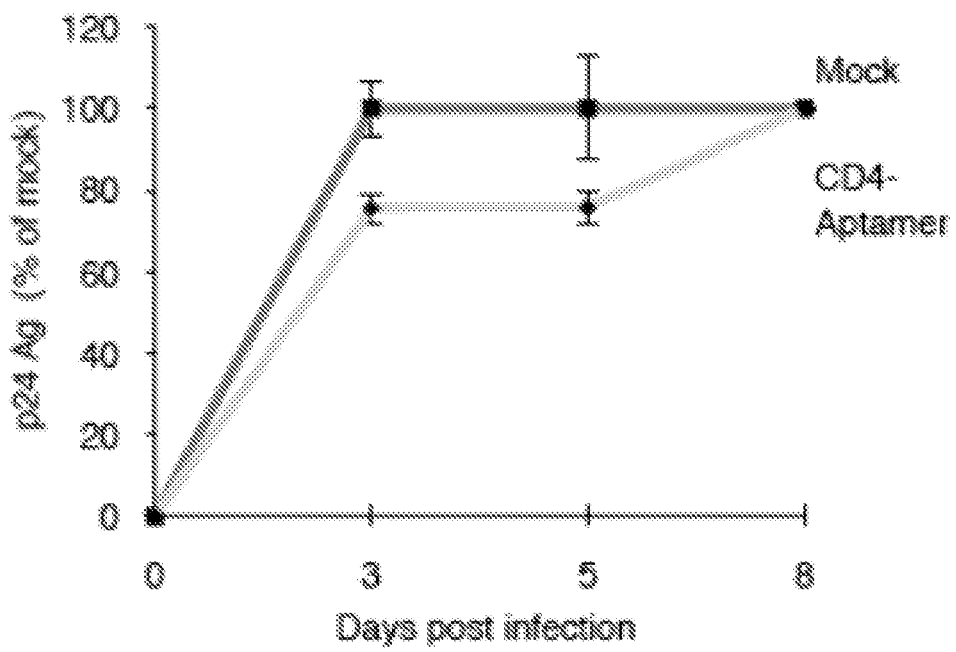
Figure 21C:
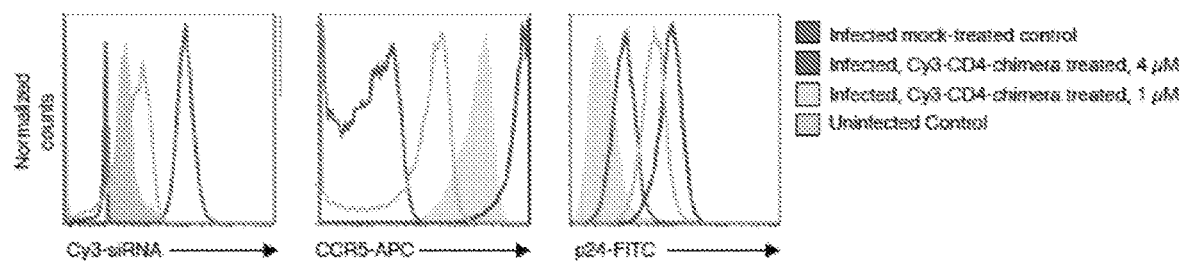
Figure 22A:
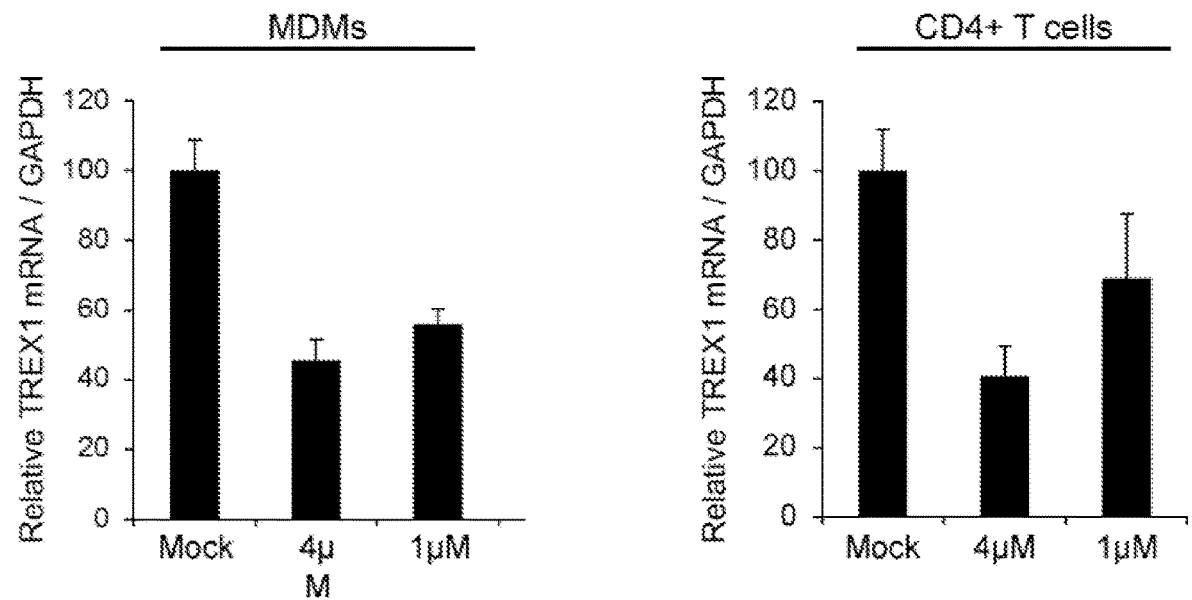
FIGS. 22A-22F show silencing of TREX1 with CD4-Aptamer siRNA chimeras (CD4-AsiCs).
Figure 22B:
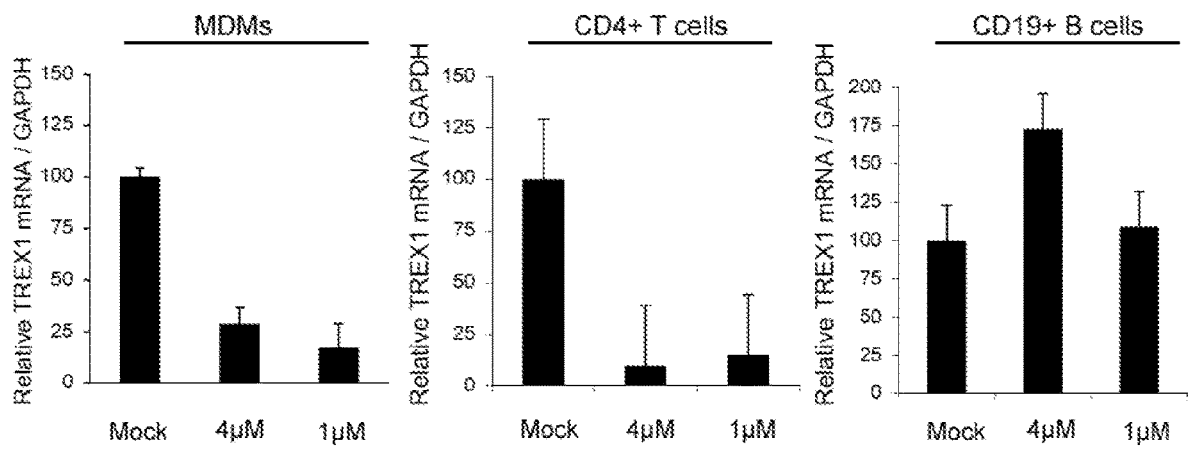
Figure 22C:
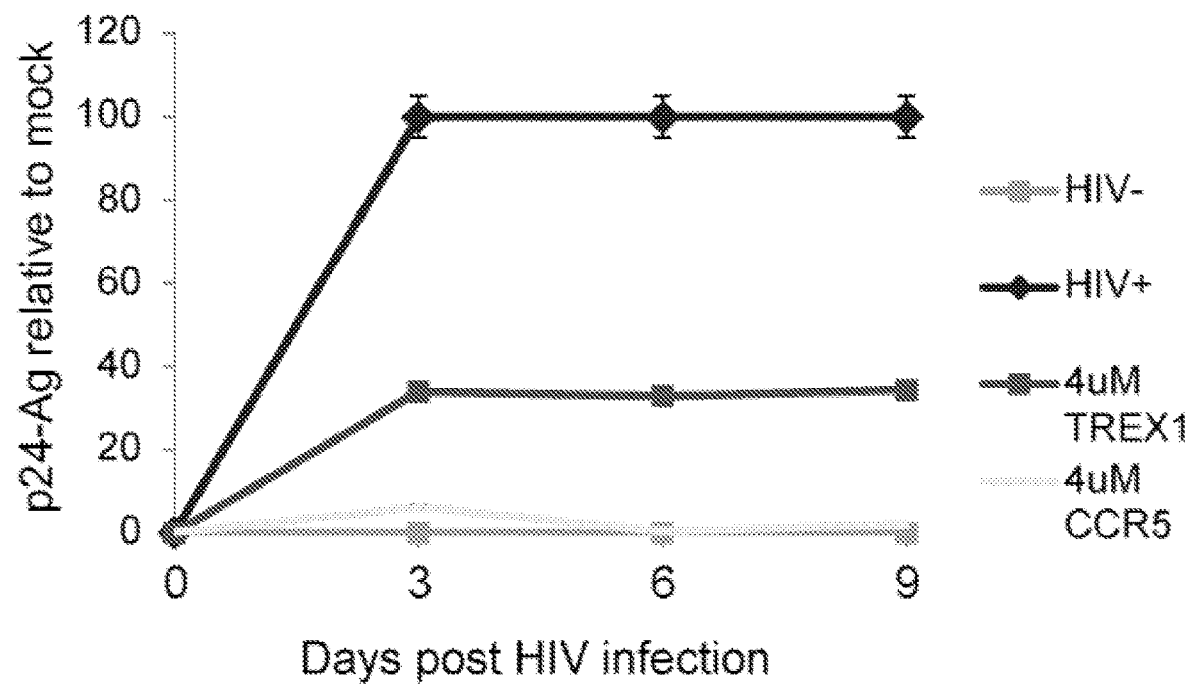
Figure 22D:
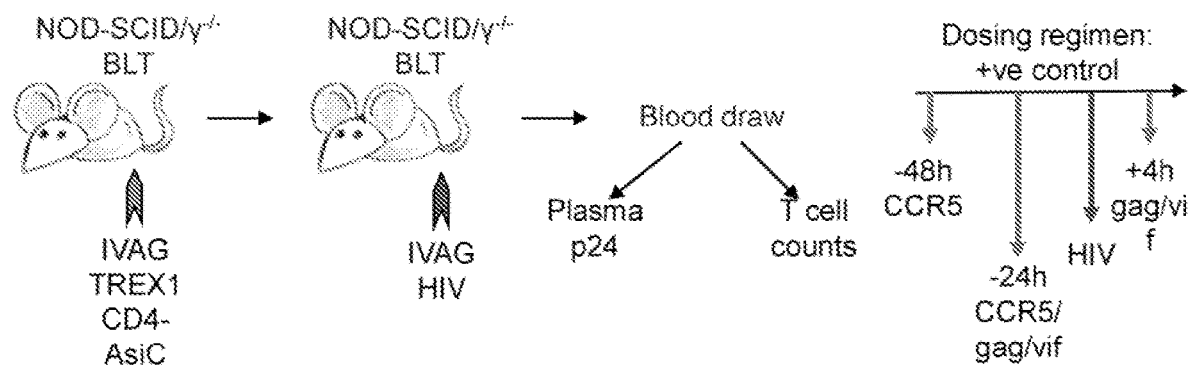
Figure 22E:
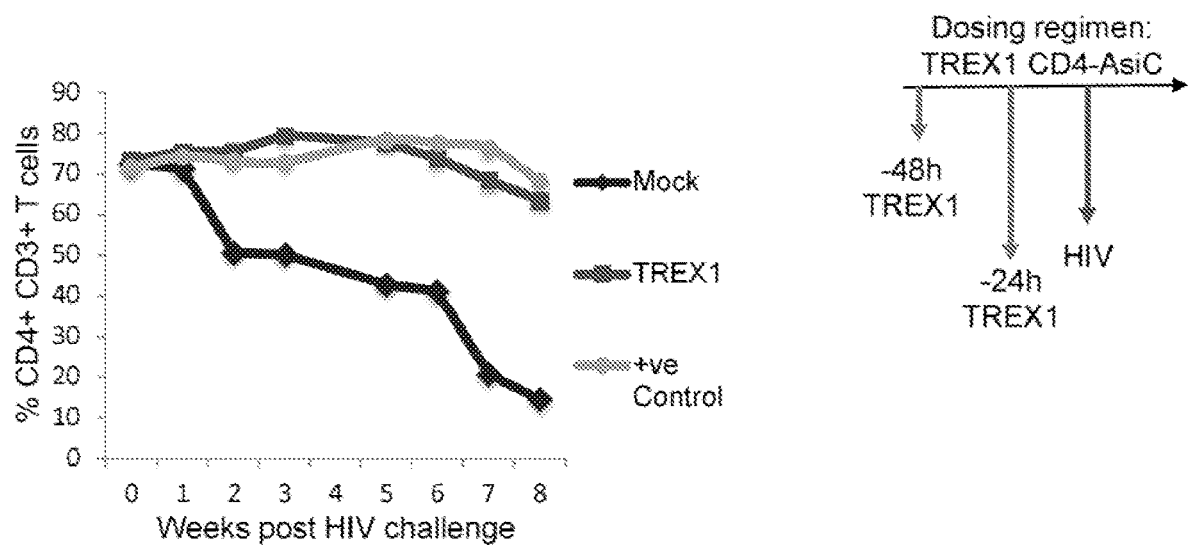
Figure 22F:
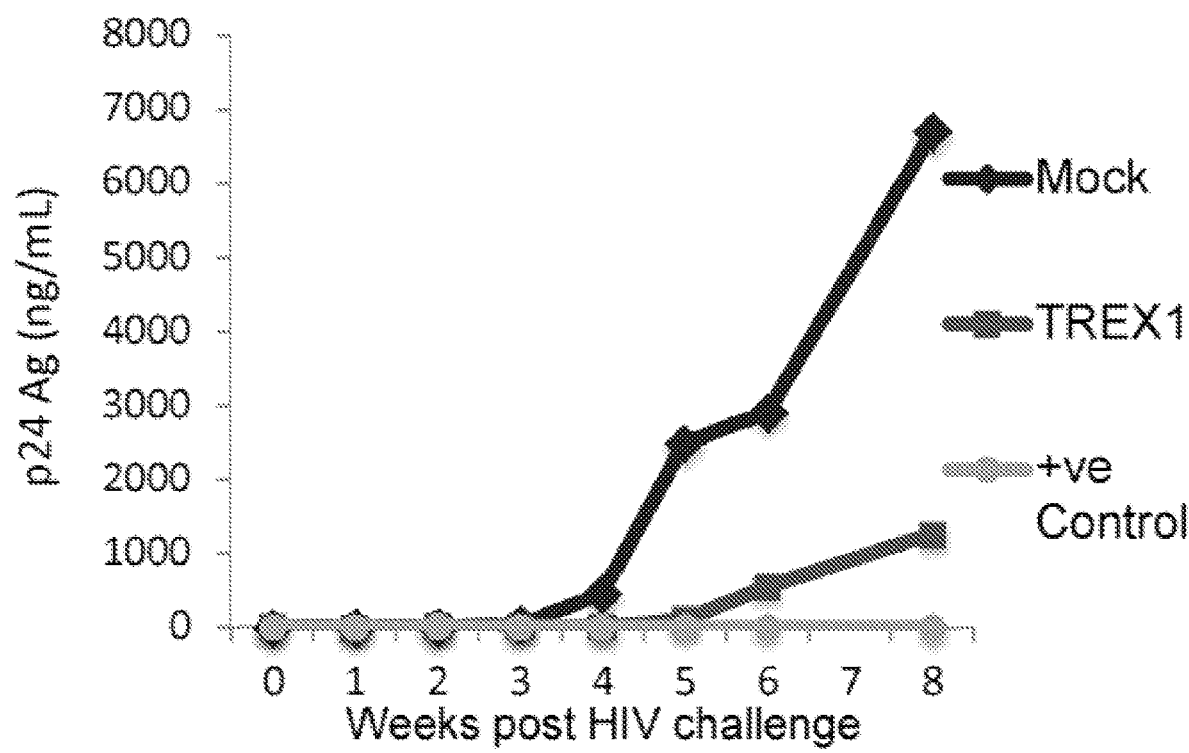
Figure 23A:
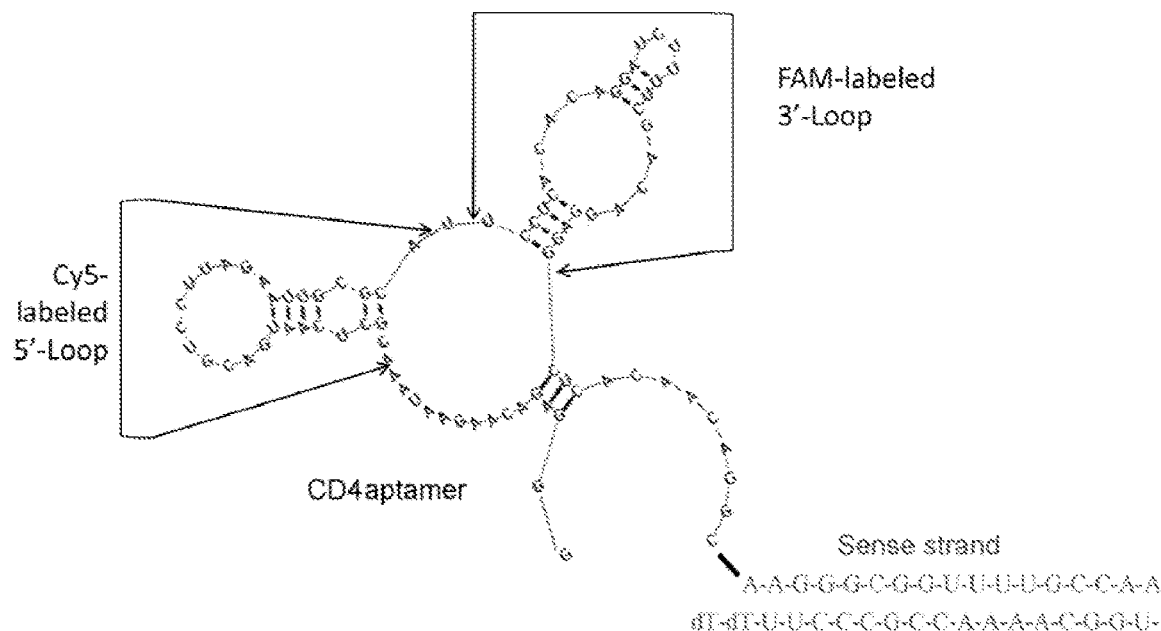
FIGS. 23A and 23B show uptake of truncated CD4 aptamers by cells.
Figure 23B:
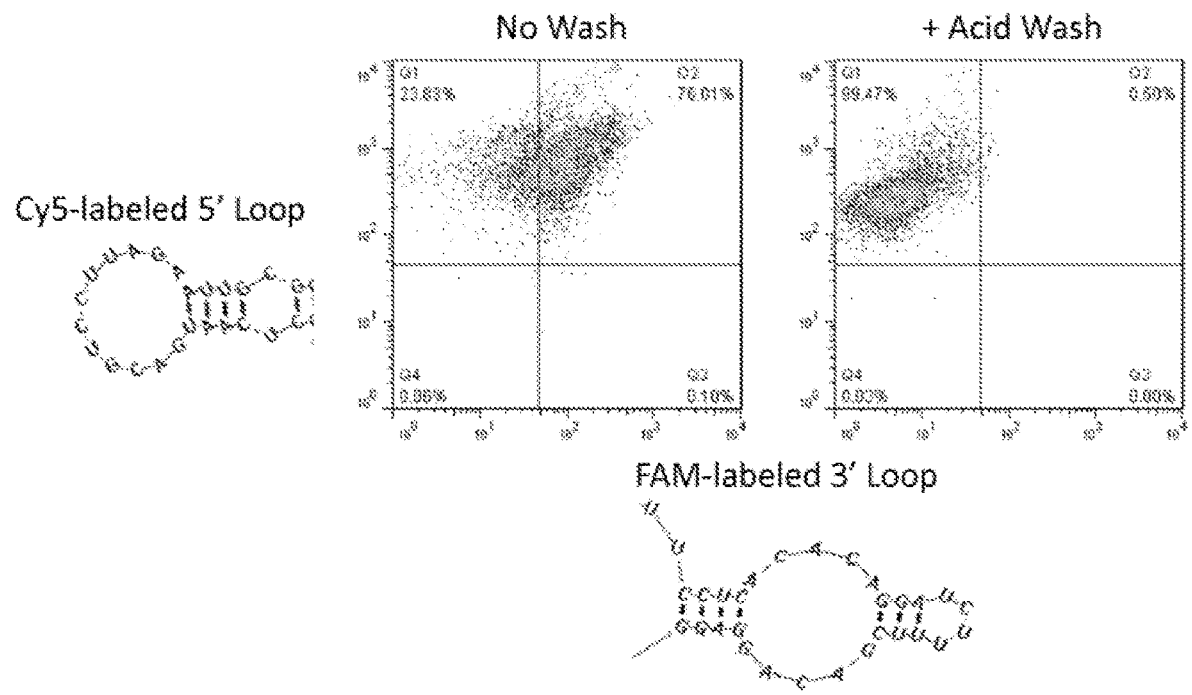
Figure 24A:
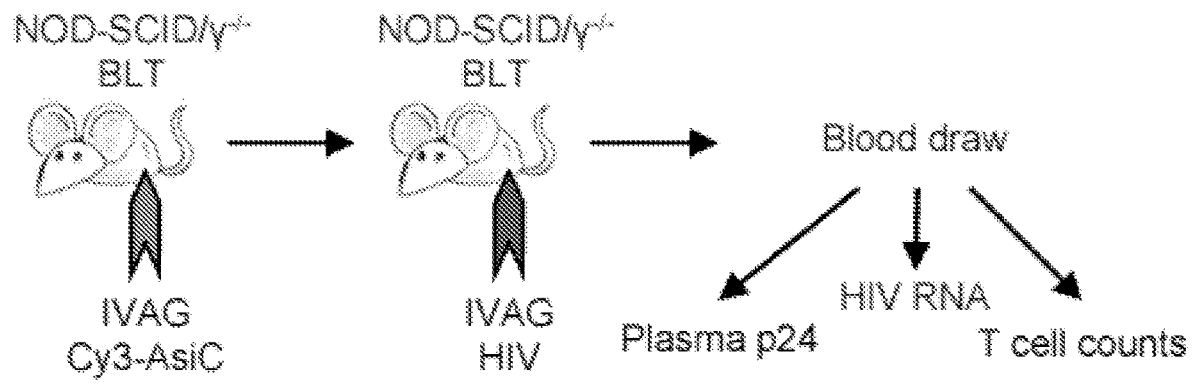
Figure 24B:
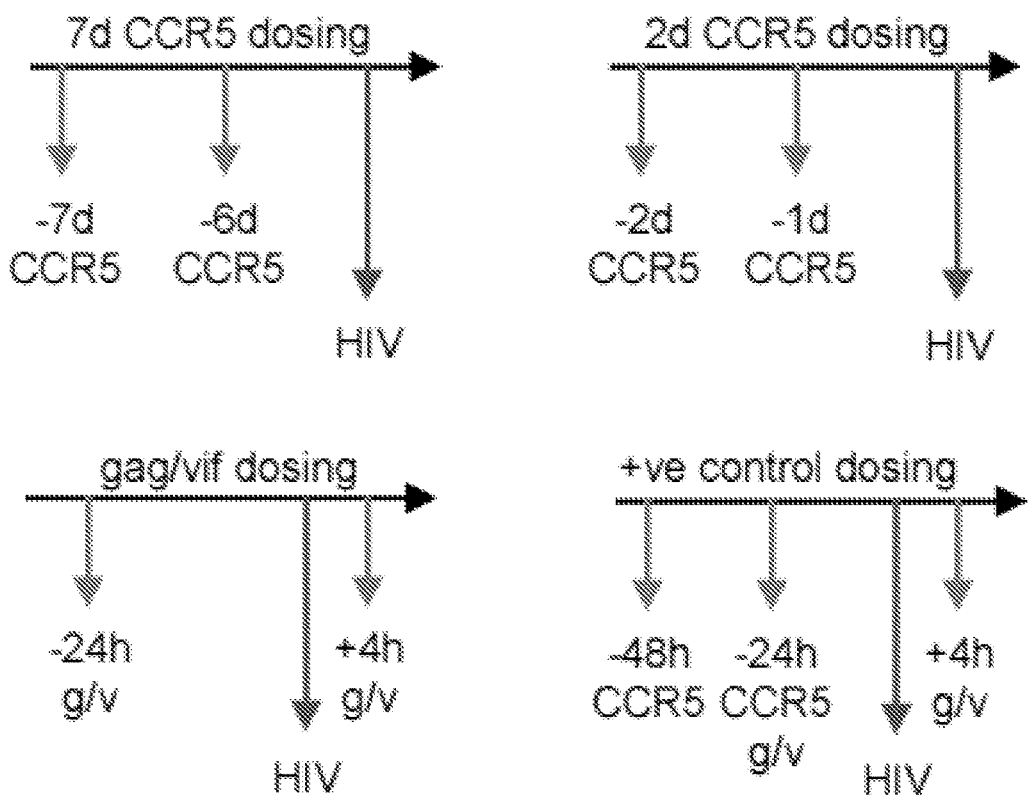
Figure 24C:
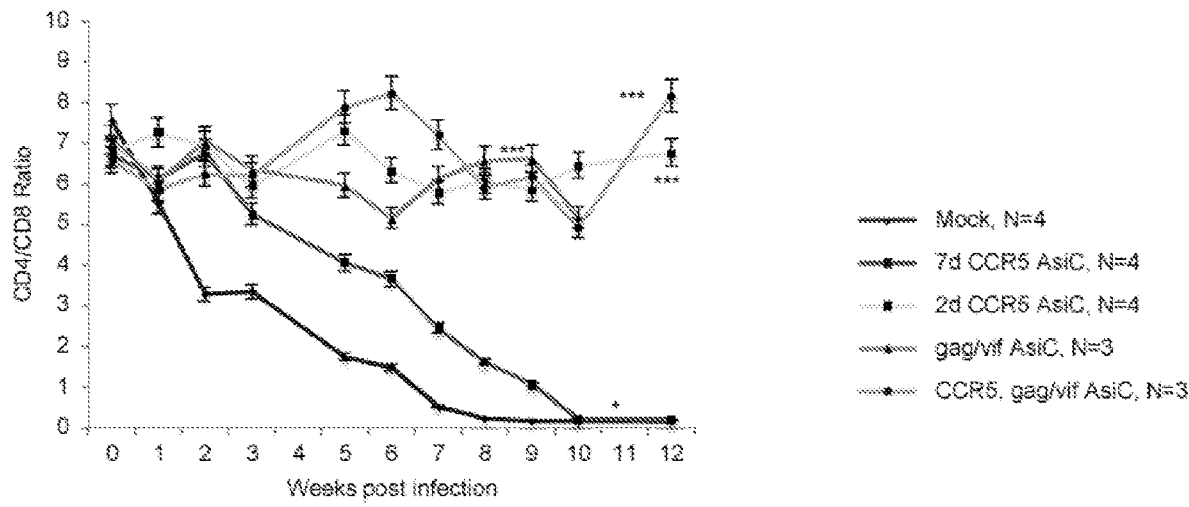
Figure 24D:
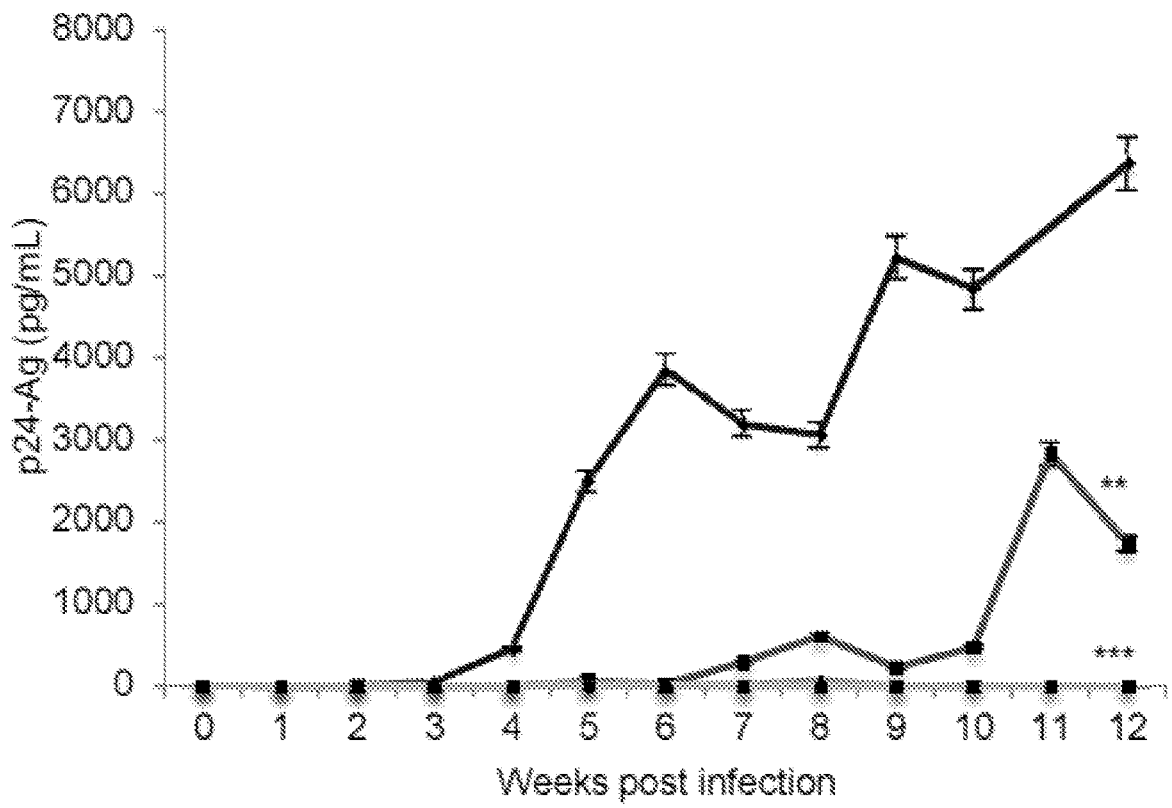
Figure 24E:
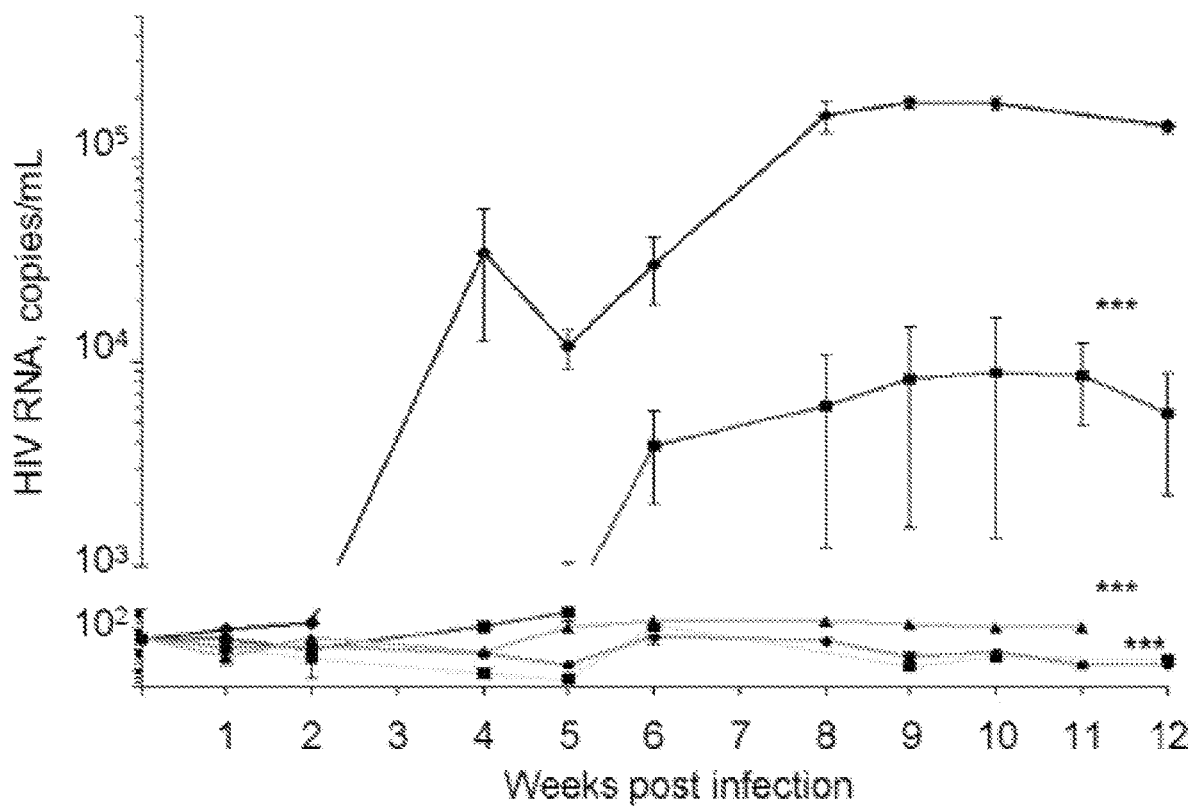

Inhibiting HIV infection provides a stringent test of effective gene knockdown in CD4 cells. It was first tested whether treatment with a mixture of CD4-AsiCs against IIIV gag and vif (FIG. 3) or against CCR5 (FIG. 21) could suppress viral production in an established HV inection. Primary cells were infected with HIV-1 48 hours before CD4-AsiC treatment. Viral production was assessed by flow cytometry analysis of intracellular p24 capsid antigen (p24-Ag) or by p2 Ag ELISA of the culture suprnatant. CD4-AsiCs inhibited viral replication in MDMs (FIG. 3A) and CD4+ T-cells (FIG. 3C). siRNA agains CCR5 also inhibited HIV infection in primary MDMs (FIG. 21), and siRNAs agains viral genes inhibited infection in HeLa-CD4 and Jurka cells in a dose-dependent manner (FIG. 11). There was no antiviral effect using chimeras containing PSMAn aptamer or scrambled siRNA. Viral inhibition and RNA internalization were confirmed by fluorescence in situ hybridization (FISH) for HIV RNA and Cy3 fluorescence, respectively, in MDMs treated with a cocktail of gag, vif and Cy3-labeled CCR5 CD4-AsiCs, but not with a cocktail of PSMA-AsiCs (data not shown).

These CD4 aptamers bind CD4 principally via its V4 domain, but also partially block the receptor's V1 gp120-binding domain (Davis, K. A., et al. *Nucleic Acids Res* 26, 3915-3924 (1998); Arthos, J. et al. *Cell* 57, 469-481 (1989)). Therefore, CD4-AsiCs can inhibit HIV infection by two mechanisms-by blocking HIV entry by inhibiting HIV gp120 from binding to CD4 and/or by knocking down either viral genes or host genes required for viral entry or replication. Pre-infection treatment of cells with CD4-AsiCs hearing scrambled siRNAs or with CD4-aptamers lacking an siRNA tail partially inhibited infection in HeLa-CD4 cells (data not shown), which indicates that blocking HI binding to CD by the aptamer contributes to overall inhibition o HIV infection. To evaluate the gene silencing component of chimera-mediated HIV suppression on its own, cells were pre-treated with AsiCs before challenging with a CD4-independent single round VSV-G-pseudotyped HIV-1 virus encoding a luciferase reporter gene. In both MDMs (FIG. 3B) and CD4+ T-cells (FIG. 3D), CD4-AsiCs bearing gag and vif or luciferase siRNAs significantly decreased luciferase activity compared to all control conditions. Therefore, the CD4-AsiCs encoding either viral or CCR5 siRNAs likely inhibit HIV infection both by blocking entry and gene knockdown.

CD4-AsiCs do not Alter Expression of Lymphocyte Activation Markers.

Figure 12A:
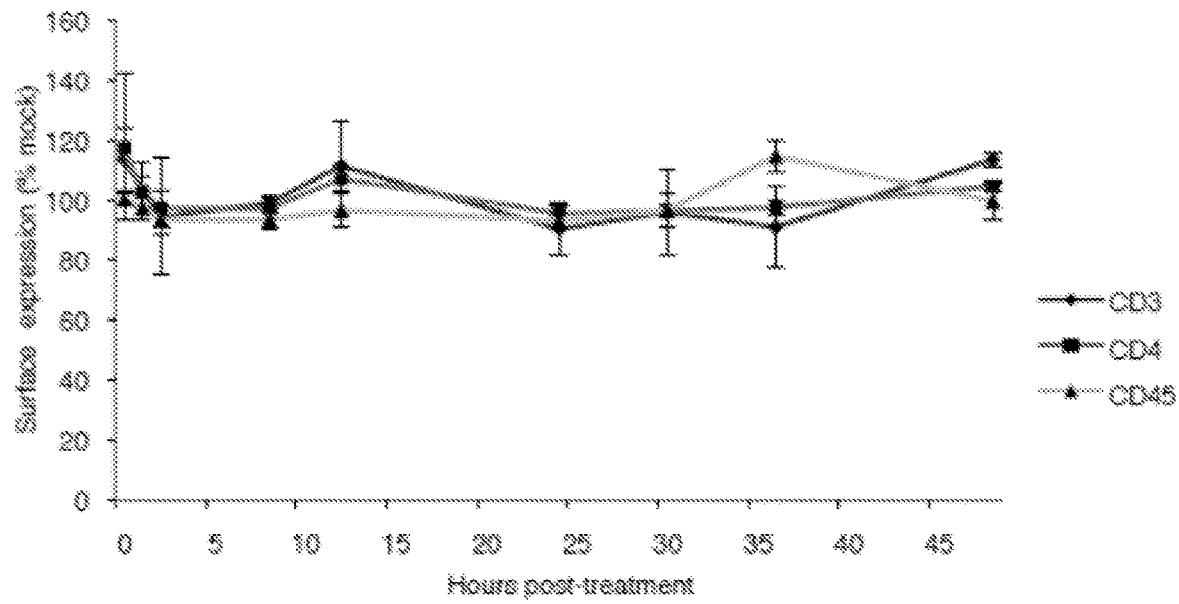
FIGS. 12A and 12B show that treatment with CD4 aptamer-siRNA chimeras (CD4-AsiC) does not down-regulate cell surface CD4 expression or activate T cells. CD4 T cells, immunomagnetically selected from peripheral blood of normal human donors, were treated with CD4-AsiCs and CD4, CD3, and CD45 (FIG. 12A) and CD25 and CD69 (FIG. 12B) levels were monitored by flow cytometry over 2 d.
Figure 12B:
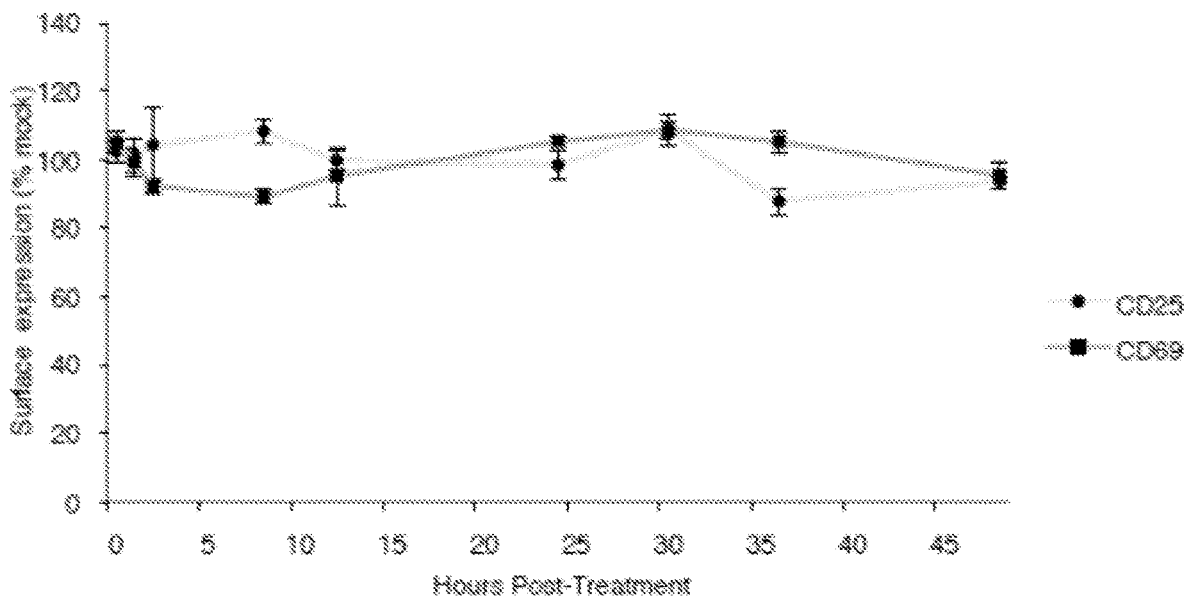

CD4-AsiCs are a useful tool for genetic manipulation of hard-to-transfect CD4+ cells to study the effect of knocking down one gene at a time. For this application, the CD4-AsiCs ideally should not alter CD4 surface expression or cause lymphocyte activation. Activation of CD4+ T cells by CD4-AsiCs would also be undesirable for their use to prevent or treat HIV infection since activated T cells are more susceptible to HIV infection. Since CD4-AsiCs contain only one receptor binding site and most T cell activation involves receptor cross-linking, it would not be expected for CD4-AsiCs to activate the cells it transfects. To evaluate this, uninfected CD4+ T cells treated with CD4-AsiCs directed against exogenous viral genes were assayed by flow cytometry over 2 days for changes in surface protein expression of CD4 and other lymphocyte markers that change with cell activation. Neither CD4 nor other cell surface receptors (CD3, CD45, CD25, CD69) changed significantly compared to mock-treated controls (FIG. 12).

CD4-AsiCs Inhibit HIV Replication in Polarized Cervicovaginal Explants.

Figure 4A:
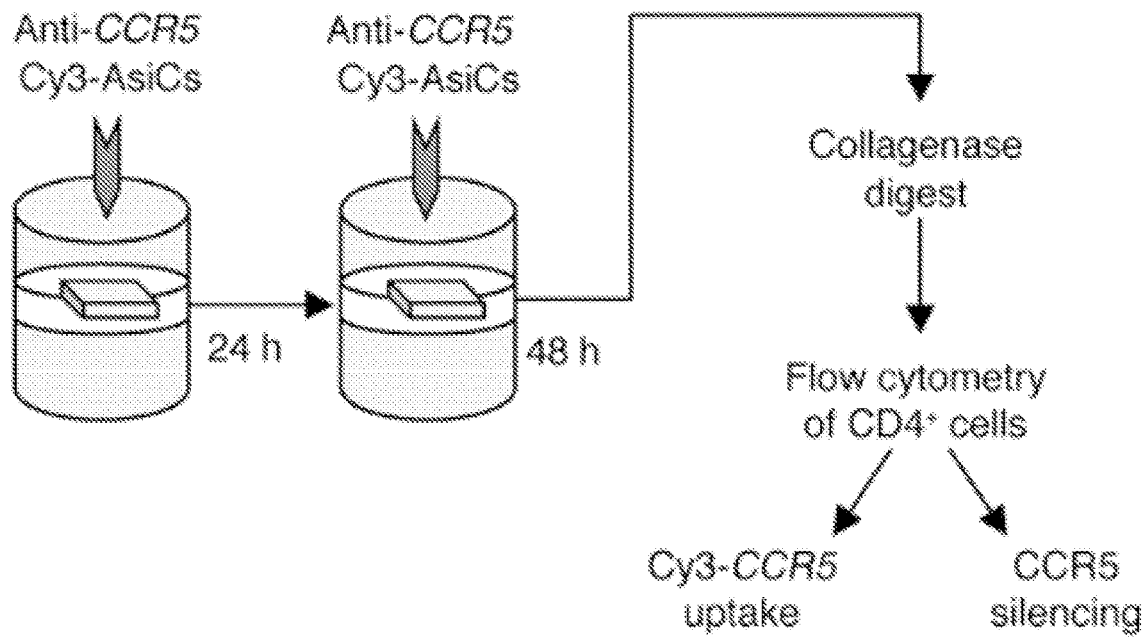
FIGS. 4A-4J show that CD4 aptamer-siRNA chimeras (CD4-AsiC) inhibit HIV replication in polarized human cervicovaginal explants.
Figure 4B:
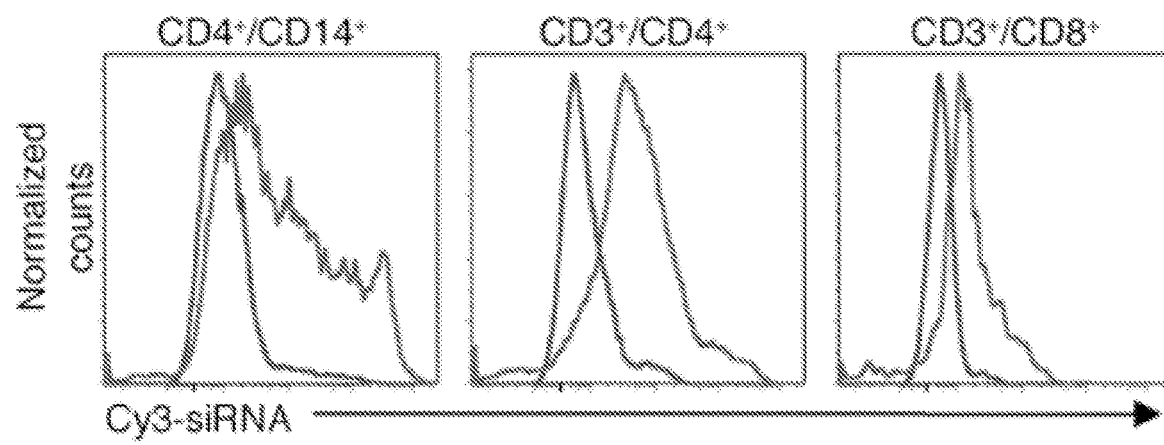
Figure 4C:
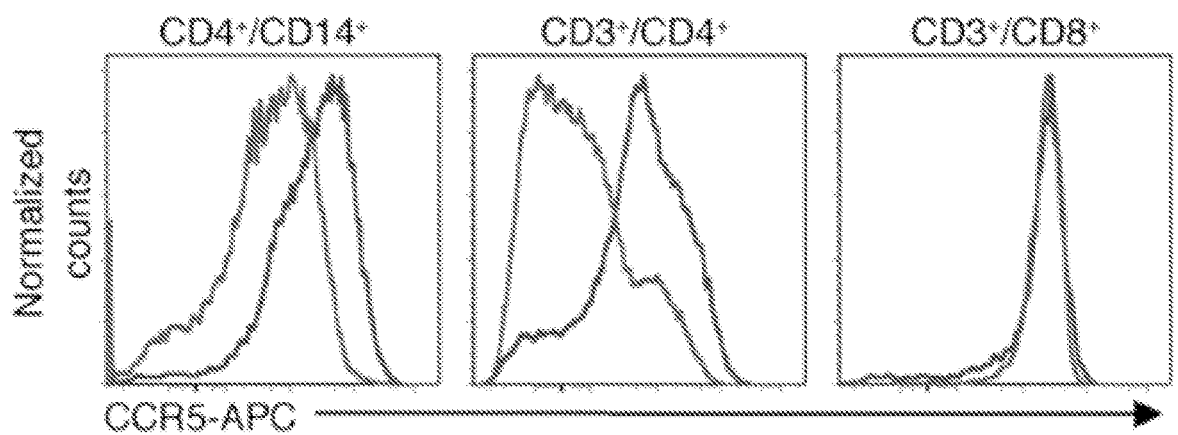
Figure 4D:
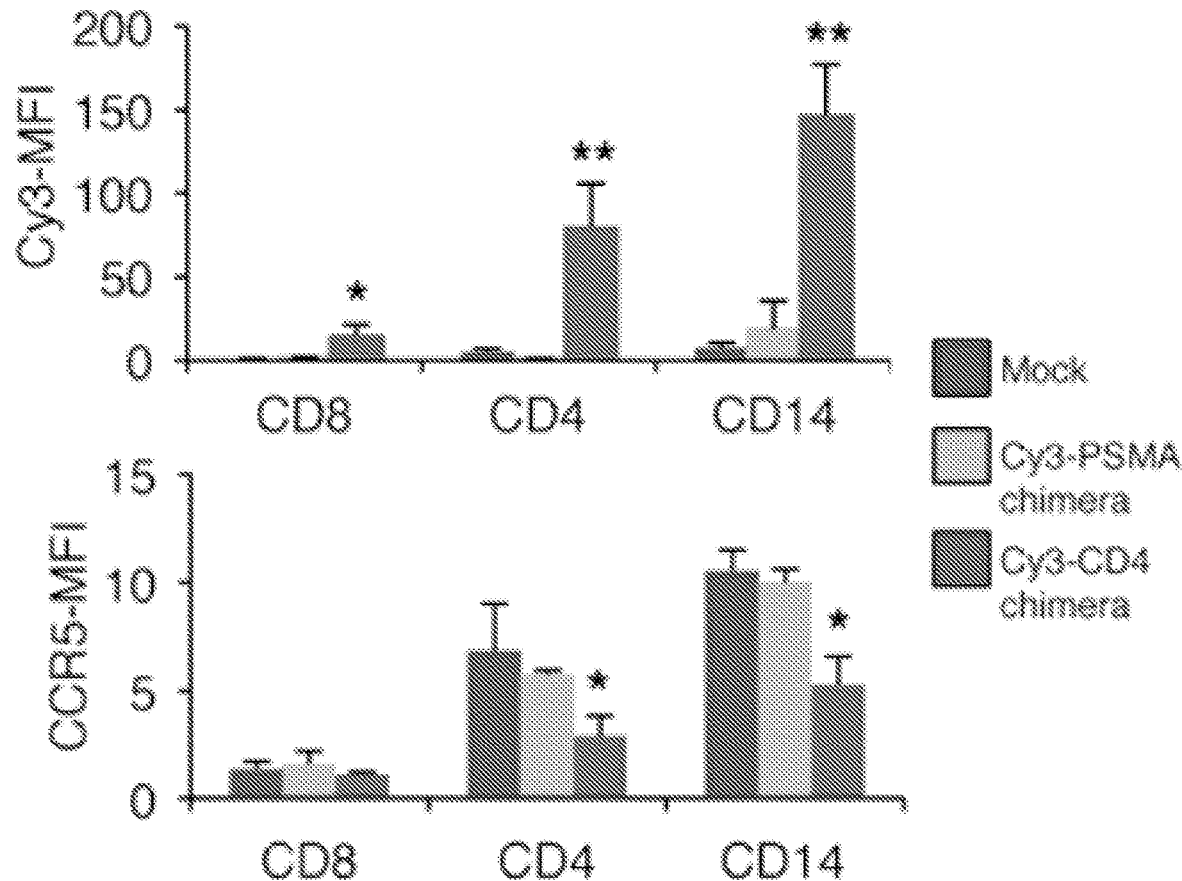
Figure 4E:
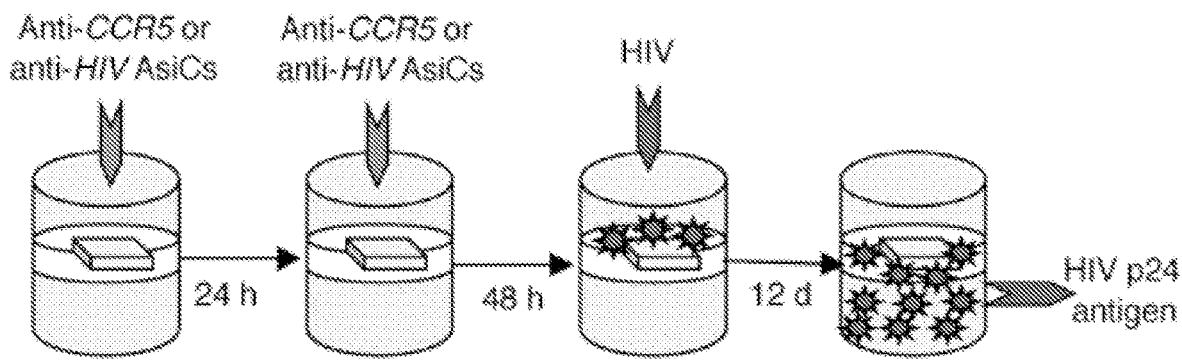

To assess whether CD4-AsiCs can penetrate the vaginal epithelium and specifically knockdown gene expression in CD4+ cells in intact human tissue, the apical surface of polarized agarose-embedded human cervicovaginal explants obtained from normal hysterectomy specimens (Greenhead, P. et al. *J Virol* 74, 5577-5586 (2000); Collins, K. B., et al., *Nat Med* 6, 475-479 (2000)) were treated with Cy3-labeled CCR5 CD4-AsiCs twice in a 24 h interval. Cy3 fluorescence and CCR5 was measured in isolated CD4+ and CD8+ T cells and CD14+ macrophages by flow cytometry 2 days after the second treatment (FIGS. 4A-4D). Cy3-labeled CD4-AsiCs were specifically taken up by CD4+ T cells and macrophages in situ and uniformly knocked down CCR5 expression. Despite nominal uptake by CD8+ cells, no gene silencing was observed in this population. Neither uptake nor CCR5 silencing was seen in tissues treated with PSMA-AsiCs (FIG. 4D). Topical application of CD4-AsiCs encoding a CD45 siRNA to explants also specifically knocked down CD45 expression only in CD4+ T cells and macrophages (data not shown).

Figure 4F:
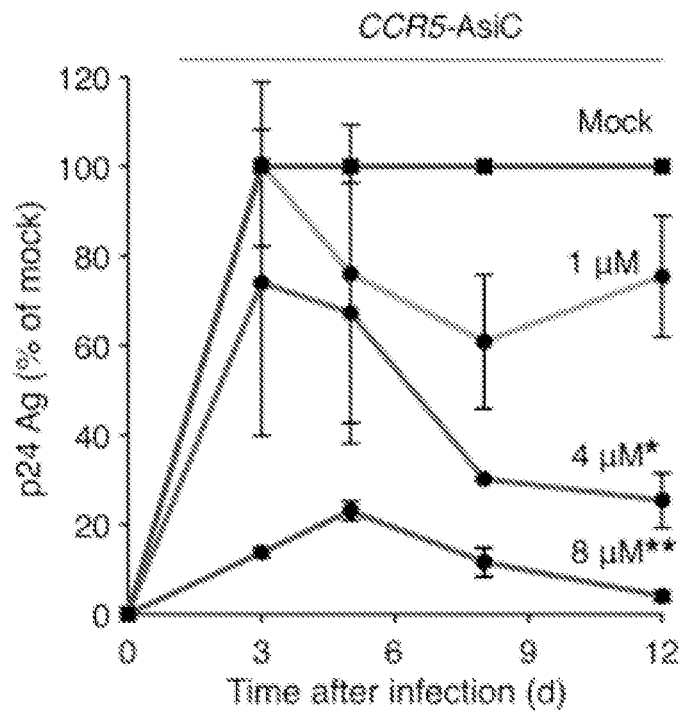
Figure 4G:
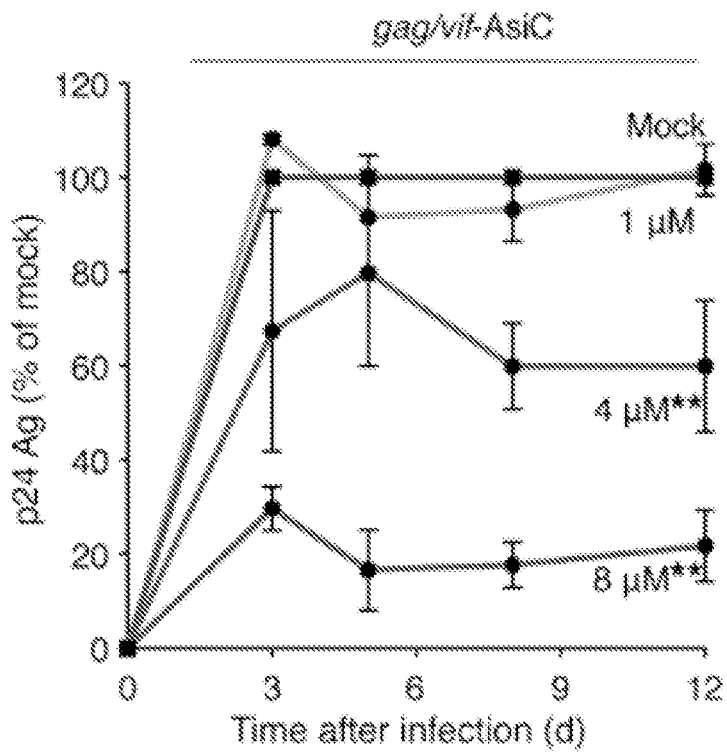
Figure 4H:
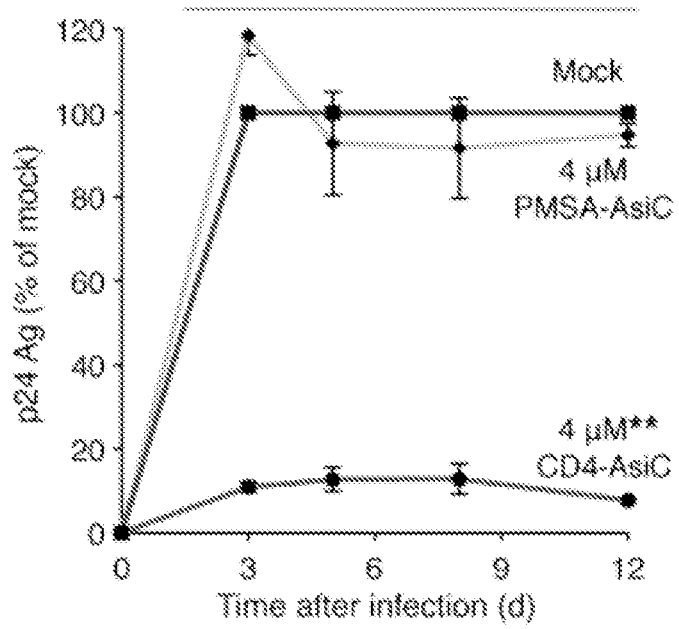
Figure 4I:
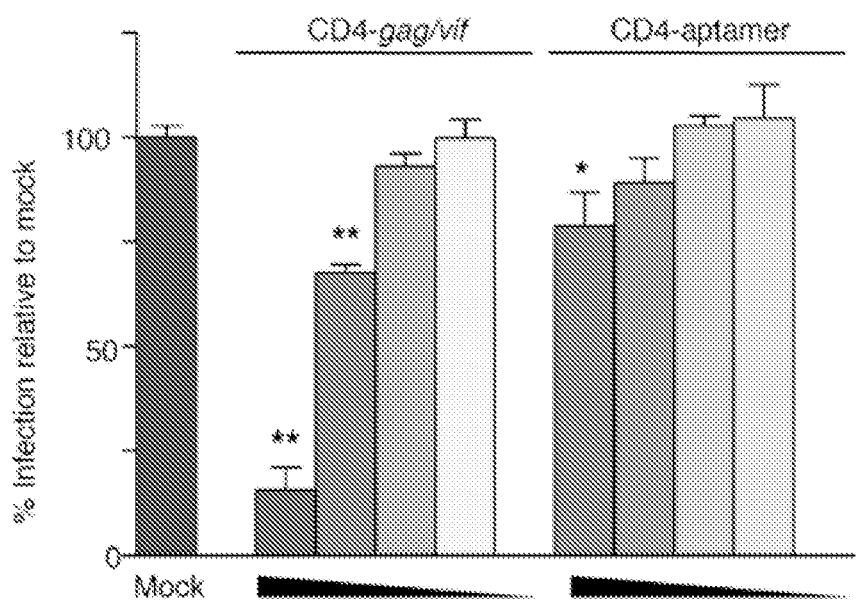
Figure 4J:
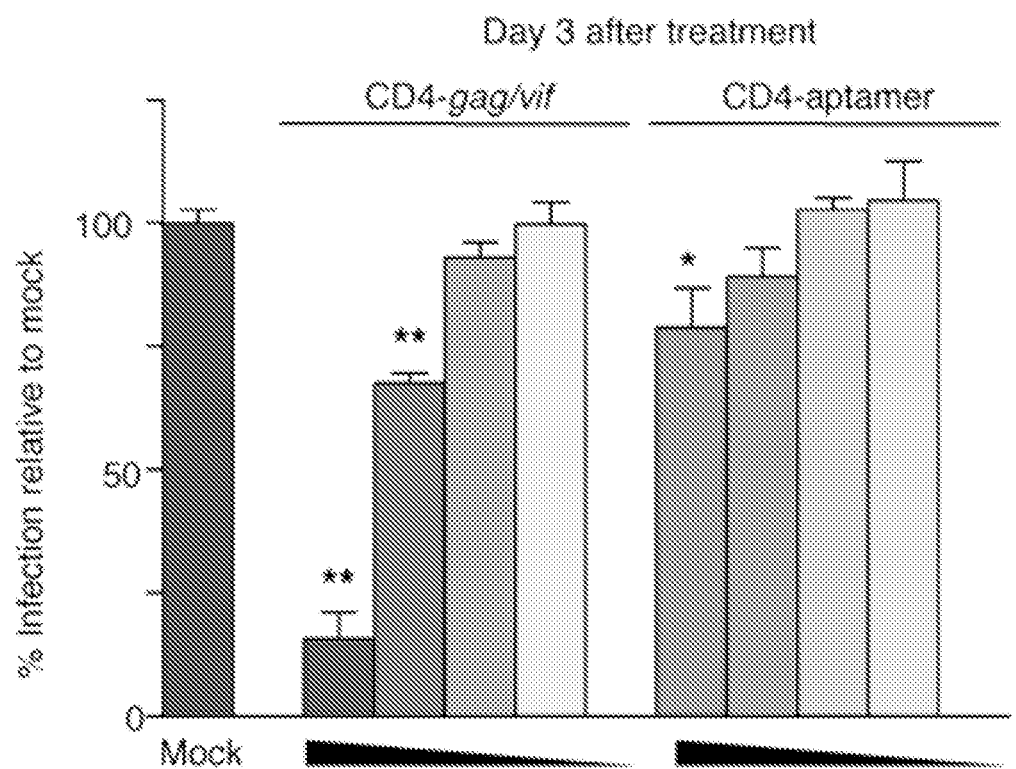

To determine whether antiviral CD4-AsiCs can block HIV transmission in intact vaginal tissue, the epithelial surface of polarized explants was treated twice with CD4-AsiCs containing siRNAs targeting gag and vif (FIG. 4F), CCR5 (FIG. 4G), or all three genes (FIG. 4H) before challenge with HIVBaL 48 h later. Mucosal viral replication, assessed by p24 Ag ELISA of the explant culture medium, was inhibited by CD4-AsiC treatment in a dose dependent manner. The triple cocktail administered at the same total concentration was more effective than either the antiviral or CCR5 CD4-AsiCs on their own. A triple cocktail of PSMA-AsiCs did not inhibit HIV transmission to the tissue. To assess the antiviral contribution of the CD4 aptamer, viral inhibition by the CD4 aptamer and the CD4-AsiCs encoding gag and vif siRNAs were compared in a dose response study, which suggests that although blocking CD4 binding contributes to HIV inhibition, the major antiviral activity of the CD4-AsiC is due to gene knockdown. The CD4 aptamer on its own inhibited HIV transmission in situ, but was about 2- to 4-fold less effective than the CD4-AsiCs (FIGS. 4I and 4J), which suggests that although blocking CD4 binding contributes to HIV inhibition, the major antiviral activity of the CD4-AsiC is due to gene knockdown.

CD4-AsiCs do not Trigger an Innate Immune Response in Human Cervicovaginal Tissue.

Figure 13A:
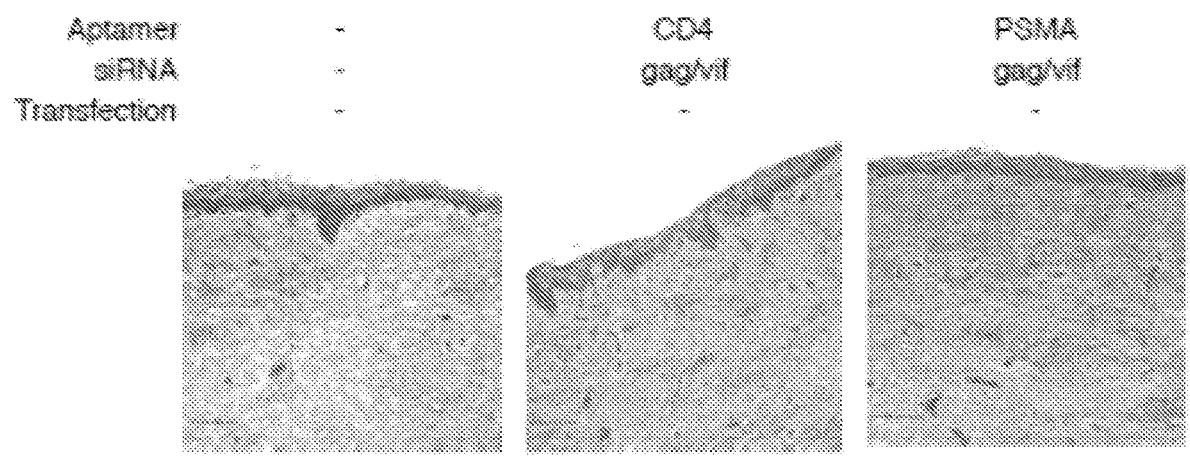
FIGS. 13A-13C show that treatment with CD4 aptamer-siRNA chimeras (CD4-AsiC) does not induce an interferon response or inflammation in polarized human cervicovaginal explants.
Figure 13B:
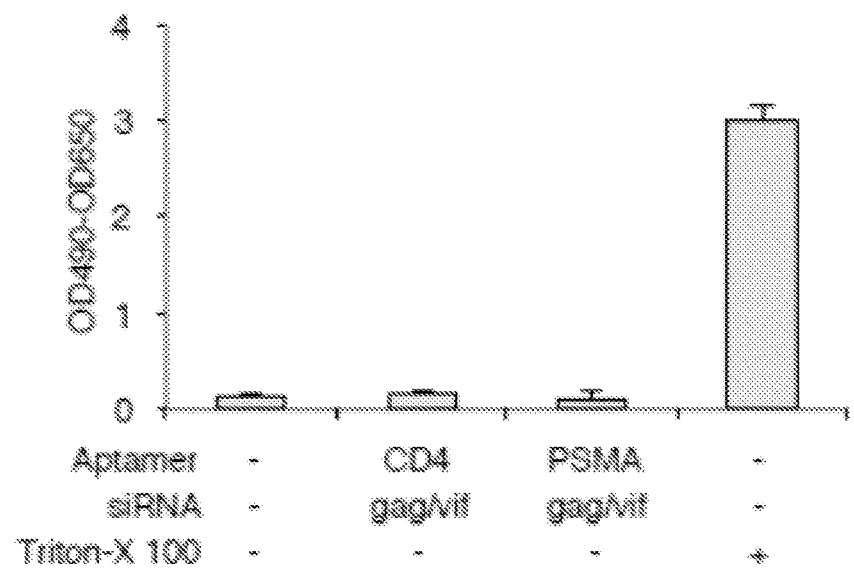
Figure 13C:
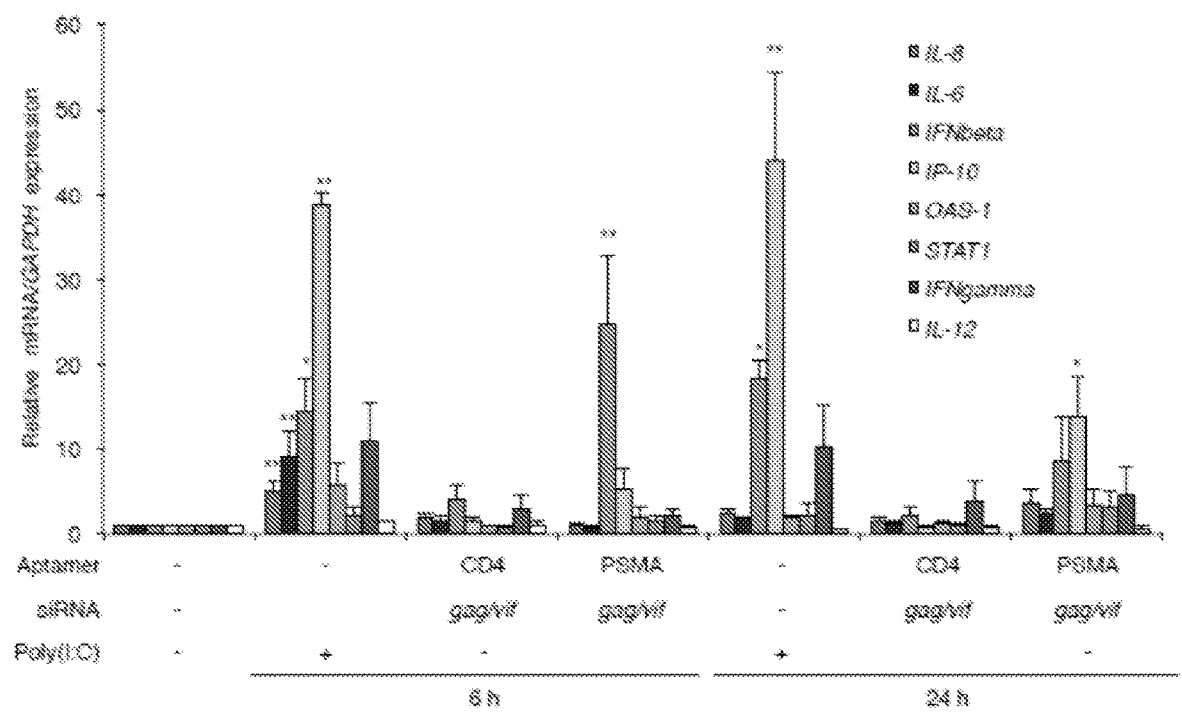

Depending on their sequence, concentration, chemical modifications, and delivery vehicle, siRNAs can trigger innate immune sensors that recognize foreign nucleic acids or cause cytotoxicity and tissue damage (Robbins, M., et al. *Oligonucleotides* 19, 89-102 (2009)). Moreover, the demonstrated antiviral effect could be a side effect of IFN induction by TLR or RIG-I activation. To examine whether CD4-AsiCs have any adverse or unanticipated off-target effects, polarized human explants were treated with gag and vif CD4-AsiCs at the same concentration (4 µM) that inhibited HIV inhibition and evaluated for tissue injury and inflammation by hematoxylin and eosin staining, cytotoxicity by LDII release, and induction of innate immune response genes (FIG. 13). The explants were treated with poly(I:C) as a positive control and mock treated as a negative control. There was no evidence of tissue injury or inflammation or cytotoxicity. Moreover, CD4-AsiCs did not induce IFINI3 or IFNy, inflammatory cytokines (IL-6, IL-8, IL-12) or IFN-responsive genes (IP-10, OAS-1, STAT]), as measured by sensitive qRT-PCR assay of RNA extracted from whole tissue harvested at their expected peak, 6 and 24 h after treatment. Contrary to a previously published report (McNamara, J. O., 2nd et al. *Nat Biotechnol* 24, 1005-1015 (2006)), the PSMA-AsiCstimulated IFNI3 expression at 6 h and IP-10 at 24 hr, likely reflecting the higher sensitivity of qRT-PCR relative to ELISA for measuring cytokine induction.

CD4-AsiCs Suppress Target Gene Expression in CD4+ Cells In Vivo.

Figure 17A:
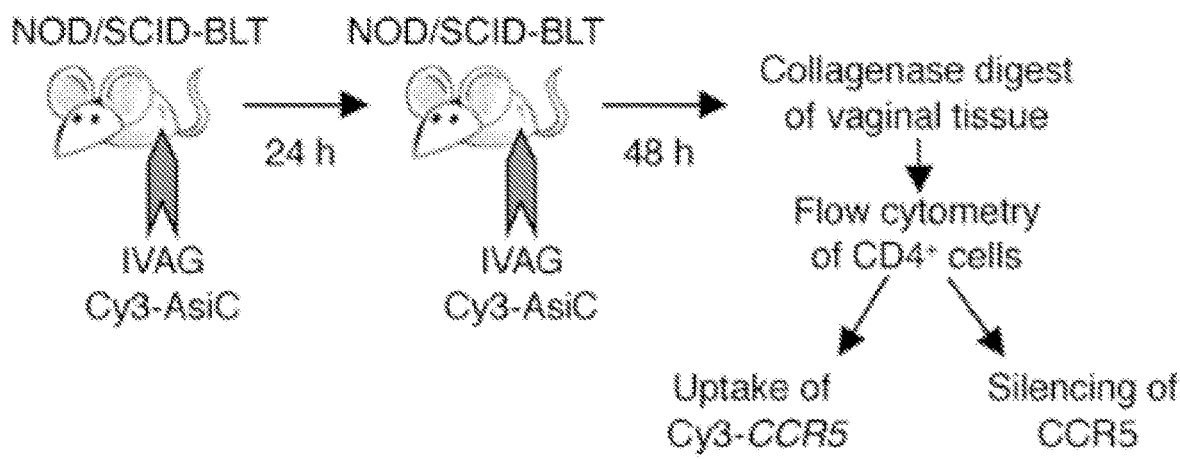
FIGS. 17A-17H show that CD4 aptamer-siRNA chimeras (CD4-AsiCs), applied intravaginally, inhibit HIV vaginal transmission to humanized BLT mice.
Figure 17B:
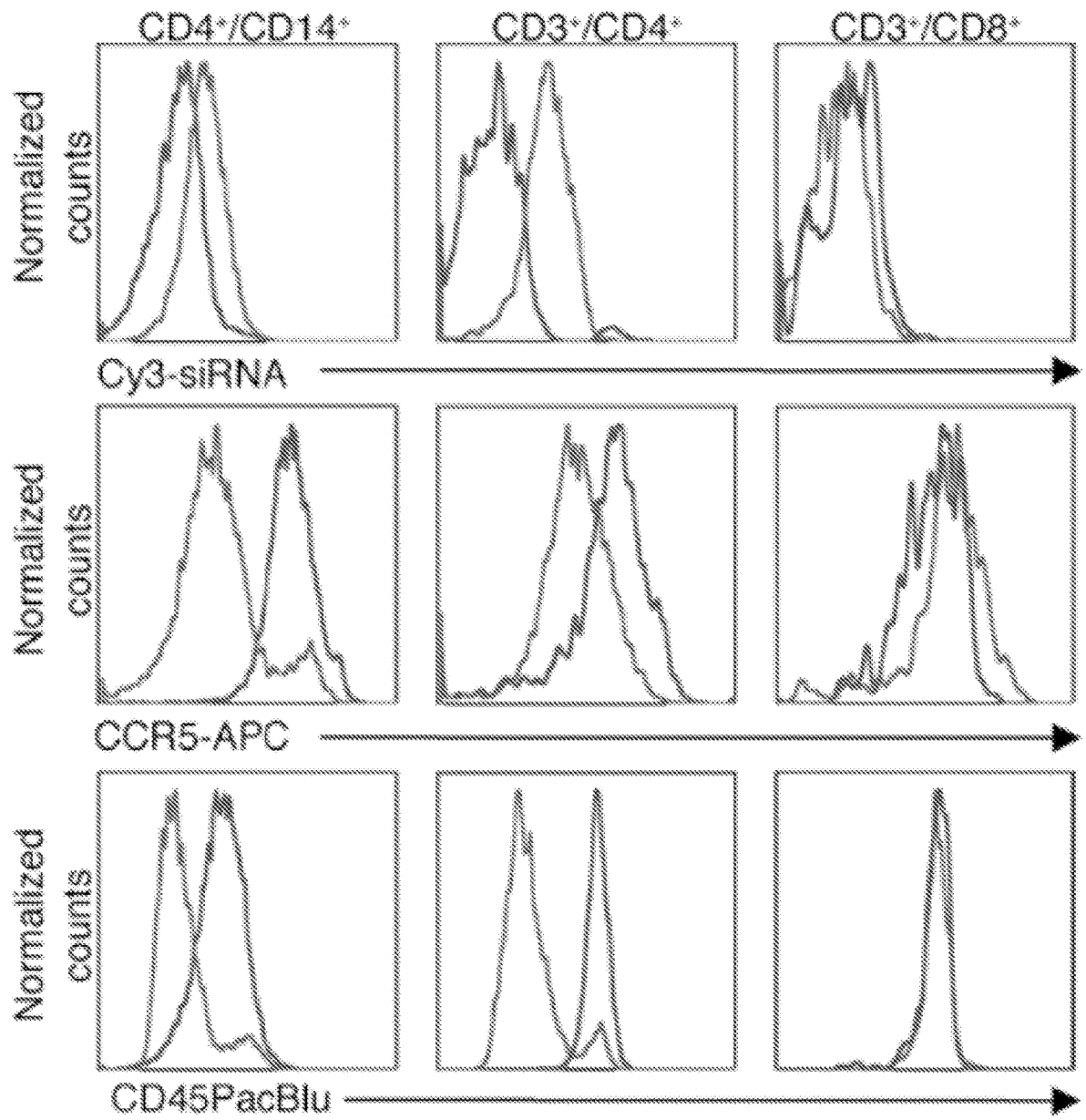
Figure 17C:
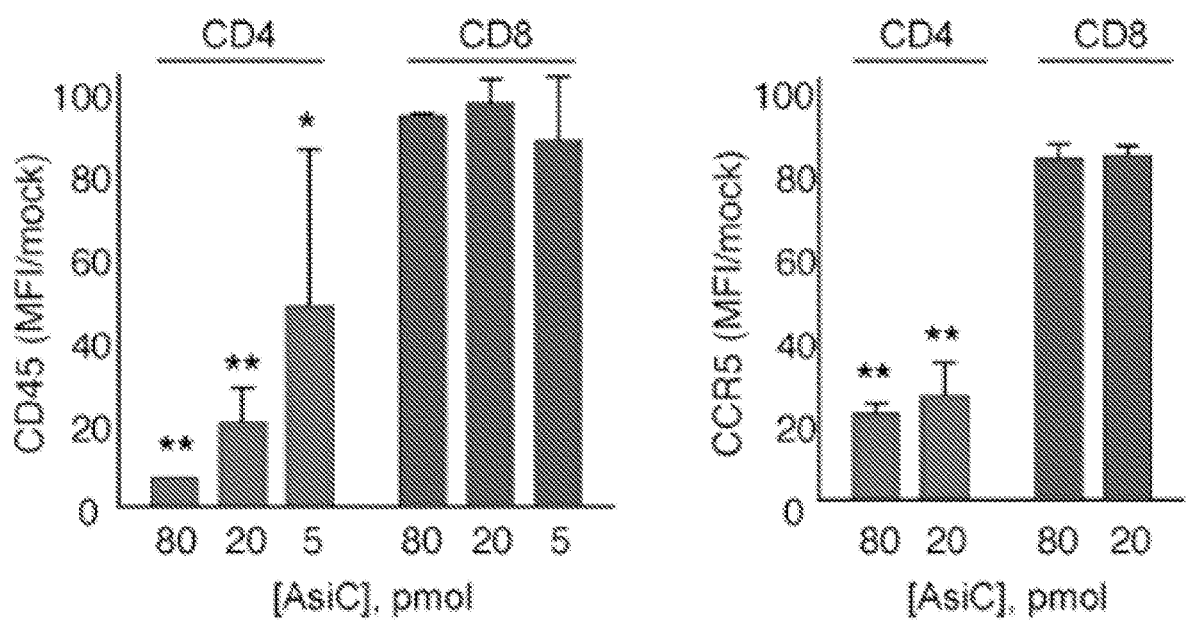

To validate the antiviral properties of CD4-AsiCs in vivo, the inventors used the BLT humanizerd mouse model (Brainard D M, et al. *J Virol.* 2009; 83(14):7305-7321), a humanized mouse model in which NOD/SCID mice are reconstituted with human bone marrow, liver and thymus ("BLT") (Shultz, E D., Ishikawa, F. & Greiner, D. L. Humanized mice in translational biomedical research. Nat Rev Immunol 7, 118-130 (2007)). A mixture of CD4-AsiCs bearing CD45 siRNAs and Cy3-labeled CCR5 siRNAs were applied IVAG to NOD/SCD-BLT mie, 2 hours and 48 hours prior to sacrifice, each at doses ranging from 5-80 pmol (FIG. 17A). To assess cell-specific siRNA delivery and gene knockdown in vivo, Cy3-fluorescence and CD45 and CCR5 expression in subpopulations of CD4+ and CD8+ cells were evaluated by flow cytometry of single cell suspensions of vaginal tissue and compared to mock-treated control mice (FIGS. 17B and 17C). Cy3 fluorescence uptake, was uniform in CD3+CD4+ T cells and CD14+CD4+ tissue macrophages, but was absent in tissue CD3+CD8+ T cells. Dose-dependent CCR5 and CD45 knockdown was observed in CD4+ T cells, but not in CD8+ T cells. At the highest CD4-AsiC dose, cell surface CD45 and CCR5 mean fluorescence intensity (MFI) in CD4+ T cells was reduced 12- and 5-fold, respectively relative to mock-treated controls.

Topically Applied CD4-AsiCs Inhibit Vaginal Transmission of HIV to Humanized Mice.

Figure 17D:
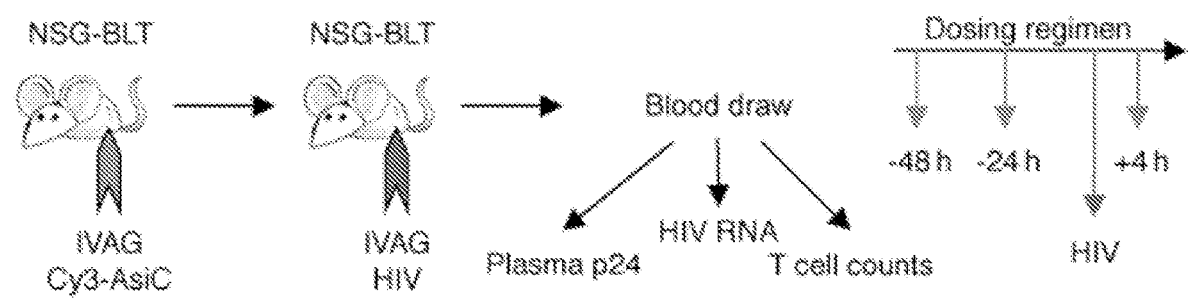
Figure 17E:
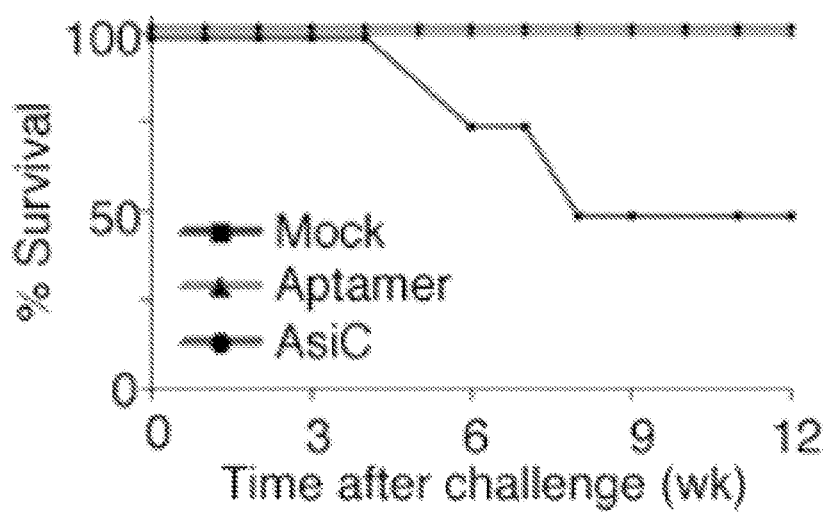
Figure 17F:
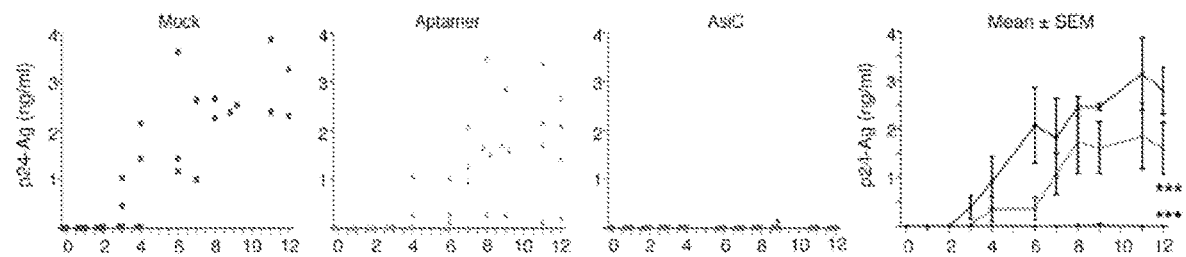
Figure 17G:
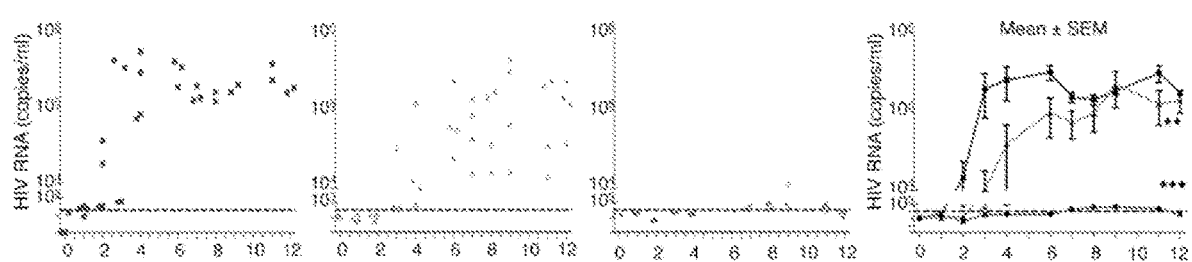
Figure 17H:
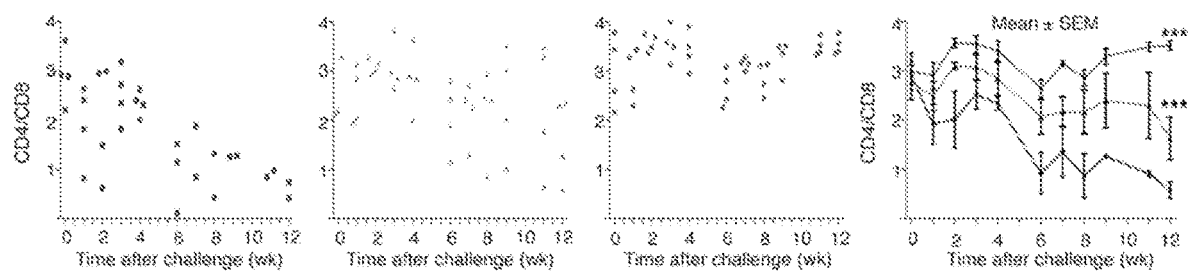
Figure 18:
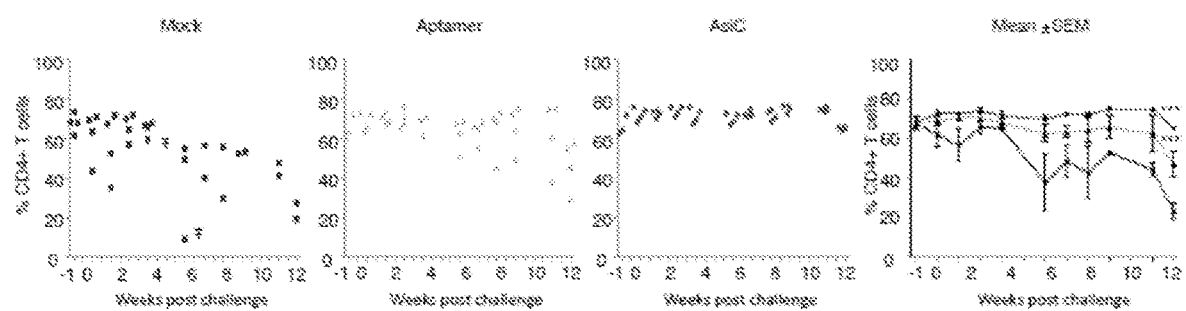
FIG. 18 shows that intravaginal application of CD4-aptamer-siRNA chimeras (AsiCs) maintains peripheral CD4+ T-cell counts in humanized BLT mice post vaginal HIV-1 challenge. NOD/SCID/IL2rg$^{-/-}$(NSG)-BLT mice were treated IVAG with CCR5 CD4-AsiCs 48 hr (80 pinol) and 24 hr (40 pmol) before and 40 pmol each of gag and vif CD4-AsiCs 24 h before and 4 h after IVAG challenge with HIVJR-csF. The CD4-AsiC-treated mice (N=4) were compared to mice treated with the same total dose of CD4-aptamers without siRNA conjugates (N=4) and with PBS-treated mock controls (N=4). Mice were observed for 12 weeks after HIV challenge, and the two mock-treated mice that died are marked by a *. The effect of treatment on peripheral blood CD4+ T cell counts is shown (mean±S.E.M, two-way ANOVA relative to mock with Bonferroni correction, ***p<0.0001). All the CD4-AsiC treated mice preserved their CD4 counts as did 2 of 4 aptamer-treated mice, but all the mock-treated mice showed a decline in CD4 counts. Shown is the percent of CD4+ CD3+ cells in PBMCs as determined by flow cytometry.

To test whether topically applied CD4-AsiCs protect humanized mice from vaginal HIV challenge, 4 NOD/SCID/ 7-/- (NSG)-BLT mice were treated with a combination of CD4-AsiCs targeting CCR5, gag and vif prior to 1VAG challenge with $10^5$-ICID$_{50}$ HIVix-csi·(FIG. 17D), a viral dose that uniformly infects control mice (data not shown, Berges, et al., Virology 373, 342-351 (2008) and Denton, P. W. et al. PLoS Med 5, e16 (2008)). The CCR5 AsiCs were administered 48 h and 24 h prior to challenge, and the viral gene-targeting AsiCs were administered 24 h prior and 4 h after IVAG challenge. Four mice were treated with equivalent doses of CD4 aptamers lacking siRNA conjugates, and 4 mice were treated with PBS using the same dosing regimen. In the 12 weeks of observation following challenge, all the aptamer and AsiC-treated mice survived, while two of the mock-treated mice died (FIG. 17E). Whereas all the control and aptamer-treated mice became infected and had detectable HIV p24 antigenemia 2-4 weeks after infection, none of the CD4-AsiC-treated mice developed detectable p24 antigenemia (FIG. 17F). Plasma viral burden, assessed by sensitive qRT-PCR assay for HIV gag mRNA, was detected at very low levels and only episodically several months later in the 2 of 4 CD4-AsiC-treated mice that became infected, a significant reduction compared with the mock-treated or aptamer-treated animals (FIG. 17G). All the control mice and two of the four aptamer-treated mice showed dramatic depletion of circulating CD4+ T cells, whereas all mice treated with CD4-AsiCs and the other 2 of the 4 aptamer-treated mice maintained relatively normal CD4 counts and stable CD4/CD8 ratios (FIGS. 17H and 18). Although the inventors did not directly determine the cause of death of the mock-treated mice, the profound depletion of their circulating CD4+ T cells in the 2 weeks prior to death may have been responsible. Thus, topical application of a mixture of CD4-AsiCs targeting CCR5 and HIV genes provided protection against vaginal challenge. Although the detection of plasma viremia and development of CD4+ T cell depletion were delayed in the aptamer-treated mice, their viral load was not significantly less than in mock-treated mice by the end of the observation period. Therefore, the CD4 aptamer, which inhibits I IVV from binding to CD4, was substantially less effective than the chimera, which can both block binding and suppress entry and viral replication by gene knockdown.

Delivery remains a significant obstacle to the clinical development of siRNA-based drugs. Although cholesterol-conjugated siRNAs silence gene expression without apparent toxicity in mucosal epithelial cells and can be used to prevent HSV-2 transmission (Wu, Y. et al. Cell Host Microbe 5, 84-94 (2009)), this approach cannot be used to inhibit HIV transmission since cholesterol-conjugated siRNAs do not transfect the cells that HIV infects. One approach to deliver siRNAs into immune cells is via antibody-mediated endocytosis either by complexing siRNAs to antibody fusion proteins or by encapsulating siRNAs into liposomes or other nanoparticles bearing targeting antibodies or ligands to cell surface receptors (Peer, D., et al. Proc Nail Acad Sci USA 104, 40954100 (2007); Kumar, P. et al. Cell 134, 577-586 (2008); Song, E. et al. Nat Biotechnol 23, 709-717 (2005); Peer, D., et al. Science 319, 627-630 (2008)). However, antibody-fused siRNAs are expensive to manufacture, potentially immunogenic and may require refrigerated storage, making them ill-suited for use in microbicide for resource-poor settings.

Accordingly, the invention provides another approach using chimeric RNAs composed of an aptamer linked to an siRNA that can transfect and knockdown gene expression specifically in primary CD4+ T cells and macrophages, irrespective of their activation state, both in vitro and in intact tissue in human explants and in humanized mice. Importantly the CD4-AsiCs were able to inhibit vaginal HIV transmission to humanized mice. Although only one of 4 CD4-AsiC-treated mice maintained undetectable virus throughout the 10-week period, all CD4-AsiC-treated mice showed preserved T cell counts and the 3 mice that became infected had significantly reduced viral burden, detected only after 7-8 weeks. These results were achieved without any optimization of the CD4-AsiCs for CD4 binding or gene silencing sequences, using an extremely high challenge virus dose that gave uniform infection of control mice. Without wishing to be bound by a theory, it can be easier to prevent sexual HIV transmission in humans, which is very inefficient, requiring hundreds of exposures for each transmission event, and where usually only a single virion is able to establish a foothold in the host (Haase, A. T. Nature 464, 217-223). Protection was achieved here with a highest dose of −0.2 mg/kg (120 pmol), which is a feasible dose for small RNA drugs (Haase, A. T., Nature, 464, 217-223). However, this dose can be reduced further with drug optimization and using oligonucleotide modifications described herein. Furthermore, RNAi-based microbicides can be intermittently dosed to improve compliance and to provide long lasting gene silencing and protection in the genital tissue.

Targeted delivery has the dual advantage of reduced toxicity to bystander cells and a reduced effective dose. Chimeric RNAs have the advantage of being a single molecule rather than a complex mixture, are less likely to be immunogenic than proteins, and are more straightforward to purify and less costly to produce than RNAs that need to be formulated with proteins, nanoparticles, or liposomes. CD4-AsiCs were shown to knockdown two viral genes, a transgene (luciferase) and four host genes (CCR5, CD45, lamin A, EG5), and can be designed to inhibit the expression of any gene. The kinetics of target gene suppression may differ between targets, depending on target gene mRNA and protein stability. For example, CCR5 and CD45 surface protein expression was not appreciably reduced until 72 hours after CD4-AsiC treatment. However, mRNA levels of these genes, when measured by qRT-PCR, declined within a day.

Previous studies have shown that intravenous injection of PSMA-AsiCs leads to transfection of human prostate cancer cells in an orthotopic mouse tumor model (McNamara, J. O., 2nd et al. Nat Biotechnol 24, 1005-1015 (2006); Dassic, J. P. et al. Nat Biotechnol 27, 839-849 (2009)) or using HIV gp120-AsiCs leads to transfection of HIV-infected CD4+ cells in vitro (Zhou, J., et al. Mol Ther 16, 1481-1489 (2008); Zhou, J. et al. Nucleic Acids Res 37, 3094-3109 (2009); and Neff C P, et al. Sci Transl Med. 2011; 3(66):66ra66). Accordingly, the CD4-AsiCs conjugates described herein can be used for systemic gene silencing in circulating immune cells. Work presented herein has shown effective and specific gene knockdown in all human CD4+ immune cells in the female genital tract after IVAG application of CD4-AsiCs to immunodeficient mice reconstituted with human bone marrow, liver and thymus (FIGS. 17A-17H). The aptamer-siRNA conjugates described herein can inhibit HIV vaginal transmission and can specifically and effectively knockdown gene expression in lymphoid tissues in humanized mice after intravenous injection. Furthermore, the aptamer-siRNA conjugate described herein can be a potent tool to harness the power of genetic manipulation, which has been so powerful for understanding mouse immunology using knockout mice, to study the role of individual molecules in complex human immune responses in vivo. For example in humanized mice. Because CD4-AsiCs do not appear to perturb CD4 cell surface expression or alter other immune receptors that are sensitive indicators of immune activation, one can test the effect of knocking down one gene product at a time. The lack of cellular toxicity of CD4-AsiCs can also make them an attractive alternative to electroporation for in vitro transfection of CD4$^{+}$'1' cells. The clone 9 aptamer also recognizes Rhesus macaque CD4 and the corresponding CD4-AsiC knocks down gene expression in rhesus PBMCs both in vitro and intravaginally in vivo (data not shown), indicating that CD4-AsiCs can also be used to study SIV or SHIV infection and immune responses in non-human primates.

The micromolar concentrations of CD4-AsiCs, used herein for gene knockdown and HIV inhibition are higher than those needed in previous studies in which constructs had been optimized. Accordingly, CD4-AsiC design and/or synthesis can increase silencing efficiency. These CD4-AsiC design and/or synthesis can be improved by optimizing the aptamer or siRNA sequence, altering the linker joining the aptamer to the siRNA, interchanging the two siRNA strands, or replacing the double-stranded siRNA with a stem-loop that mimics endogenous miRNA structures. Some of these changes have been used in earlier studies, where the optimal AsiC construct depended on the particular siRNA sequence (Novina C D, et al. siRNA-directed inhibition of IIIV-1 infection. Nat Med. 2002, 8(7):681-686; Wu Y, et al. Cell Host Microbe. 2009, 5(1):84-94; McNamara J O 2nd, et al. Nat Biotechnol. 2006, 24(8):1005-1015; Dassie, J. P. et al. Nat Biotechnol 27, 839-849 (2009); and Zhou, J. et al. Nucleic Acids Res 37, 3094-3109 (2009)).

Without wishing to be bound by a theory, the CD4-AsiCs can be processed within cells by the endogenous RNAi machinery, (probably by Dicer), to cleave the chimera and release the active siRNA. Thus CD4-AsiCs can include modifications that lead to enhanced intracellular processing to the mature siRNA and its incorporation into the RNA-induced silencing complex.

While chemical synthesis of oligonucleotides has become routine, the aptamer sequence can be shorten to make chemical synthesis more practical. It is well known in the art that parts of the aptamer the aptamer sequence can be deleted without losing binding affinity. The aptamer and the siRNAs can be synthesized separately and joined together using complementary sequences (Zhou, J., Mol Ther 16, 1481-1489 (2008); Zhou, J. et al. Nucleic Acids Res 37, 3094-3109 (2009)).

Despite the high concentrations required in vitro, CD4-AsiC-mediated in vivo silencing and protection from HIV infection required significantly lower doses (about 7-25 times less) than were used to inhibit IISV-2 transmission with lipoplexed or cholesterol-conjugated siRNAs (Palliser D, et al. Nature. 2006; 439(7072):89-94 and Wu Y, et al. Cell Host Microbe. 2009; 5(1):84-94.). The stability of the CD4-AsiCs over 36 hours in human vaginal fluid suggests that further stabilization for topical use may not be required. Regardless, the in vivo half-life in the blood and other body fluids and within cells, as well as the efficiency and durability of gene knockdown, can be improved by further chemical modifications.

Without wishing to be bound by a theory, in vivo half-life in the blood and other body fluids and within cells, can be increased by chemically modifying the aptamer-siRNA conjugate. For example, chemical modifications, such as introduction of 2'-OCH$_3$ to purines on the active strand of the siRNA, can improve the efficiency and durability of silencing. For systemic use, chemical conjugation to cholesterol or polyethylene glycol can also improve circulating half-life and uptake by CD4 cells (Dassie, J. P. et al. Nat Biotechnol 27, 839-849 (2009); Soutschek, J. et al. Nature 432, 173178 (2004)).

The pathway used to deliver RNAs into cells, whether by aptamer binding to cell surface receptors or other means, remains poorly understood (Dominska, M. & Dykxhoorn, D. M. J Cell Sci 123, 1183-1189).

The pathways used to deliver RNAs into cells, whether by aptamers or by other delivery methods, remain poorly understood. Results presented herein indicate that Cy3-labeled CD4-AsiCs are initially taken up into early endosomes and then escape to the cytosol. Endocytosis can be triggered by activation of the CD4 receptor by aptamer binding or occur via the continuous basal internalization of cell surface receptors. The latter pathway may be more likely, since CD4 cell surface expression is not appreciably altered by CD4-AsiC treatment and since CD4-AsiCs are monomeric and arc not expected to crosslink the receptor. Although lack of perturbation of CD4 surface expression can be ideal for using CD4-AsiCs as a research tool, a divalent or polyvalent reagent that activates temporary CD4 internalization canal so have advantages for HIV prevention or therapy. This can add a third mechanism for inhibiting HIV cellular transmission (removal of the viral receptor from the cell surface) to the other 2 mechanisms demonstrated in the present study (gene silencing and partially blocking the virion binding site on CD4).

Since HIV only infects cells bearing the CD4 receptor, CD4 aptamer-siRNA chimeras (CD4-AsiC) can inhibit infection of all the cells that HIV infects. To test the ability to CD4-AsiCs to inhibit HIV transmission, AsiCs were engineered using two high affinity CD4 aptamers that selectively bind to human, but not mouse, CD43. CD4-AsiCs can inhibit HIV infection in two ways-by blocking viral entry by binding to CD4 and by RNAi knockdown of viral genes, host receptors or other host genes needed for viral replication. CD4-AsiCs encoding siRNAs targeting HIV genes or CCR5 were specifically taken up by CD4+ cells, knocked down expression of their intended target genes, and inhibited HIV infection in primary CD4+ T cells and macrophages in vitro and in polarized cervicovaginal explants and in immunodeficient mice transplanted with fetal human bone marrow, liver and thymus ("BLT mice"). While the aptamer on its own inhibited HIV infection to some extent, chimeric RNAs were more effective at preventing transmission to cervicovaginal explants and to BLT mice.

TABLE 1

Primer and Template DNA sequences.

5' Primers

| Name | Sequence | SEQ ID NO |
|---|---|---|
| 5' T7 Primer CD4 | 5'-TAA TAC GAC TCA CTA TAG GGA GAC AAG AAT AAA CGC-3' | SEQ ID NO: 1 |
| 5'T7 Primer A10 | 5'-TAA TAC GAC TCA CTA TAG GGA GGA GGA CGA TGC GGA-3' | SEQ ID NO: 2 |

Template DNA

| Name | Sequence | SEQ ID NO |
|---|---|---|
| CD4 Clone 9 Aptamer | 5'-GGG AGA CAA GAA TAA ACG CTC AAT GAC GTC CTT AGA ATT GCG CAT TCC TCA CAC AGG ATC TTTT TCG ACA GGA GGC TCA CAA CAG GC-3' | SEQ ID NO: 3 |
| CD4 Clone 12 Aptamer | 5'-GGG AGA CAA GAA TAA ACG CTC AAG TGA CGT CCT GAT CGA TTG TGC ATT CGG TGT GAC GAT CTT TCG ACA GGA GGC TCA CAA CAG GC-3' | SEQ ID NO: 4 |
| PSMA A10 Aptamer | 5'-GGG AGG ACG ATG CGG ATC AGC CAT GTT TAC GTC ACT CCT TGT CAA TCC TCA TCG GCA GAC TCG CCC GA-3' | SEQ ID NO: 5 |

3' Primers

| Name | Sequence | SEQ ID NO |
|---|---|---|
| 3' No siRNA Primer CD4 | 5'-GCC TGT TGT GAG CCT CCT GTC GAA-3' | SEQ ID NO: 6 |
| 3' No siRNA Primer A10 | 5'-TCG GCG AGT CGT CGT CT GCC GAT G-3' | SEQ ID NO: 7 |
| 3' Scrambled siRNA CD4 | 5'-AAT TCT CCG AAC GTC TCA CGT GCC TGT TGT GAG CCT CCT GTC GAA-3' | SEQ ID NO: 8 |
| 3' Scrambled siRNA A10 | 5'-AAT TCT CCG AAC GTC TCA CGT TCG GGC GAG TCG TCG TCT GCC GAT G-3' | SEQ ID NO: 9 |
| 3' CCR5 Primer CD4 | 5'-AAT TTC GAC ACC GAA GCA GAG GCC TGT TGT GAG CCT CCT GTC GAA-3' | SEQ ID NO: 10 |
| 3' CCR5 Primer A10 | 5'-AAT TTC GAC ACC GAA GCA GAG TCG GGC GAG TCG TCG TCT GCC GAT G-3' | SEQ ID NO: 11 |
| 3' lamin Primer CD4 | 5'-AAT GTT CTT CTG GAA GTC CAG GCC TGT TGT GAG CCT CCT GTC GAA-3' | SEQ ID NO: 12 |
| 3' lamin Primer A10 | 5'-AAT GTT CTT CTG GAA GTC CAG TCG GGC GAG TCG TCG TCT GCC GAT G-3' | SEQ ID NO: 13 |
| 3' gag Primer CD4 | 5'-AAC CTG TCT CTC AGT ACA ATC GCC TGT TGT GAG CCT CCT GTC GAA-3' | SEQ ID NO: 14 |
| 3' gag Primer A10 | 5'-AAC CTG TCT CTC AGT ACA ATC TCG GGC GAG TCG TCG TCT GCC GAT G-3' | SEQ ID NO: 15 |
| 3' vif Primer CD4 | 5'-AAG GGA TGT GTA CTT CTG AAC GCC TGT TGT GAG CCT CCT GTC GAA-3' | SEQ ID NO: 16 |
| 3' vif Primer A10 | 5'-AAG GGA TGT GTA CTT CTG AAC TCG GGC GAG TCG TCG TCT GCC GAT G-3' | SEQ ID NO: 17 |
| 3' EG5 Primer | 5'-AAA TTG TCT TCA GGT CTT CAG GCC TGT TGT GAG CCT CCT GTC GAA-3' | SEQ ID NO: 18 |
| 3' CD45 Primer | 5'-AAT GCT CTG AAA TTC AGC AGC CTG TTG T GAG CCT CCT GTC GAA-3' | SEQ ID NO: 19 |
| 3' Luciferase Primer | 5'-AAT CGA AGT ACT CAG CGT AAG CCT GTT GT GAG CCT CCT GTC GAA-3' | SEQ ID NO: 20 |

Primer sequences used in this study.

| Name | Sequence | SEQ ID NO |
|---|---|---|
| Lamin For | 5'-TGA GAA CAG GCT GCA GAC CAT GAA-3' | SEQ ID NO: 21 |
| Lamin Rev | 5'-CAA ACT CAC GCT GCT TCC CAT TGT-3' | SEQ ID NO: 22 |
| GAPDH For | 5'-AGC CAC ATC GCT CAG ACA C-3' | SEQ ID NO: 23 |

TABLE 1-continued

Primer and Template DNA sequences.

| | | |
|---|---|---|
| GAPDH Rev | 5'-GCC CAA TAC GAC CAA ATC C-3' | SEQ ID NO: 24 |
| IL-8 For | 5'-AGA CAG CAG AGC ACA CAA GC-3' | SEQ ID NO: 25 |
| IL-8 Rev | 5'-ATG GTT CCT TCC GGT GGT-3' | SEQ ID NO: 26 |
| IL-6 For | 5'-GAT GAG TAC AAA AGT CCT GAT CCA-3' | SEQ ID NO: 27 |
| IL-6 Rev | 5'-CTG CAG CCA CTG GTT CTG T-3' | SEQ ID NO: 28 |
| IFNl3 For | 5'-TTG CTC TGG CAC AAC AGG TA-3' | SEQ ID NO: 29 |
| IFNl3 Rev | 5'-TGG AGA AGC AAC CAG GAG A-3' | SEQ ID NO: 30 |
| IFNγ For | 5'-GGC ATT TTG AAG AAT TGG AAA G-3' | SEQ ID NO: 31 |
| IFN-γ Rev | 5'-TTT GGA TGC TCT GGT CAT CTT-3' | SEQ ID NO: 32 |
| OAS-1 For | 5'-GGT GGA GTT CGA TGT GCT G-3' | SEQ ID NO: 33 |
| OAS-1 Rev | 5'-AGG TTT ATA GCC GCC AGT CA-3' | SEQ ID NO: 34 |
| IP-10 For | 5'-GAA AGC AGT TAG CAA GGA AAG GT-3' | SEQ ID NO: 35 |
| IP-10 Rev | 5'-GAC ATA TAC TCC ATG TAG GGA AGT GA-3' | SEQ ID NO: 36 |
| STAT1 For | 5'-TTG GCA CCT AAC GTG CTG-3' | SEQ ID NO: 37 |
| STAT1 Rev | 5'-TTC GTA CCA CTG AGA CAT CCT G-3' | SEQ ID NO: 38 |
| IL-12 For | 5'-CAC TCC CAA AAC CTG CTG CTG AG-3' | SEQ ID NO: 39 |
| IL-12 Rev | 5'-TCT CTT CAG AAG TGC AAG GGT A-3' | SEQ ID NO: 40 |
| HIV-gag For | 5'-AGT GGG GGG ACA TCA AGC AGC CAT GCA AAT-3' | SEQ ID NO: 41 |
| HIV-gag Rev | 5'-TGC TAT GTC ACT TCC CCT TGG TTC TCT-3' | SEQ ID NO: 42 |

TABLE 3

Exemplary siRNA sequences.

| | | |
|---|---|---|
| CCR5 | Sense: 5' P-CUC UGC UUC GGU GUC GAA A dTdT-3'<br>Antisense: 5' P-UUU CGA CAC CGA AGC AGA G dTdT-3' | SEQ ID NO: 43<br>SEQ ID NO: 44 |
| gag | Sense: 5' P-GAU UGU ACU GAG AGA CAG GCU-dTdT-3'<br>Antisense: 5' P-CCU GUC UCU CAG UAC AAU CdTdT-3' | SEQ ID NO: 45<br>SEQ ID NO: 46 |
| vif | Sense: 5' P-GTT CAG AAG TAC ACA TCC C-dTdT<br>Antisense: 5' P-GGG AUG UGU ACU UCU GAA CdTdT-3' | SEQ ID NO: 47<br>SEQ ID NO: 48 |
| Luciferase | Sense: 5' P-CUU ACG CUG AGU ACU UCG AdTdT-3'<br>Antisense: 5' P-UCG AAG UAC UCA GCG UAA GdTdT-3' | SEQ ID NO: 49<br>SEQ ID NO: 50 |
| CD45 | Sense: 5' P-CUG GCU GAA UUU CAG AGC AdTdT-3'<br>Antisense: 5' P-UGC UCU GAA AUU CAG CCA GdTdT-3' | SEQ ID NO: 51<br>SEQ ID NO: 52 |
| Lamin | Sense: 5' P-CUG GAC UUC CAG AAG AAC AdTdT-3'<br>Antisense: 5' P-UGU UCU CUU GGA AGU CCA GdTdT-3' | SEQ ID NO: 53<br>SEQ ID NO: 54 |
| Eg5 | Sense: 5' P-CUG AAG ACC UGA AGA CAA UdTdT-3'<br>Antisense: 5' P-AUU GUC UUC AGG UCU UCA GdTdT-3' | SEQ ID NO: 55<br>SEQ ID NO: 56 |
| CCR5<br>without 5'<br>phosphate | Sense: 5'-CUC UGC UUC GGU GUC GAA A dTdT-3'<br>Antisense: 5'-UUU CGA CAC CGA AGC AGA G dTdT-3' | SEQ ID NO: 57<br>SEQ ID NO: 58 |
| Sense + linker:<br>CCR5 with<br>linker | 5'-CUC UGC UUC GGU GUC GAA AUU-(3C)-UGC CUG UUG-3' (3C = 3 carbon linker)<br>Antisense: 5'-UUU CGA CAC CGA AGC AGA G dTdT-3' | SEQ ID NOS 59<br>and 75<br>SEQ ID NO: 58 |
| | Sense: 5'-AAG GGC GGU UUU GCA AGU G-3'<br>Antisense: 5'-CAC UUG CAA AAC CGC CCA AdTdT-3' | SEQ ID NO: 60<br>SEQ ID NO: 61 |

TABLE 4

Exemplary aptamer RNA sequences.

| | | |
|---|---|---|
| CD4 Clone 9 Aptanner | 5'-GGG AGA CAA GAA UAA ACG CUC AAU GAC GUC CUU AGA AUU GCG CAU UCC UCA CAC AGG AUC UUU UCG ACA GGA GGC UCA CAA CAG GC-3' | SEQ ID NO: 62 |
| CD4 Clone 12 Aptanner | 5'-GGG AGA CAA GAA UAA ACG CUC AAG UGA CGU CCU GAU CGA UUG UGC AUU CGG UGU GAC GAU CUU UCG ACA GGA GGC UCA CAA CAG GC-3' | SEQ ID NO: 63 |
| PSMA A10 Atamer | 5'-GGG AGG ACG AUG CGG AUC AGC CAU GUU UAC GUC ACU CCU UGU CAA UCC UCA UCG GCA GAC UCG CCC GA-3' | SEQ ID NO: 64 |
| Truncated CD4 aptanner (5'-loop) | 5'-CUC AAU GAC GUC CUU AGA AUU GCG-3' | SEQ ID NO: 65 |
| Truncated CD4 aptanner (3'-loop) | 5'-UUC CUC ACA CAG GAU CUU UUC GAC AGG AGG-3' | SEQ ID NO: 66 |

20

TABLE 5

Exemplary conjugates

Figure 14A:
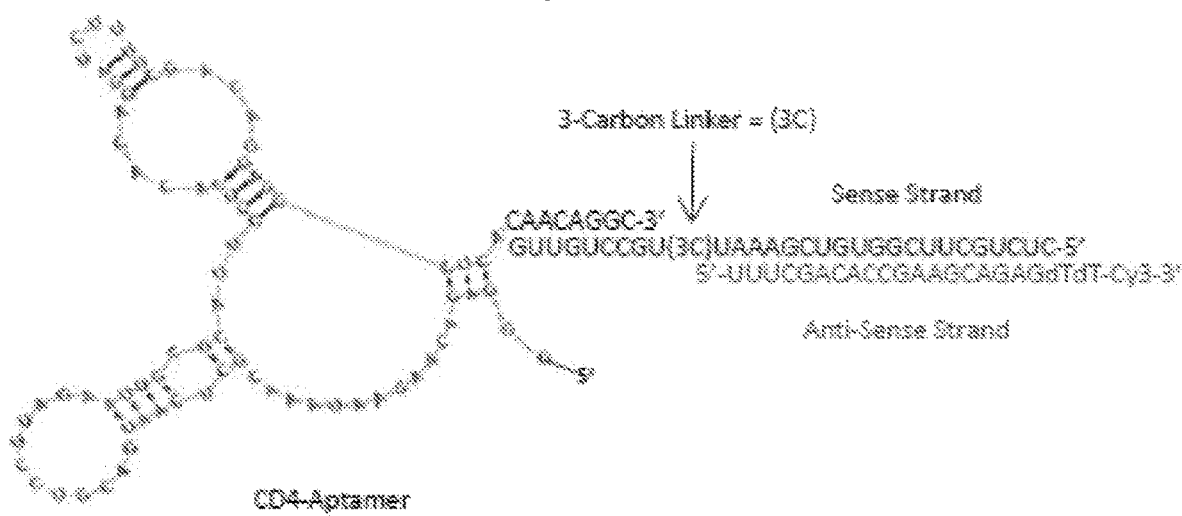
FIGS. 14A-14C show CCR5 silencing in CD4+ T cells using two different aptamer-siRNA conjugates.
Figure 14B:
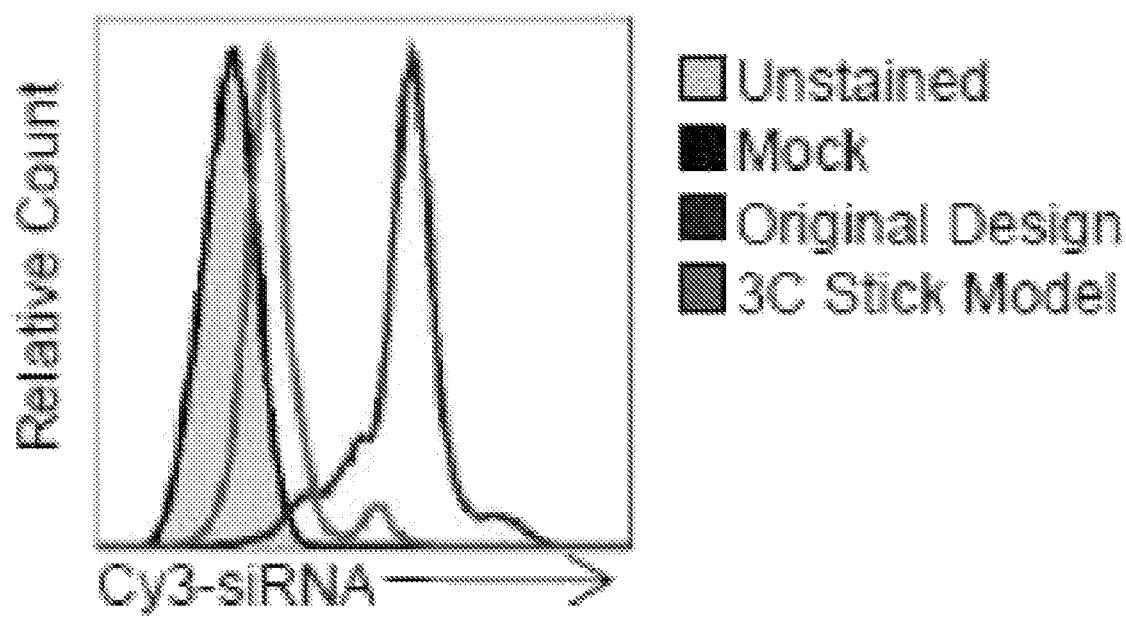
Figure 14C:
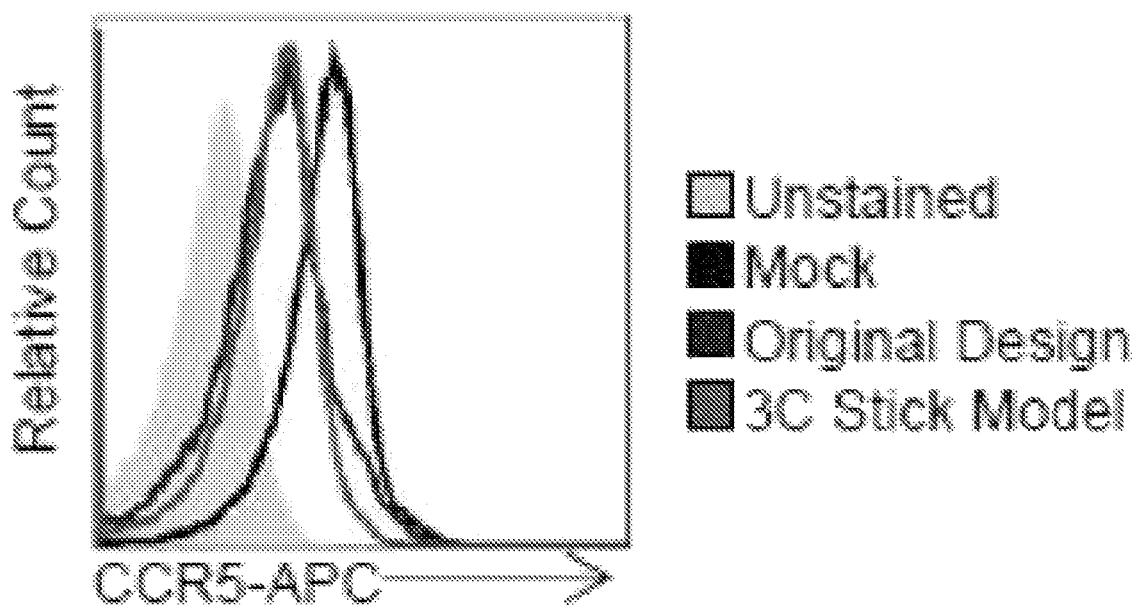
Figure 15:
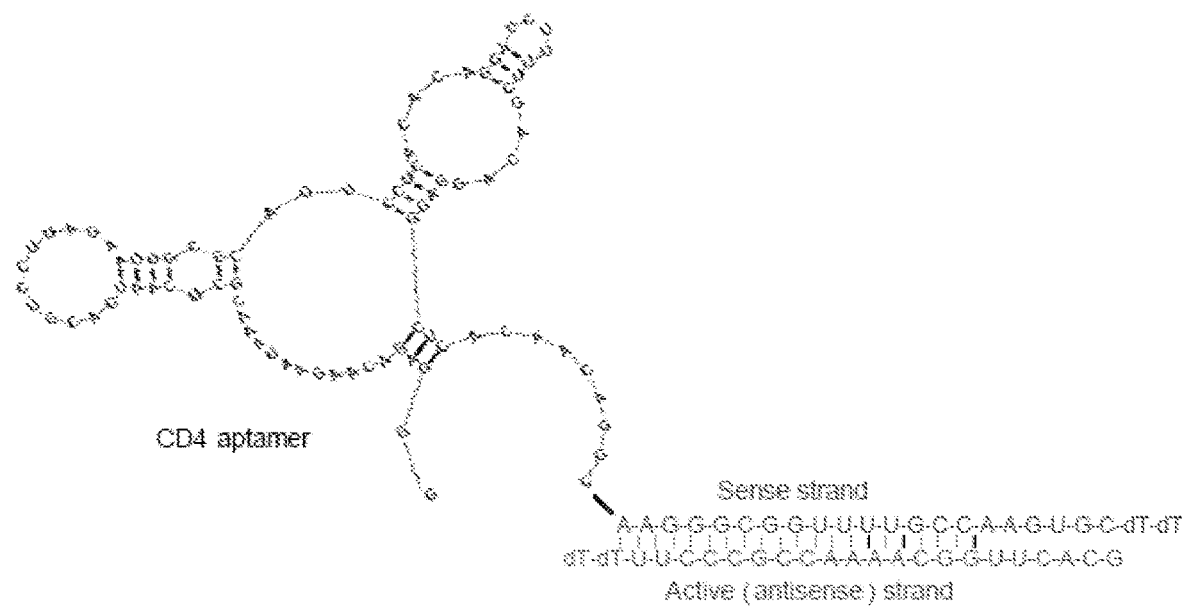
FIG. 15 is a schematic representation of an aptamer-siRNA chimera where the aptamer and sense strand of the siRNA are linked together by a phosphodiester intersugar linkage. As shown, the CD4 aptamer and sense strand of the siRNA are in vitro transcribed as a single RNA that is then annealed to the siRNA antisense oligonucleotide. Alternatively, the CD4 aptamer and antisense strand of the siRNA can be in vitro transcribed as a single RNA that can then be annealed to the siRNA sense oligonucleotide. Sequences shown are SEQ ID NO: 67 (aptamer+sense) and SEQ ID NO: 61 (antisense).

| | | |
|---|---|---|
| FIG. 1A | Aptamer (clone 9) + Sense strand (no 2Us at 3' end): 5'-GGG AGA CAA GAA UAA ACG CUC AAU GAC GUC CUU AGA AUU GCG CAU UCC UCA CAC AGG AUC UUU UCG ACA GGA GGC UCA CAA CAG GC CUC UGC UUC GGU GUC GAA A-3' | SEQ ID NO: 67 |
| | Antisense: 5'-UUU CGA CAC CGA AGC AGA G dTdT-3' | SEQ ID NO: 58 |
| FIG. 5B | Aptamer (clone 9) + Sense strand (2Us at 3' end): 5'-GGG AGA CAA GAA UAA ACG CUC AAU GAC GUC CUU AGA AUU GCG CAU UCC UCA CAC AGG AUC UUU UCG ACA GGA GGC UCA CAA CAG GC CUC UGC UUC GGU GUC GAA AUU-3' | SEQ ID NO: 68 |
| | Antisense: 5'-UUU CGA CAC CGA AGC AGA G dTdT-3' | SEQ ID NO: 58 |
| FIG. 5C | Aptamer (clone 12) + Sense strand: 5'-GGG AGA CAA GAA UAA ACG CUC AAG UGA CGU CCU GAU CGA UUG UGC AUU CGG UGU GAC GAU CUU UCG ACA GGA GGC UCA CAA CAG GC CUC UGC UUC GGU GUC GAA AUU-3' | SEQ ID NO: 70 |
| | Antisense: 5'UUU CGA CAC CGA AGC AGA G dTdT-3' | SEQ ID NO: 58 |
| FIG. 14 | Aptamer (clone 9) 5'-GGG AGA CAA GAA UAA ACG CUC AAU GAC GUC CUU AGA AUU GCG CAU UCC UCA CAC AGG AUC UUU UCG ACA GGA GGC UCA CAA CAG GC-3' | SEQ ID NO: 62 |
| | Sense + linker: 5'-CUC UGC UUC GGU GUC GAA AUU-(3C)-UGC CUG UUG-3' (3C = 3 carbon linker) | SEQ ID NOS 59 and 75 |
| | Antisense: 5'-UUU CGA CAC CGA AGC AGA G dTdT-Cy3-3' (Cy3 = Cy3 dye) | SEQ ID NO: 71 |
| FIG. 15 | Aptamer (clone 9) + sense strand: 5'-GGG AGA CAA GAA UAA ACG CUC AAU GAC GUC CUU AGA AUU GCG CAU UCC UCA CAC AGG AUC UUU UCG ACA GGA GGC UCA CAA CAG GC AAG GGG CGG UUU UGC CAA GUG-3' | SEQ ID NO: 67 |
| | Antisense: 5'-CAC UUG GCA AAA CCG CCC AA dTdT-3' | SEQ ID NO: 61 |

REFERENCES

1. Abdool Karim Q, et al. Effectiveness and safety of tenofovir gel, an antiretroviral microbicide, for the prevention of HIV infection in women. Science. 2010; 329 (5996):1168-1174.
2. Grant R M, et al. Whither or wither microbicides? Science. 2008; 321(5888):532-534.
3. Novina C D, et al. siRNA-directed inhibition of HIV-1 infection. Nat Med. 2002; 8(7):681-686.
4. Capodici J, Kariko K, Weissman D. Inhibition of HIV-1 infection by small interfering RNA-mediated RNA interference. J Immunol. 2002; 169(9):5196-5201.
5. Jacque Triques K, Stevenson M. Modulation of IIIV-1 replication by RNA interference. Nature. 2002; 418 (6896):435-438.
6. Lee N S, et al. Expression of small interfering RNAs targeted against HIV-1 rev transcripts in human cells. Nat Biotechnol. 2002; 20(5):500-505.
7. Coburn G A, Cullen B R. Potent and specific inhibition of human immunodeficiency virus type 1 replication by RNA interference. J Virol. 2002; 76(18):9225-9231.
8. Song E, et al. Sustained small interfering RNA-mediated human immunodeficiency virus type 1 inhibition in primary macrophages. J Virol. 2003; 77(13):7174-7181.
9. Lee S K, et al. Lentiviral delivery of short hairpin RNAs protects CD4 T cells from multiple clades and primary isolates of HIV. Blood. 2005; 106(3):818-826.

10. van't Wout A B, et al. Macrophage-tropic variants initiate human immunodeficiency virus type 1 infection after sexual, parenteral, and vertical transmission. J Clin Invest. 1994; 94(5):2060-2067.
11. Margolis L, Shattock R. Selective transmission of CCR5-utilizing HIV-1: the 'gatekeeper' problem resolved? Nat Rev Microbiol. 2006; 4(4):312-317.
12. Mills S G, DeMartino J A. Chemokine receptor-directed agents as novel anti-HIV-1 therapies. Curr Top Med Chem. 2004; 4(10):1017-1033.
13. Lederman M M, et al. Prevention of vaginal SHIV transmission in rhesus macaques through inhibition of CCR5. Science. 2004; 306(5695):485-487.
14. Gulick R M, et al. Phase 2 study of the safety and efficacy of vicriviroc, a CCR5 inhibitor, in HIV-1-Infected, treatment-experienced patients: AIDS clinical trials group 5211. J Infect Dis. 2007; 196(2):304-312.
15. Gulick R M, et al. Maraviroc for previously treated patients with R5 HIV-1 infection. N Engl J Med. 2008; 359(14):1429-1441.
16. Fatkenheuer G, et al. Subgroup analyses of maraviroc in previously treated R5 HIV-1 infection. N Engl J Med. 2008; 359(14):1442-1455.
17. Kuritzkes D R. HIV-1 entry inhibitors: an overview. Curr Opin HIV AIDS. 2009; 4(2):82-87.
18. Dean M, et al. Genetic restriction of IIIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science. 1996; 273 (5283):1856-1862.
19. Samson M, et al. Resistance to HIV-1 infection in caucasian individuals bearing mutant alleles of the CCR-5 chemokine receptor gene. Nature. 1996; 382(6593):722-725.
20. Huang Y, et al. The role of a mutant CCR5 allele in HIV-1 transmission and disease progression. Nat Med. 1996; 2(11):1240-1243.
21. Zimmerman P A, et al. Inherited resistance to HIV-1 conferred by an inactivating mutation in CC chemokine receptor 5: studies in populations with contrasting clinical phenotypes, defined racial background, and quantified risk. Mol Med. 1997; 3(1):23-36.
22. Galvani A P, Novembre J. The evolutionary history of the CCR5-Delta32 HIV-resistance mutation. Microbes Infect. 2005; 7(2):302-309.
23. Palliser D, et al. An siRNA-based microbicide protects mice from lethal herpes simplex virus 2 infection. Nature. 2006; 439(7072):89-94.
24. Wu Y, et al. Durable protection from Herpes Simplex Virus-2 transmission following intravaginal application of siRNAs targeting both a viral and host gene. Cell Host Microbe. 2009; 5(1):84-94.
25. Song E, et al. Antibody mediated in vivo delivery of small interfering RNAs via cell-surface receptors. Nat Biotechnol. 2005; 23(6):709-717.
26. Peer D, Zhu P, Carman C V, Lieberman J, Shimaoka M. Selective gene silencing in activated leukocytes by targeting siRNAs to the integrin lymphocyte function-associated antigen-1. Proc Natl Acad Sci USA. 2007; 104(10): 4095-4100.
27. Kumar P, et al. T cell-specific siRNA delivery suppresses HIV-1 infection in humanized mice. Cell. 2008; 134(4): 577-586.
28. McNamara J O 2nd, et al. Cell type-specific delivery of siRNAs with aptamer-siRNA chimeras. Nat Biotechnol. 2006; 24(8):1005-1015.
29. Dassie J P, et al. Systemic administration of optimized aptamer-siRNA chimeras promotes regression of PSMA-expressing tumors. Nat Biotechnol. 2009; 27(9):839-849.
30. Zhou J, Li H, Li S, Zaia J, Rossi J J. Novel dual inhibitory function aptamer-siRNA delivery system for HIV-1 therapy. Mol Ther. 2008; 16(8):1481-1489.
31. Zhou J, et al. Selection, characterization and application of new RNA HIV gp 120 aptamers for facile delivery of Dicer substrate siRNAs into HIV infected cells. Nucleic Acids Res. 2009; 37(9):3094-3109.
32. Neff C P, et al. An aptamer-siRNA chimera suppresses HIV-1 viral loads and protects from helper CD4(+) T cell decline in humanized mice. Sci Transl Med. 2011; 3(66): 66ra66.
33. Davis K A, Lin Y, Abrams B, Jayasena S D Staining of cell surface human CD4 with 2-F-pyrimidine-containing RNA aptamers for flow cytometry. Nucleic Acids Res. 1998; 26(17):3915-3924.
34. Shultz L D, Ishikawa F, Greiner D L. Humanized mice in translational biomedical research. Nat Rev Immunol. 2007; 7(2):118-130.
35. Cummins J M, et al. The colorectal microRNAome. Proc Natl Acad Sci USA. 2006; 103(10):3687-3692.
36. Soutschek J, et al. Therapeutic silencing of an endogenous gene by systemic administration of modified siRNAs. Nature. 2004; 432(7014):173-178.
37. Elbashir S M, Lendeckel W, Tuschl T. RNA interference is mediated by 21- and 22-nucleotide RNAs. Genes Dev. 2001; 15(2):188-200.
38. Arthos J, et al. Identification of the residues in human CD4 critical for the binding of HIV. Cell. 1989; 57(3): 469-481.
39. Greenhead P, Hayes P, Watts P S, Laing K G, Griffin G E, Shattock R J. Parameters of human immunodeficiency virus infection of human cervical tissue and inhibition by vaginal virucides. J Virol. 2000; 74(12):5577-5586.
40. Collins K B, Patterson B K, Naus G J, Landers D V, Gupta P. Development of an in vitro organ culture model to study transmission of HIV-1 in the female genital tract. Nat Med. 2000; 6(4):475-479.
41. Robbins M, Judge A, Maci,achl an T. siRNA and innate immunity. Oligonucleotides. 2009; 19(2):89-102.
42. Brainard D M, et al. Induction of robust cellular and humoral virus-specific adaptive immune responses in human immunodeficiency virus-infected humanized BLT mice. J Virol. 2009; 83(14):7305-7321.
43. Berges B K, Akkina S R, Folkvord J M, Connick E, Akkina R. Mucosal transmission of R5 and X4 tropic HIV-1 via vaginal and rectal routes in humanized Rag2-/- gammac-/-(RAG-hu) mice. Virology. 2008; 373(2):342-351.
44. Denton P W, et al. Antiretroviral pre-exposure prophylaxis prevents vaginal transmission of HIV-1 in humanized BLT mice. PLoS Med. 2008; 5(1):e16.
45. Peer D, Park E J, Morishita Y, Carman C V, Shimaoka M. Systemic leukocyte-directed siRNA delivery revealing cyclin D1 as an anti-inflammatory target. Science. 2008; 319(5863):627-630.
46. Haase A T. Targeting early infection to prevent HIV-1 mucosal transmission. Nature. 2010; 464(7286):217-223.
47. Brass A L, et al. Identification of host proteins required for HIV infection through a functional genomic screen. Science. 2008; 319(5865):921-926.
48. Shun M C, et al. LEDGF/p75 functions downstream from preintegration complex formation to effect gene-specific HIV-1 integration. Genes Dev. 2007; 21(14): 1767-1778.

49. Boutwell C L, Rowley C F, Essex M. Reduced viral replication capacity of human immunodeficiency virus type 1 subtype C caused by cytotoxic-T-lymphocyte escape mutations in HLA-B57 epitopes of capsid protein. J Virol. 2009; 83(6):2460-2468.
50. Armbruster D A, Pry T. Limit of blank, limit of detection and limit of quantitation. Clin Biochem Rev. 2008; 29(suppl 1):S49-S52.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

We claim:

1. A method of inhibiting HIV infection in a cell, the method comprising contacting the cell with a conjugate comprising an aptamer and a gene modulator, wherein the aptamer is a CD4 aptamer and the gene modulator inhibits the expression of a HIV gene, a cell gene required for HIV infection, or any combinations thereof, wherein the aptamer and the gene modulator are linked to each other by a double-stranded linker comprising a first oligonucleotide strand and a second oligonucleotide strand, wherein the first oligonucleotide strand of the double-stranded linker is linked to the aptamer by a nucleotidic linker and the second oligonucleotide strand of the double-stranded linker is linked to the gene modulator by a non-nucleotidic linker, and wherein the conjugate comprises nucleotide sequences selected from: (i) SEQ ID NOs: 58 and 68; (ii) SEQ ID NOs: 58 and 70; (iii) SEQ ID NOs: 59, 62, and 71; and (iv) SEQ ID NOs: 61 and 67.

2. The method of inhibiting HIV infection in a cell according to claim 1, wherein the linker double-stranded oligonucleotide comprises 5 to 15 nucleotide base pairs.

3. The method of inhibiting HIV infection in a cell according to claim 1, the non-nucleotidic linker is an optionally substituted $C_3$-$C_{10}$ alkyl.

4. The method of inhibiting HIV infection in a cell according to claim 1, wherein the non-nucleotidic linker is —$OCH_2CH_2CH_2O$— (C3 linker).

5. The method of inhibiting HIV infection in a cell according to claim 1, wherein the first strand is linked to 3'-end of the aptamer.

6. The method of inhibiting HIV infection in a cell according to claim 1, wherein the gene modulator is a double-stranded oligonucleotide comprising a sense strand and an antisense strand.

7. The method of inhibiting HIV infection in a cell according to claim 6, wherein the second strand of the double-stranded linker is linked to 3'-end of the sense strand by the non-nucleotidic linker.

* * * * *

SEQUENCE LISTING

```
<160> NUMBER OF SEQ ID NOS: 78

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
taatacgact cactataggg agacaagaat aaacgc                                 36

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
taatacgact cactataggg aggaggacga tgcgga                                 36

<210> SEQ ID NO 3
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggagacaag aataaacgct caatgacgtc cttagaattg cgcattcctc acacaggatc       60
ttttcgacag gaggctcaca acaggc                                            86

<210> SEQ ID NO 4
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gggagacaag aataaacgct caagtgacgt cctgatcgat tgtgcattcg gtgtgacgat       60
ctttcgacag gaggctcaca acaggc                                            86

<210> SEQ ID NO 5
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
gggaggacga tgcggatcag ccatgtttac gtcactcctt gtcaatcctc atcggcagac      60
tcgcccga                                                                68

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcctgttgtg agcctcctgt cgaa                                              24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcgggcgagt cgtcgtctgc cgatg                                             25

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aattctccga acgtctcacg tgcctgttgt gagcctcctg tcgaa                        45

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aattctccga acgtctcacg ttcgggcgag tcgtcgtctg ccgatg                       46

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aatttcgaca ccgaagcaga ggcctgttgt gagcctcctg tcgaa                        45

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 11
aatttcgaca ccgaagcaga gtcgggcgag tcgtcgtctg ccgatg         46

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aatgttcttc tggaagtcca ggcctgttgt gagcctcctg tcgaa          45

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aatgttcttc tggaagtcca gtcgggcgag tcgtcgtctg ccgatg         46

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aacctgtctc tcagtacaat cgcctgttgt gagcctcctg tcgaa          45

<210> SEQ ID NO 15
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aacctgtctc tcagtacaat ctcgggcgag tcgtcgtctg ccgatg         46

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagggatgtg tacttctgaa cgcctgttgt gagcctcctg tcgaa          45

<210> SEQ ID NO 17
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagggatgtg tacttctgaa ctcgggcgag tcgtcgtctg ccgatg        46

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaattgtctt caggtcttca ggcctgttgt gagcctcctg tcgaa         45

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aatgctctga aattcagcca ggcctgttgt gagcctcctg tcgaa         45

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aatcgaagta ctcagcgtaa ggcctgttgt gagcctcctg tcgaa         45

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgagaacagg ctgcagacca tgaa                               24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caaactcacg ctgcttccca ttgt                               24

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agccacatcg ctcagacac                                               19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcccaatacg accaaatcc                                               19

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agacagcaga gcacacaagc                                              20

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atggttcctt ccggtggt                                                18

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gatgagtaca aaagtcctga tcca                                         24

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctgcagccac tggttctgt                                               19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
ttgctctggc acaacaggta                                          20
```

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
tggagaagca accaggaga                                           19
```

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
ggcattttga agaattggaa ag                                       22
```

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
tttggatgct ctggtcatct t                                        21
```

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
ggtggagttc gatgtgctg                                           19
```

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
aggtttatag ccgccagtca                                          20
```

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaaagcagtt agcaaggaaa ggt                                          23

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gacatatact ccatgtaggg aagtga                                       26

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttggcaccta acgtgctg                                                18

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttcgtaccac tgagacatcc tg                                           22

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cactcccaaa acctgctgct gag                                          23

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tctcttcaga agtgcaaggg ta                                           22

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agtgggggga catcaagcag ccatgcaaat                                   30

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgctatgtca cttccccttg gttctct                                             27

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 43
cucugcuucg gugucgaaat t                                                   21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 44
uuucgacacc gaagcagagt t                                                   21

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 45
gauuguacug agagacaggc utt                                                 23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<220> FEATURE:
<223> OTHER INFORMATION: 5' Phosphate

<400> SEQUENCE: 46
ccugucucuc ucaguacaau ctt                                          23

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 47
gttcagaagt acacatccct t                                            21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 48
gggaugugua cuucugaact t                                            21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 49
cuuacgcuga guacuucgat t                                            21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 50
ucgaaguacu cagcguaagt t                                            21
```

-continued

```
<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 51
cuggcugaau ucagagcat t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 52
ugcucugaaa uucagccagt t                                             21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 53
cuggacuucc agaagaacat t                                             21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 54
uguucuucug gaaguccagt t                                             21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 55
cugaagaccu gaagacaaut t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Phosphate

<400> SEQUENCE: 56
auugucuuca ggucuucagt t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
cucugcuucg gugucgaaat t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
uuucgacacc gaagcagagt t                                              21

<210> SEQ ID NO 59
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: U-3-carbon linker

<400> SEQUENCE: 59
cucugcuucg gugucgaaau uugccuguug                                     30
```

```
<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60 aagggcggu uuugccaagu g                                              21

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
cacuuggcaa aaccgcccca att                                           23

<210> SEQ ID NO 62
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gggagacaag aauaaacgcu caaugacguc cuuagaauug cgcauuccuc acacaggauc   60
uuuucgacag gaggcucaca acaggc                                       86

<210> SEQ ID NO 63
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gggagacaag aauaaacgcu caagugacgu ccugaucgau ugugcauucg gugugacgau   60
cuuucgacag gaggcucaca acaggc                                       86

<210> SEQ ID NO 64
<211> LENGTH: 68
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
gggaggacga ugcggaucag ccauguuuac gucacuccuu gucaauccuc aucggcagac   60
ucgcccga                                                           68

<210> SEQ ID NO 65
<211> LENGTH: 24
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 65
cucaaugacg uccuuagaau ugcg                                           24

<210> SEQ ID NO 66
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uuccucacac aggaucuuuu cgacaggagg                                     30

<210> SEQ ID NO 67
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 67
gggagacaag aauaaacgcu caaugacguc cuuagaauug cgcauuccuc acacaggauc    60
uuuucgacag gaggcucaca acaggccucu gcuucggugu cgaaa                  105

<210> SEQ ID NO 68
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 68
gggagacaag aauaaacgcu caaugacguc cuuagaauug cgcauuccuc acacaggauc    60
uuuucgacag gaggcucaca acaggccucu gcuucggugu cgaaauu                107

<210> SEQ ID NO 69

<400> SEQUENCE: 69

000

<210> SEQ ID NO 70
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 70
gggagacaag aauaaacgcu caagugacgu ccugaucgau ugugcauucg gugugacgau    60
cuuucgacag gaggcucaca acaggccucu gcuucggugu cgaaauu                107

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 71
uuucgacacc gaagcagagt t                                                    21

<210> SEQ ID NO 72
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72 caacaggc                                                                    8

<210> SEQ ID NO 73
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, u, g, unknown or other and this region
      may encompass 0 to 4 bases in length

<400> SEQUENCE: 73
nnnngccugu ug                                                              12

<210> SEQ ID NO 74
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74 ugccuguug                                                                   9

<210> SEQ ID NO 75
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 3-carbon linker-U

<400> SEQUENCE: 75 ugccuguug                                                                   9

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 76
cucugcuucg gugucgaaa                                                19

<210> SEQ ID NO 77
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(33)
<223> OTHER INFORMATION: a, c, t, g, unknown or other

<400> SEQUENCE: 77
cgcnnnnnnn nnnnnnnnnn nnnnnnnnnn nnnaaagtgt cgaaa                   45

<210> SEQ ID NO 78
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(42)
<223> OTHER INFORMATION: a, c, t, g, unknown or other

<400> SEQUENCE: 78
tttcgacact ttnnnnnnnn nnnnnnnnnn nnnnnnnnnn nngcg                   45
```